United States Patent
West et al.

(10) Patent No.: US 6,368,789 B1
(45) Date of Patent: Apr. 9, 2002

(54) SCREENING METHODS TO IDENTIFY INHIBITORS OF TELOMERASE ACTIVITY

(76) Inventors: Michael D. West, 15 Wakefield Ct., Belmont, CA (US) 94002; Jerry Shay, 5060 Horseshoe Trail, Dallas, TX (US) 75209; Woodring Wright, 5060 Country Green La., Arlington, TX (US) 76011; Elizabeth H. Blackburn, 294 Yerba Buena Ave., San Francisco, CA (US) 94127

( * ) Notice: Subject to any disclaimer, the term of this patent is extended or adjusted under 35 U.S.C. 154(b) by 0 days.

(21) Appl. No.: 08/464,011

(22) Filed: Jun. 5, 1995

Related U.S. Application Data

(60) Division of application No. 08/060,952, filed on May 13, 1993, now Pat. No. 5,695,932, which is a continuation-in-part of application No. 08/038,766, filed on Mar. 24, 1993, now Pat. No. 5,489,508, which is a continuation-in-part of application No. 07/882,438, filed on May 13, 1992, now abandoned.

(51) Int. Cl.[7] ............... C12Q 1/68; G01N 33/53; C12P 19/34

(52) U.S. Cl. ............... 435/6; 435/7.21; 435/7.22; 435/7.4; 435/7.72; 435/91.31

(58) Field of Search ............... 435/6, 7.21, 7.22, 435/7.4, 7.72, 91.31

(56) References Cited

U.S. PATENT DOCUMENTS

| | | | |
|---|---|---|---|
| 4,735,778 A | * | 4/1988 | Maruyama et al. ......... 422/102 |
| 4,737,454 A | | 12/1988 | Dattagupta et al. |
| 5,489,508 A | | 2/1996 | West et al. |
| 5,645,986 A | * | 7/1997 | West et al. ............... 435/6 |
| 5,686,245 A | * | 11/1997 | West et al. ............... 435/6 |

OTHER PUBLICATIONS

Morin The human telomere terminal transferase enzyme is a ribonucleoprotein that synthesizes TTAGGG repeats Cell vol. 59 521–529, 1989.*

Stull et al. Antigene, ribozyme and aptamer nucleic acid drugs: Progress and Prospects. Pharmaceutical Res. vol. 12 pp. 465–483, 1995.*

Uhlmann et al. Antisense oligonucleotides: A new therapeutic principle Chemical Reviews vol. 90 pp. 543–584, 1990.*

Milner et al. Selecting effective antisense reagents on combinatorial oligonucleotide arrays. Nature Biotechnology vol. 15 pp. 537–541, 1997.*

Greider et al. A telomeric sequence in the RNA of Tetrahymena telomerase required for telomere repeat synthesis. Nature vol. 337 pp. 331–336, 1989.*

Strahl et al. The effects of nucleoside analogs on telomeres in Tetrahymena. Nucleic Acids Res. vol. 22 pp. 893–900, 1994.*

Cohn et al. Telomerase in yeast. Science vol. 269 pp. 396–400, 1995.*

Morin The human telomere terminal transferase enzyme is a ribonucleoprotein that synthesizes TTAGGG repeats. Cell vol. 59 pp. 521–529, 1989.*

Harley et al. Telomeres shorten during ageing of human fibroblasts. Nature vol. 345 pp. 458–460, 1990.*

(List continued on next page.)

*Primary Examiner*—John S. Brusca
(74) *Attorney, Agent, or Firm*—Lyon & Lyon LLP

(57) ABSTRACT

Method and compositions are provided for the determination of telomere length and telomerase activity, as well as the ability to inhibit telomerase activity in the treatment of proliferative diseases. Particularly, primers are elongated under conditions which minimize interference from other genomic sequences, so as to obtain accurate determinations of telomeric length or telomerase activity. In addition, compositions are provided for intracellular inhibition of telomerase activity and means are shown for slowing the loss of telomeric repeats in aging cells.

54 Claims, 32 Drawing Sheets

OTHER PUBLICATIONS

Gebeyehu et al. Novel biotinylated nucleotide–analogs for labeling and colorimetric detection of DNA. Nucleic Acids Res. vol. 15 pp. 4513–4534, 1987.*

Strahl et al. Nucl. Acids Res. 22 893–900 (1994) The Effects of Nucleoside Analogs or Telomerase and Telomeres . . .*

Greider et al. Nature 337 331–336 (1989) A Telomeric Sequence in the RNA of Tetrahymena Telomerase . . .*

Parker et al. J. Biol. Chem. 266 1754–1762 (1991) Mechanism of Inhibition of Human Immunodeficiency Virus Type 1 . . .*

Johnston et al. Electrophoresis 11 355–360 (1990) Autoradiography Using Storage Phosphor Technology.*

Saxena et al. J. Biol. Chem. 265 17106–17109 (1990) Ribozymes Correctly Cleave Amalel Substrate and Endogenous . . .*

Greider and Blackburn, "Identification of a Specific Telomere Terminal Transferase Activity in *Tetrahymena* Extracts," *Cell* 43:405–413 (1985).

Greider, "The Role of Telomeres and Telomerase in Cellular Senescence and Immortalization," Research Proposal sent to Geron Corp. Aug. 13, 1992.

Allsopp et al., "Telomere length predicts replicative capacity of human fibroblasts," *Proc. Natl. Acad. Sci. USA* 89:10114–10118 (1992).

Zahler et al., "Inhibition of Telomerase by G–quartet DNA Structures," pp. 718–720, Nature, vol. 350, (Apr. 25, 1991).

Eck and Nabel, "Antisense oligonucleotides for therapeutic intervention", Current Opin. in Biotech, 2:897 (1991).

Harley, "Telomere Loss: Mitotic Clock or Genetic Time Bomb?" 256 Nature 271 (1991).

Harley et al., "Telomeres Shorten During Ageing of Human Fibroblasts" 345 Nature 458 (1990).

Blackburn, "Structure and Function of Telomeres", 350 Nature 569 (1991).

Cech, "Ribozymes and their medical implications", 260 J. of Amer. Med. Assoc. 3030 (1988).

Harley, Mutation Research, 256:271–282 (1991).

Counter et al., "Telomere shortening associated with chromosome instability is arrested in immortal cells which express telomerase activity," EMBO J 11:1921–1929 (May 5, 1992).

Greider et al., "Telomerase is Processive", Molecular and Cellular Biology, 11:4572–4580 (1991).

Blackburn et al., "Recognition and Elongation of Telomeres by Telomerase" Genome, 31: 553–560 (1989).

Greider and Blackburn, "The telomere terminal transferase of tetrahymena is a ribonucleoprotein enzyme with two kinds of primer specificity," Cell 51: 887–898 (1987).

Yu and Blackburn, "Developmentally programmed healing of chromosomes by telomerase in Tetrahymena", cell 67:823 (1991).

* cited by examiner

■■■■■ RATE OF LOSS: 102 bp/PD
○○○○○ RATE OF LOSS: 79 bp/PD
∧∧∧∧∧ ONLY ONE DATA POINT (AT SENESCENCE) WAS AVAILABLE

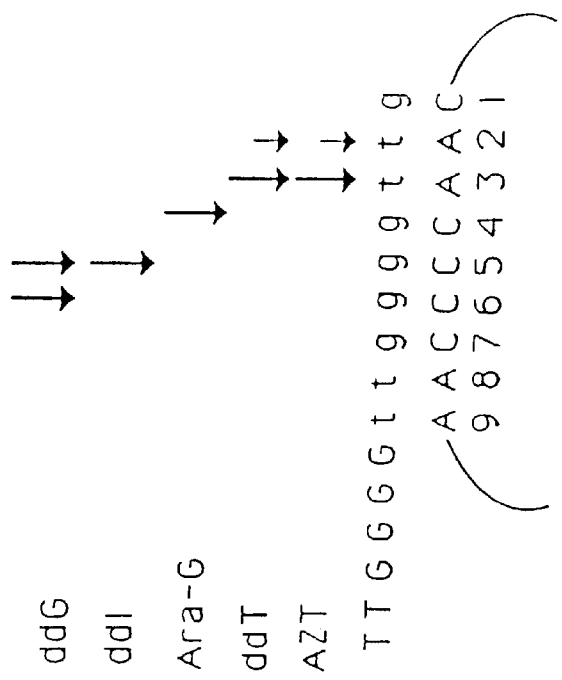
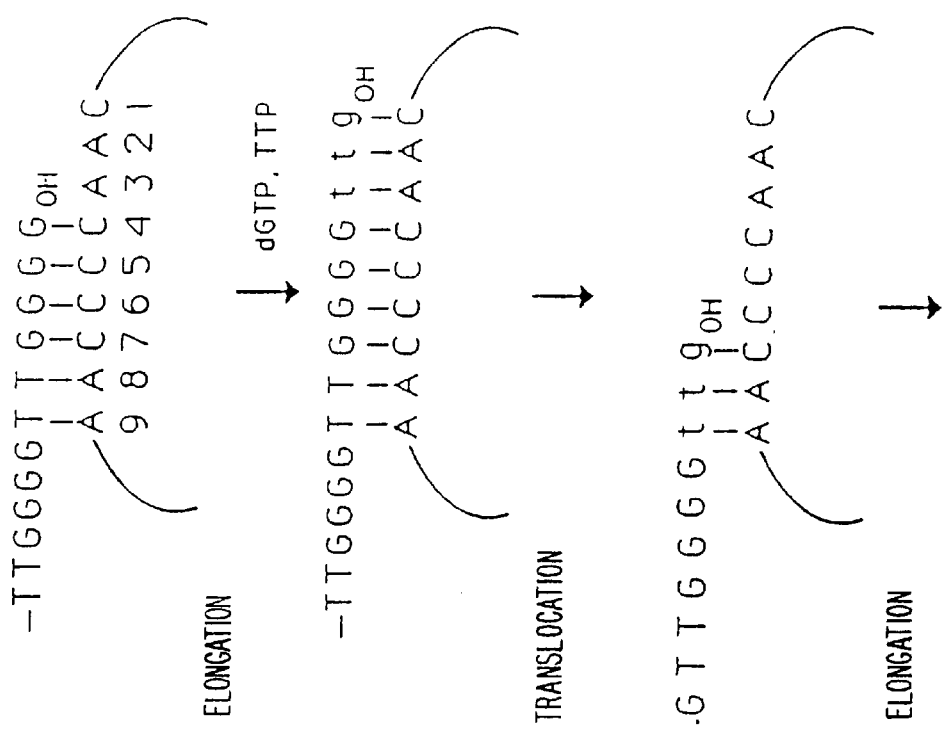
FIG. 18A.
FIG. 18B.

FIG. 30.

| Species | Telomeric Repeat |  |
|---|---|---|
| C. alb. | ACGGATGTCTAAC | TTCT TGGTGT |
| C. tro. 4414 | AC/AGGATGTCACGA | TCAT TGGTGT |
| C. tro. 4443 | AAGGATGTCACGA | TCAT TGGTGT |
| C. mal. | ACGGATGCAGACT | CGCT TGGTGT |
| C. gui. | AC | TGGTGT |
| C. pse. | ACGGATTTGATTAGTT | TGGTGT |
| K. lac. | ACGGATTTGATTAGGT | ATG TGGTGT |
| C. gla. | CTGGGTGC | TG TGGTGT |
| S. cer. | | T(G)$_{2-3}$(TG)$_{1-6}$ |

5'  ToEnd→  3'

AC probe

AA probe

```
                           SEQUENCE LISTING (1) GENERAL INFORMATION:

(iii) NUMBER OF SEQUENCES: 61

(2) INFORMATION FOR SEQ ID NO: 1:

(i) SEQUENCE CHARACTERISTICS:
          (A) LENGTH: 60
          (B) TYPE: nucleic acid
          (C) STRANDEDNESS: single
          (D) TOPOLOGY: linear (xi) SEQUENCE DESCRIPTION: SEQ ID NO: 1:

TTAGGGTTAG GGTTAGGGTT AGGGTTAGGG TTAGGGTTAG GGTTAGGGTT AGGGTTAGGG         60

(2) INFORMATION FOR SEQ ID NO: 2:

(i) SEQUENCE CHARACTERISTICS:
          (A) LENGTH: 12
          (B) TYPE: nucleic acid
          (C) STRANDEDNESS: single
          (D) TOPOLOGY: linear (xi) SEQUENCE DESCRIPTION: SEQ ID NO: 2:

CCCTAACCCT AA                                                            12

(2) INFORMATION FOR SEQ ID NO: 3:

(i) SEQUENCE CHARACTERISTICS:
          (A) LENGTH: 12
          (B) TYPE: nucleic acid
          (C) STRANDEDNESS: single
          (D) TOPOLOGY: linear (xi) SEQUENCE DESCRIPTION: SEQ ID NO: 3:

TTAGGGTTAG GG                                                            12

(2) INFORMATION FOR SEQ ID NO: 4:

(i) SEQUENCE CHARACTERISTICS:
          (A) LENGTH: 18
          (B) TYPE: nucleic acid
          (C) STRANDEDNESS: single
          (D) TOPOLOGY: linear (xi) SEQUENCE DESCRIPTION: SEQ ID NO: 4:

CCCTAACCCT AACCCTAA                                                      18

(2) INFORMATION FOR SEQ ID NO: 5:

(i) SEQUENCE CHARACTERISTICS:
          (A) LENGTH: 18
          (B) TYPE: nucleic acid
          (C) STRANDEDNESS: single
          (D) TOPOLOGY: linear (xi) SEQUENCE DESCRIPTION: SEQ ID NO: 5:

TTAGGGTTAG GGTTAGGG                                                      18
```

(2) INFORMATION FOR SEQ ID NO: 6:

(i) SEQUENCE CHARACTERISTICS:
        (A) LENGTH: 24
        (B) TYPE: nucleic acid
        (C) STRANDEDNESS: single
        (D) TOPOLOGY: linear (xi) SEQUENCE DESCRIPTION: SEQ ID NO: 6:

CCCTAACCCT AACCCTAACC CTAA                                              24

(2) INFORMATION FOR SEQ ID NO: 7:

(i) SEQUENCE CHARACTERISTICS:
        (A) LENGTH: 12
        (B) TYPE: nucleic acid
        (C) STRANDEDNESS: single
        (D) TOPOLOGY: linear (xi) SEQUENCE DESCRIPTION: SEQ ID NO: 7:

CCCTAACCCT AA                                                                    12

(2) INFORMATION FOR SEQ ID NO: 8:

(i) SEQUENCE CHARACTERISTICS:
        (A) LENGTH: 13
        (B) TYPE: nucleic acid
        (C) STRANDEDNESS: single
        (D) TOPOLOGY: linear (xi) SEQUENCE DESCRIPTION: SEQ ID NO: 8:

ACGGATGTCT AAC                                                                 13

(2) INFORMATION FOR SEQ ID NO: 9:

(i) SEQUENCE CHARACTERISTICS:
        (A) LENGTH: 10
        (B) TYPE: nucleic acid
        (C) STRANDEDNESS: single
        (D) TOPOLOGY: linear (xi) SEQUENCE DESCRIPTION: SEQ ID NO: 9:

TTCTTGGTGT                                                                     10

(2) INFORMATION FOR SEQ ID NO: 10:

(i) SEQUENCE CHARACTERISTICS:
        (A) LENGTH: 13
        (B) TYPE: nucleic acid
        (C) STRANDEDNESS: single
        (D) TOPOLOGY: linear (xi) SEQUENCE DESCRIPTION: SEQ ID NO: 10:

ACGGATGTCA CGA                                                                13

(2) INFORMATION FOR SEQ ID NO: 11:

(i) SEQUENCE CHARACTERISTICS:
        (A) LENGTH: 10
        (B) TYPE: nucleic acid
        (C) STRANDEDNESS: single
        (D) TOPOLOGY: linear (xi) SEQUENCE DESCRIPTION: SEQ ID NO: 11:

TCATTGGTGT                                                                     10

(2) INFORMATION FOR SEQ ID NO: 12:

(i) SEQUENCE CHARACTERISTICS:
        (A) LENGTH: 13
        (B) TYPE: nucleic acid
        (C) STRANDEDNESS: single
        (D) TOPOLOGY: linear (xi) SEQUENCE DESCRIPTION: SEQ ID NO: 12:

AAGGATGTCA CGA                                                                             13

(2) INFORMATION FOR SEQ ID NO: 13:

(i) SEQUENCE CHARACTERISTICS:
        (A) LENGTH: 13
        (B) TYPE: nucleic acid
        (C) STRANDEDNESS: single
        (D) TOPOLOGY: linear (xi) SEQUENCE DESCRIPTION: SEQ ID NO: 13:

ACGGATGCAG ACT                                                                             13

(2) INFORMATION FOR SEQ ID NO: 14:

(i) SEQUENCE CHARACTERISTICS:
        (A) LENGTH: 10
        (B) TYPE: nucleic acid
        (C) STRANDEDNESS: single
        (D) TOPOLOGY: linear (xi) SEQUENCE DESCRIPTION: SEQ ID NO: 14:

CGCTTGGTGT                                                                                 10

(2) INFORMATION FOR SEQ ID NO: 15:

(i) SEQUENCE CHARACTERISTICS:
        (A) LENGTH: 25
        (B) TYPE: nucleic acid
        (C) STRANDEDNESS: single
        (D) TOPOLOGY: linear (xi) SEQUENCE DESCRIPTION: SEQ ID NO: 15:

ACGGATTTGA TTAGTTATGT GGTGT                                    25

(2) INFORMATION FOR SEQ ID NO: 16:

(i) SEQUENCE CHARACTERISTICS:
        (A) LENGTH: 25
        (B) TYPE: nucleic acid
        (C) STRANDEDNESS: single
        (D) TOPOLOGY: linear (xi) SEQUENCE DESCRIPTION: SEQ ID NO: 16:

ACGGATTTGA TTAGGTATGT GGTGT                                    25

(2) INFORMATION FOR SEQ ID NO: 17:

(i) SEQUENCE CHARACTERISTICS:
        (A) LENGTH: 8
        (B) TYPE: nucleic acid
        (C) STRANDEDNESS: single
        (D) TOPOLOGY: linear (xi) SEQUENCE DESCRIPTION: SEQ ID NO: 17:

CTGGGTGC                                                                                      8

(2) INFORMATION FOR SEQ ID NO: 18:

```
        (i) SEQUENCE CHARACTERISTICS:
            (A) LENGTH: 8
            (B) TYPE: nucleic acid
            (C) STRANDEDNESS: single
            (D) TOPOLOGY: linear (xi) SEQUENCE DESCRIPTION: SEQ ID NO: 18:

TGTGGGGT                                                                  8

(2) INFORMATION FOR SEQ ID NO: 19:

(i) SEQUENCE CHARACTERISTICS:
            (A) LENGTH: 11
            (B) TYPE: nucleic acid
            (C) STRANDEDNESS: single
            (D) TOPOLOGY: linear (xi) SEQUENCE DESCRIPTION: SEQ ID NO: 19:

GTGTAAGGAT G                                                             11

(2) INFORMATION FOR SEQ ID NO: 20:

(i) SEQUENCE CHARACTERISTICS:
            (A) LENGTH: 5 base pairs
            (B) TYPE: nucleic acid
            (C) STRANDEDNESS: single
            (D) TOPOLOGY: linear (xi) SEQUENCE DESCRIPTION: SEQ ID NO: 20:

TGGTG                                                                     5

(2) INFORMATION FOR SEQ ID NO: 21:

(i) SEQUENCE CHARACTERISTICS:
            (A) LENGTH: 12
            (B) TYPE: nucleic acid
            (C) STRANDEDNESS: single
            (D) TOPOLOGY: linear (xi) SEQUENCE DESCRIPTION: SEQ ID NO: 21:

ACGGATGTCA CG                                                            12

(2) INFORMATION FOR SEQ ID NO: 22:

(i) SEQUENCE CHARACTERISTICS:
            (A) LENGTH: 11
            (B) TYPE: nucleic acid
            (C) STRANDEDNESS: single
            (D) TOPOLOGY: linear (xi) SEQUENCE DESCRIPTION: SEQ ID NO: 22:

GTGTAAGGAT G                                                             11

(2) INFORMATION FOR SEQ ID NO: 23:

(i) SEQUENCE CHARACTERISTICS:
            (A) LENGTH: 26
            (B) TYPE: nucleic acid
            (C) STRANDEDNESS: single
            (D) TOPOLOGY: linear (xi) SEQUENCE DESCRIPTION: SEQ ID NO: 23:

TTAGGGTTAG GGTTAGGGGG GGGGGG                                             26

(2) INFORMATION FOR SEQ ID NO: 24:
```

(i) SEQUENCE CHARACTERISTICS:
            (A) LENGTH: 26
            (B) TYPE: nucleic acid
            (C) STRANDEDNESS: single
            (D) TOPOLOGY: linear (xi) SEQUENCE DESCRIPTION: SEQ ID NO: 24:

TTAGGGTTAG GGTTGGGGGG GGGGGG                                            26

(2) INFORMATION FOR SEQ ID NO: 25:

(i) SEQUENCE CHARACTERISTICS:
            (A) LENGTH: 26
            (B) TYPE: nucleic acid
            (C) STRANDEDNESS: single
            (D) TOPOLOGY: linear (xi) SEQUENCE DESCRIPTION: SEQ ID NO: 25:

TTAGGGTTAG GGTGGGGGGG GGGGGG                                            26

(2) INFORMATION FOR SEQ ID NO: 26:

(i) SEQUENCE CHARACTERISTICS:
            (A) LENGTH: 16
            (B) TYPE: nucleic acid
            (C) STRANDEDNESS: single
            (D) TOPOLOGY: linear (xi) SEQUENCE DESCRIPTION: SEQ ID NO: 26:

CCCCCCCCTA ACCCTA                                                       16

(2) INFORMATION FOR SEQ ID NO: 27:

(i) SEQUENCE CHARACTERISTICS:
            (A) LENGTH: 16
            (B) TYPE: nucleic acid
            (C) STRANDEDNESS: single
            (D) TOPOLOGY: linear (xi) SEQUENCE DESCRIPTION: SEQ ID NO: 27:

CCCCCCCCAA CCCTAA                                                       16

(2) INFORMATION FOR SEQ ID NO: 28:

(i) SEQUENCE CHARACTERISTICS:
            (A) LENGTH: 16
            (B) TYPE: nucleic acid
            (C) STRANDEDNESS: single
            (D) TOPOLOGY: linear (xi) SEQUENCE DESCRIPTION: SEQ ID NO: 28:

CCCCCCCCAC CCTAAC                                                       16

(2) INFORMATION FOR SEQ ID NO: 29:

(i) SEQUENCE CHARACTERISTICS:
            (A) LENGTH: 24
            (B) TYPE: nucleic acid
            (C) STRANDEDNESS: single
            (D) TOPOLOGY: linear (xi) SEQUENCE DESCRIPTION: SEQ ID NO: 29:

TTAGGGTTAG GGTTAGGGTT AGGG                                              24

(2) INFORMATION FOR SEQ ID NO: 30:

(i) SEQUENCE CHARACTERISTICS:

(A) LENGTH: 37
        (B) TYPE: nucleic acid
        (C) STRANDEDNESS: single
        (D) TOPOLOGY: linear (xi) SEQUENCE DESCRIPTION: SEQ ID NO: 30:

CAATAATGTA TTAAAAATAT GCTACTTATG CATTATC                                37

(2) INFORMATION FOR SEQ ID NO: 31:

(i) SEQUENCE CHARACTERISTICS:
        (A) LENGTH: 23
        (B) TYPE: nucleic acid
        (C) STRANDEDNESS: single
        (D) TOPOLOGY: linear (xi) SEQUENCE DESCRIPTION: SEQ ID NO: 31:

TGGTACCGTC GAAAGCTTGA CTG                                               23

(2) INFORMATION FOR SEQ ID NO: 32:

(i) SEQUENCE CHARACTERISTICS:
        (A) LENGTH: 14
        (B) TYPE: nucleic acid
        (C) STRANDEDNESS: single
        (D) TOPOLOGY: linear (xi) SEQUENCE DESCRIPTION: SEQ ID NO: 32:

ATGAACTGAC CTAG                                                         14

(2) INFORMATION FOR SEQ ID NO: 33:

(i) SEQUENCE CHARACTERISTICS:
        (A) LENGTH: 170
        (B) TYPE: nucleic acid
        (C) STRANDEDNESS: single
        (D) TOPOLOGY: linear (xi) SEQUENCE DESCRIPTION: SEQ ID NO: 33:

GATCTAGGCA CAGCTGCTTC TCATTAGGCA GGTCTCAGCT AGAAGACCAC TTCCCTCCCT        60

GAGGAAGTCA ACCCTTCTGC CACCCCATGG CCTTGCTTAA ATTTTCAGAC TGTCGAATTG       120

GAATCCTACC TCCATTAGCT ACTAGCTTGG GCAAGATACA GAGCCCTCCC                  170

(2) INFORMATION FOR SEQ ID NO: 34:

(i) SEQUENCE CHARACTERISTICS:
        (A) LENGTH: 116
        (B) TYPE: nucleic acid
        (C) STRANDEDNESS: single
        (D) TOPOLOGY: linear (xi) SEQUENCE DESCRIPTION: SEQ ID NO: 34:

ATATATGCGC TACATAAATG TATCTAGATG CAATTATCTA GATACATATA AGAAAGTATT        60

TGAAGGCCTT CTACAAGGCT TAGTTATTAT ATTGGTTCAT ACAAGTTCTT CTTCAG           116

(2) INFORMATION FOR SEQ ID NO: 35:

(i) SEQUENCE CHARACTERISTICS:
        (A) LENGTH: 176
        (B) TYPE: nucleic acid
        (C) STRANDEDNESS: single
        (D) TOPOLOGY: linear (xi) SEQUENCE DESCRIPTION: SEQ ID NO: 35:

ATCCTTCTCC GCAAACTAAC AGGAACAGAA AACCAAACAC TGCATGTTCT CACATCATTG        60

TGGGAGTTGA ACAATGAGAA CACATGGACA CAGGGAGGGG AACATCACAC ACTCGGGGTG    120

TCAGCCGGGT GGGAGGGTAG AGGAGGAGAA ATACCTAAGT TCCAGATGAC AGGTTG        176

(2) INFORMATION FOR SEQ ID NO: 36:

(i) SEQUENCE CHARACTERISTICS:
        (A) LENGTH: 169
        (B) TYPE: nucleic acid
        (C) STRANDEDNESS: single
        (D) TOPOLOGY: linear (xi) SEQUENCE DESCRIPTION: SEQ ID NO: 36:

GATCTATGCT ACCTCTAGGG ATGGCACCAT TCACAAGCAC AAAGGAGATG TCAGTGATTA    60

AAAACACATG CTCTGGAGTC TGAGAGACTT TGAGACTTGC TAGCTTGTGA CTCTGCAGAG    120

TTTAAGGTAT CTGGACCCCT TTTTCCCTCA TGTGCATAAT GAAGAGATT               169

(2) INFORMATION FOR SEQ ID NO: 37:

(i) SEQUENCE CHARACTERISTICS:
        (A) LENGTH: 192
        (B) TYPE: nucleic acid
        (C) STRANDEDNESS: single
        (D) TOPOLOGY: linear (xi) SEQUENCE DESCRIPTION: SEQ ID NO: 37:

GATCAACACT GTTAGTTGAG TACCCACATC ACAAACGTGA TTCTCAGAAT GCCTTCCTTC    60

CTGTCTAGTT TCTATAGGTA GATATTTCCT TTTTCAGCAT AGGCCTGAAA AGCCGCCTCC    120

AAATGCCCGC CTTCCAGACA CTATAAAAAG AGGGTTCAAA CCTACTCTAT GAAAGGGAAT    180

GTTCAACACA GA                                                        192

(2) INFORMATION FOR SEQ ID NO: 38:

(i) SEQUENCE CHARACTERISTICS:
        (A) LENGTH: 157
        (B) TYPE: nucleic acid
        (C) STRANDEDNESS: single
        (D) TOPOLOGY: linear (ix) FEATURE:
        (D) OTHER INFORMATION:  The letter "N" stands for any base.

(xi) SEQUENCE DESCRIPTION: SEQ ID NO: 38:

GATCTGTTTA TTATTCTTCC AATATCTCCC CATCTCTTAA AAATTGGTTA TTTCTTCGTT    60

CATACATTTT TATCTCCCAA ATTANNNNTG AGACTGGTTT GAAGAGAGGA AAGCAATGTA    120

CACACTTTTA TATTCCACCA TGTATATCCG GATATCC                            157

(2) INFORMATION FOR SEQ ID NO: 39:

(i) SEQUENCE CHARACTERISTICS:
        (A) LENGTH: 135
        (B) TYPE: nucleic acid
        (C) STRANDEDNESS: single
        (D) TOPOLOGY: linear (xi) SEQUENCE DESCRIPTION: SEQ ID NO: 39:

AATCCTCCTA CCTTAACCTC CCTTTGTTAG CCTGCCATTA CAGGTGTGAG CCACCATTGC    60

TCATTCGTCC GTTTATTCAT TCAACAAATC AATCGATCTA TTACATGTGA GGGACTCTTC    120

AGGTCATGGG AATTC                                                    135

(2) INFORMATION FOR SEQ ID NO: 40:

(i) SEQUENCE CHARACTERISTICS:
        (A) LENGTH: 117
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO: 40:

```
GATCACTTGA GCCCAGGAGT TTGAGACCAG CCTGGGTGAC ATGGCAAAAC CCCATCTCTA      60

CCAAAAGAAA AAAANNNNAC AAATTGGTGG TGTTGATGGT CGGCGACCAT TGATCCC        117
```

(2) INFORMATION FOR SEQ ID NO: 41:

(i) SEQUENCE CHARACTERISTICS:
        (A) LENGTH: 137
        (B) TYPE: nucleic acid
        (C) STRANDEDNESS: single
        (D) TOPOLOGY: linear (xi) SEQUENCE DESCRIPTION: SEQ ID NO: 41:

```
GATCAGGGAG GGGCCGAAAA CTGGAGATGC AGGTGTGCTG TAAGACACTG CAGAGAGGGC      60

ATTTACCTGC CCCATCATCC AGCACAGGAA CAGCGACTGA CAGCGCTCAC CCACCCACCA     120

TCGCCAGTCA CACTGGG                                                    137
```

(2) INFORMATION FOR SEQ ID NO: 42:

(i) SEQUENCE CHARACTERISTICS:
        (A) LENGTH: 80
        (B) TYPE: nucleic acid
        (C) STRANDEDNESS: single
        (D) TOPOLOGY: linear (xi) SEQUENCE DESCRIPTION: SEQ ID NO: 42:

```
GGCTCGAGAA CGGGAGGAGG GGGCTCTTGT ATCAGGGCCC GTTGTCACAT CTGCTCTCAG      60

CTTGTTGAAA ACTCATAATC                                                  80
```

(2) INFORMATION FOR SEQ ID NO: 43:

(i) SEQUENCE CHARACTERISTICS:
        (A) LENGTH: 157
        (B) TYPE: nucleic acid
        (C) STRANDEDNESS: single
        (D) TOPOLOGY: linear (xi) SEQUENCE DESCRIPTION: SEQ ID NO: 43:

```
AGGTCCCTTG GTCGTGATCC GGGAAGGGGC CTGACGTTGC GGGAGATCGA GTTTTCTGTG      60

GGCTTGGGGA ACCTCTCACG TTGCTGTGTC CTGGTGAGCA GCCCGGACCA ATAAACCTGC     120

TTTTCTTAAA AGGAAAAAAA AAAAAAAAAA AAAAAAA                              157
```

(2) INFORMATION FOR SEQ ID NO: 44:

(i) SEQUENCE CHARACTERISTICS:
        (A) LENGTH: 120
        (B) TYPE: nucleic acid
        (C) STRANDEDNESS: single
        (D) TOPOLOGY: linear (xi) SEQUENCE DESCRIPTION: SEQ ID NO: 44:

```
ATCTAGGTTT TTTAAAAAAG CTTTGAGAGG TAATTACTTG CATATGAGAG AATAAAACAT      60
```

```
TTGGCACATT GTTAAAAAAA AAAAAAAAAA AAAAAAAAAA AAAAAAAAAA AAAAAAAAAA      120
```

(2) INFORMATION FOR SEQ ID NO: 45:

(i) SEQUENCE CHARACTERISTICS:
        (A) LENGTH: 149
        (B) TYPE: nucleic acid
        (C) STRANDEDNESS: single
        (D) TOPOLOGY: linear (xi) SEQUENCE DESCRIPTION: SEQ ID NO: 45:

```
CTCATTTACT TTTCTCTTAT AGCGTGGCTT TAAACATATA TACATTTGTA TATATGTATA       60

TATGAATATA ATGTATAAAA TGTATGTAGA TGTATATACA AAAAATAAAC GAGATGGGTT      120

AAAGATATGT AAAAAAAAAA AAAAAAAAA                                        149
```

(2) INFORMATION FOR SEQ ID NO: 46:

(i) SEQUENCE CHARACTERISTICS:
        (A) LENGTH: 142
        (B) TYPE: nucleic acid
        (C) STRANDEDNESS: single
        (D) TOPOLOGY: linear (xi) SEQUENCE DESCRIPTION: SEQ ID NO: 46:

```
AGTCCCAGCT ACTCGGGAGG GCTGAGGCAG GAGAATGGCG TGAACCCAGG AGGCGAAGCT       60

TGCAGTGAGC TGAGATCGCG CCACTGCACT CCAGCCTGGA CGACAGAGCG AGACTCTGTC      120

TCAAAAAAAA AAAAAAAAAA AA                                               142
```

(2) INFORMATION FOR SEQ ID NO: 47:

(i) SEQUENCE CHARACTERISTICS:
        (A) LENGTH: 7 base pairs
        (B) TYPE: nucleic acid
        (C) STRANDEDNESS: single
        (D) TOPOLOGY: linear (xi) SEQUENCE DESCRIPTION: SEQ ID NO: 47:

```
TGGTGTG                                                                  7
```

(2) INFORMATION FOR SEQ ID NO: 48:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (xi) SEQUENCE DESCRIPTION: SEQ ID NO: 48:

```
TGGTGTGTG                                                                9
```

(2) INFORMATION FOR SEQ ID NO: 49:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO: 49:

```
TGGTGTGTGT G                                                            11
```

(2) INFORMATION FOR SEQ ID NO: 50:

(i) SEQUENCE CHARACTERISTICS:

(A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO: 50:

TGGTGTGTGT GTG                                                              13

(2) INFORMATION FOR SEQ ID NO: 51:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 51:

TGGTGTGTGT GTGTG                                                            15

(2) INFORMATION FOR SEQ ID NO: 52:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (xi) SEQUENCE DESCRIPTION: SEQ ID NO: 52:

TGGGTG                                                                       6

(2) INFORMATION FOR SEQ ID NO: 53:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (xi) SEQUENCE DESCRIPTION: SEQ ID NO: 53:

TGGGTGTG                                                                     8

(2) INFORMATION FOR SEQ ID NO: 54:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 54:

TGGGTGTGTG                                                                  10

(2) INFORMATION FOR SEQ ID NO: 55:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO: 55:

TGGGTGTGTG TG                                                               12

(2) INFORMATION FOR SEQ ID NO: 56:

(i) SEQUENCE CHARACTERISTICS:
        (A) LENGTH: 14 base pairs

```
            (B) TYPE: nucleic acid
            (C) STRANDEDNESS: single
            (D) TOPOLOGY: linear (xi) SEQUENCE DESCRIPTION: SEQ ID NO: 56:

TGGGTGTGTG TGTG                                                    14

(2) INFORMATION FOR SEQ ID NO: 57:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (xi) SEQUENCE DESCRIPTION: SEQ ID NO: 57:

TGGGTGTGTG TGTGTG                                                  16

(2) INFORMATION FOR SEQ ID NO: 58:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 58:

TTGGGGTTGGGGTTG                                                    15

(2) INFORMATION FOR SEQ ID NO: 59:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO: 59:

GTGGCTTCACACAAAATCTAAGCGC                                          25

(2) INFORMATION FOR SEQ ID NO: 60:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (xi) SEQUENCE DESCRIPTION: SEQ ID NO: 60:

CCCTAACCCTAACCCT                                                   16

(2) INFORMATION FOR SEQ ID NO: 61:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO: 61:

CCCTAACCCTAACCCTAACC                                               20
```

SCREENING METHODS TO IDENTIFY INHIBITORS OF TELOMERASE ACTIVITY

This is a division of application Ser. No. 08/060,952, filed May 13, 1993; now U.S. Pat. No. 5,695,932 issued Dec. 9, 1997 hereby incorporated by reference herein in totality, including drawings.

This application is a continuation-in-part of Michael D. West et al., entitled "Therapy and diagnosis of conditions related to telomere length and/or telomerase activity, filed Mar. 24, 1993 and assigned U.S. Ser. No. 08/038,766, now U.S. Pat. No. 5,489,508 issued Feb. 6, 1996 which is a continuation-in-part of Michael D. West et al., entitled "Telomerase Activity Modulation and Telomere Diagnosis", filed May 13, 1992, and assigned U.S. Ser. No. 07/882,438, now abandoned both (including drawings) hereby incorporated by reference herein.

This invention relates to methods for therapy and diagnosis of cellular senescence and immortalization.

BACKGROUND OF THE INVENTION

The following is a general description of art relevant to the present invention. None is admitted to be prior art to the invention. Generally, this art relates to observations relating to cellular senescence, and theories or hypothesis which explain such aging and the mechanisms by which cells escape senescence and immortalize.

Normal human somatic cells (e.g., fibroblasts, endothelial, and epithelial cells) display a finite replicative capacity of 50–100 population doubling characterized by a cessation of proliferation in spite of the presence of abundant growth factors. This cessation of replication in vitro is variously referred to as cellular senescence or cellular aging, See, Goldstein, 249 Science 1129, 1990; Hayflick and Moorehead, 25 Exp. Cell Res. 585, 1961; Hayflick, ibid., 37:614, 1985; Ohno, 11 Mech. Aging Dev. 179, 1979; Ham and McKeehan, (1979) "Media and Growth Requirements", W. B. Jacoby and I. M. Pastan (eds), in: Methods in Enzymology, Academic Press, NY, 58:44–93. The replicative life span of cells is inversely proportional to the in vivo age of the donor (Martin et al., 23 Lab. Invest. 86, 1979; Goldstein et al., 64 Proc. Natl. Acad. Sci. USA 155, 1969; and Schneider and Mitsui, ibid., 73:3584, 1976), therefore cellular senescence is suggested to play an important role in aging in vivo.

Cellular immortalization (the acquisition of unlimited replicative capacity) may be thought of as an abnormal escape from cellular senescence, Shay et al., 196 Exp. Cell Res. 33, 1991. Normal human somatic cells appear to be mortal, i.e., have finite replicative potential. In contrast, the germ line and malignant tumor cells are immortal (have indefinite proliferative potential). Human cells cultured in vitro appear to require the aid of transforming viral oncoproteins to become immortal and even then the frequency of immortalization is $10^{-6}$ to $10^{-7}$. Shay and Wright, 184 Exp. Cell Res. 109, 1989. A variety of hypotheses have been advanced over the years to explain the causes of cellular senescence. While examples of such hypotheses are provided below, there appears to be no consensus or universally accepted hypothesis.

For example, the free radical theory of aging suggests that free radical-mediated damage to DNA and other macromolecules is causative in critical loss of cell function (Harmon, 11 J. Gerontol. 298, 1956; Harmon, 16 J. Gerontol. 247, 1961). Harman says (Harman, 78 Proc. Natl. Acad. Sci. 7124, 1981) "aging is largely due to free radical reaction damage . . . ."

Waste-product accumulation theories propose that the progressive accumulation of pigmented inclusion bodies (frequently referred to as lipofuscin) in aging cells gradually interferes with normal cell function (Strehler, 1 Adv. Geront. Res. 343, 1964; Bourne, 40 Prog. Brain Res. 187, 1973; Hayflick, 20 Exp. Gerontol. 145, 1985).

The gradual somatic mutation theories propose that the progressive accumulation of genetic damage to somatic cells by radiation and other means impairs cell function and that without the genetic recombination that occurs, for instance, during meiosis in the germ line cells, somatic cells lack the ability to proliferate indefinitely (Burnet, "Intrinsic Mutagenesis—A Genetic Approach to Aging", Wile, N.Y., 1976; Hayflick, 27 Exp. Gerontol. 363, 1992). Theories concerning genetically programmed senescence suggest that the expression of senescent-specific genes actively inhibit cell proliferation (Martin et al., 74 Am. J. Pathol. 137, 1974; Goldstein, 249 Science 1129, 1990).

Smith and Whitney, 207 Science 82, 1980, discuss a mechanism for cellular aging and state that their data is:

"compatible with the process of genetically controlled terminal differentiation . . . . The gradual decrease in proliferation potential would also be compatible with a continuous build up of damage or errors, a process that has been theorized. However, the wide variability in doubling potentials, especially in mitotic pairs, suggests an unequalled partitioning of damage or errors at division."

Shay et al., 27 Experimental Gerontology 477, 1992, and 196 Exp. Cell Res. 33, 1991 describe a two-stage model for human cell mortality to explain the ability of Simian Virus 40 T-antigen to immortalize human cells. The mortality stage 1 mechanism (M1) is the target of certain tumor virus proteins, and an independent mortality stage 2 mechanism (M2) produces crisis and prevents these tumor viruses from directly immortalizing human cells. The authors utilized T-antigen driven by a mouse mammary tumor virus promoter to cause reversible immortalization of cells. The Simian Virus 40 T-antigen is said to extend the replicative life span of human fibroblast by an additional 40–60%. The authors postulate that the M1 mechanism is overcome by T-antigen binding to various cellular proteins, or inducing new activities to repress the M1 mortality mechanism. The M2 mechanism then causes cessation of proliferation, even though the M1 mechanism is blocked. Immortality is achieved only when the M2 mortality mechanism is also disrupted.

It has also been proposed that the finite replicative capacity of cells may reflect the work of a "clock" liked to DNA synthesis in the telomere (end part) of the chromosomes. Olovnikov, 41 J. Theoretical Biology 181, 1973, describes the theory of marginotomy to explain the limitations of cell doubling potential in somatic cells. He states that an:

"informative oligonucleotide, built into DNA after a telogene and controlling synthesis of a repressor of differentiation, might serve as a means of counting mitosis performed in the course of morphogenesis. Marginotomic elimination of such an oligonucleotide would present an appropriate signal for the beginning of further differentiation. Lengthening of the telogene would increase the number of possible mitoses in differentiation."

Harley et al., 345 Nature 458, 1990, state that the amount and length of telomeric DNA in human fibroblasts decreases as a function of serial passage during aging in vitro, and possibly in vivo, but do not know whether this loss of DNA has a causal role in senescence. They also state:

"Tumour cells are also characterized by shortened telomeres and increased frequency of aneuploidy, including telomeric associations. If loss of telomeric DNA ultimately causes cell-cycle arrest in normal cells, the final steps in this process may be blocked in immortalized cells. Whereas normal cells with relatively long telomeres and a senescent phenotype may contain little or no telomerase activity, tumour cells with short telomeres may have significant telomerase activity. Telomerase may therefore be an effective target for anti-tumour drugs.

There are a number of possible mechanisms for loss of telomeric DNA during ageing, including incomplete replication, degradation of termini (specific or nonspecific), and unequal recombination coupled to selection of cells with shorter telomeres. Two features of our data are relevant to this question. First, the decrease in mean telomere length is about 50 bp per mean population doubling and, second, the distribution does not change substantially with growth state or cell arrest. These data are most easily explained by incomplete copying of the template strands at their 3' termini. But the absence of detailed information about the mode of replication or degree of recombination at telomeres means that none of these mechanisms can be ruled out. Further research is required to determine the mechanism of telomere shortening in human fibroblasts and its significance to cellular senescence." [Citations omitted.]

Hastie et al., 346 *Nature* 866, 1990, while discussing colon tumor cells, state that:

"[T]here is a reduction in the length of telomere repeat arrays relative to the normal colonic mucosa from the same patient.

Firm figures are not available, but it is likely that the tissues of a developed fetus result from 20–50 cell divisions, whereas several hundred or thousands of divisions have produced the colonic mucosa and blood cells of 60-year old individuals. Thus the degree of telomere reduction is more or less proportional to the number of cell divisions. It has been shown that the ends of Drosophila chromosomes without normal telomeres reduce in size by 4 base pairs (bp) per cell division and that the ends of yeast chromosomes reduce by a similar degree in a mutant presumed to lack telomerase function. If we assume the same rate of reduction is occurring during somatic division in human tissues, then a reduction in TRA by 14 kb would mean that 3,500 ancestral cell divisions lead to the production of cells in the blood of a 60-year old individual; using estimates of sperm telomere length found elsewhere we obtain a value of 1,000–2,000. These values compare favourably with those postulated for mouse blood cells. Thus, we propose that telomerase is indeed lacking in somatic tissues. In this regard it is of interest to note that in maize, broken chromosomes are only healed in sporophytic (zygotic) tissues and not in endosperm (terminally differentiated), suggesting that telomerase activity is lacking in the differentiated tissues." [Citations omitted.]

The authors propose that in some tumors telomerase is reactivated, as proposed for HeLa cells in culture, which are known to contain telomerase activity. But, they state:

"One alternative explanation for our observations is that in tumours the cells with shorter telomeres have a growth advantage over those with larger telomeres, a situation described for vegetative cells of tetrahymena." [Citations omitted.]

Harley, 256 *Mutation Research* 271, 1991, discusses observations allegedly showing that telomeres of human somatic cells act as a mitotic clock shortening with age both in vitro and in vivo in a replication dependent manner. He states:

"Telomerase activation may be a late, obligate event in immortalization since many transformed cells and tumour tissues have critically short telomeres. Thus, telomere length and telomerase activity appear to be markers of the replicative history and proliferative potential of cells; the intriguing possibility remains that telomere loss is a genetic time bomb and hence causally involved in cell senescence and immortalization.

Despite apparently stable telomere length in various tumour tissues or transformed cell lines, this length was usually found to be shorter than those of the tissue of origin. These data suggest that telomerase becomes activated as a late event in cell transformation, and that cells could be viable (albeit genetically unstable) with short telomeres stably maintained by telomerase. If telomerase was constitutively present in a small fraction of normal cells, and these were the ones which survived crisis or became transformed, we would expect to find a greater frequency of transformed cells with long telomeres." [Citations omitted.]

He proposes a hypothesis for human cell aging and transformation as "[a] semi-quantitative model in which telomeres and telomerase play a causal role in cell senescence and cancer" and proposes a model for this hypothesis.

De Lange et al., 10 *Molecular and Cellular Biology* 518, 1990, generally discuss the structure of human chromosome ends or telomeres. They state:

"we do not know whether telomere reduction is strictly coupled to cellular proliferation. If the diminution results from incomplete replication of the telomere, such a coupling would be expected; however, other mechanisms, such as exonucleolytic degradation, may operate independent of cell division. In any event, it is clear that the maintenance of telomeres is impaired in somatic cells. An obvious candidate activity that may be reduced or lacking is telomerase. A human telomerase activity that can add TTAGGG repeats to G-rich primers has recently been identified (G. Morin, personal communication). Interestingly, the activity was demonstrated in extracts of HeLa cells, which we found to have exceptionally long telomeres. Other cell types have not been tested yet, but such experiments could now establish whether telomerase activity is (in part) responsible for the dynamics of human chromosome ends."

Starling et al., 18 *Nucleic Acids Research* 6881, 1990, indicate that mice have large telomeres and discusses this length in relationship to human telomeres. They state:

"Recently it has been shown that there is reduction in TRA length with passage number of human fibroblasts in vitro and that cells in a senescent population may lack telomeres at some ends altogether. Thus in vitro, telomere loss may play a role in senescence, a scenario for which there is evidence in *S. cerevisae* and Tetrahymena. Some of the mice we have been studying are old in mouse terms, one and a half years, yet they still have TRA's greater than 30 kb in all tissues studied. In humans, telomeres shorten with age at a rate of 100 bp per year, hence, it is conceivable that the same is happening in the mouse, but the removal of a few 100 bps of terminal DNA during its lifetime would not be detectable." [Citations omitted.]

D'Mello and Jazwinski, 173 *J. Bacteriology* 6709, 1991, state:

"We propose that during the life span of an organism, telomere shortening does not play a role in the normal aging process. However, mutations or epigenetic changes that affect the activity of the telomerase, like any other genetic change, might affect the life span of the individual in which they occur.

In summary, the telomere shortening with age observed in human diploid fibroblasts may not be a universal phenomenon. Further studies are required to examine telomere length and telomerase activity not only in different cell types as they age but also in the same cell type in different organisms with differing life spans. This would indicate whether telomere shortening plays a causal role in the senescence of a particular cell type or organism."

Hiyama et al., 83 *Jpn. J. Cancer Res.* 159, 1992, provide findings that "suggest that the reduction of telomeric repeats is related to the proliferative activity of neuroblastoma cells and seems to be a useful indicator of the aggressiveness of neuroblastoma . . . . Although we do not know the mechanism of the reduction and the elongation of telomeric repeats in neuroblastoma, we can at least say that the length of telomeric repeats may be related to the progression and/or regression of neuroblastoma."

Counter et al., 11 *EMBO J.* 1921, 1992, state "loss of telomeric DNA during cell proliferation may play a role in ageing and cancer." They propose that the expression of telomerase is one of the events required for a cell to acquire immortality and note that:

This model may have direct relevance to tumourigenesis in vivo. For example, the finite lifespan of partially transformed (pre-immortal) cells which lack telomerase might explain the frequent regression of tumours after limited growth in vivo. In bypassing the checkpoint representing normal replicative senescence, transformation may confer an additional 20–40 population doubling during which an additional ≈2 kbp of telomeric DNA is lost. Since 20 40 doubling ($10^6$–$10^{12}$ cells in a clonal population) potentially represents a wide range of tumour sizes, it is possible that many benign tumours may lack telomerase and naturally regress when telomeres become critically shortened. We predict that more aggressive, perhaps metastatic tumours would contain immortal cells which express telomerase. To test this hypothesis, we are currently attempting to detect telomerase in a variety of tumour tissues and to correlate activity with proliferative potential. Anti-telomerase drugs or mechanisms to repress telomerase expression could be effective agents against tumours which depend upon the enzyme for maintenance of telomeres and continued cell growth.

Levy et al., 225 *J. Mol. Biol.* 951, 1992, state that:

"Although it has not been proven that telomere loss contributes to senescence of multicellular organisms, several lines of evidence suggest a causal relationship may exist.

It is also possible that telomere loss with age is significant in humans, but not in mice." [Citations omitted.]

Windle and McGuire, 33 *Proceedings of the American Association for Cancer Research* 594, 1992, discuss the role of telomeres and state that:

"These and other telomere studies point in a new direction regarding therapeutic targets and strategies to combat cancer. If the cell can heal broken chromosomes preventing genomic disaster, then there may be a way to facilitate or artificially create this process. This could even provide a preventive means of stopping cancer which could be particularly applicable in high risk patients. The difference in telomere length in normal versus tumor cells also suggests a strategy where the loss of telomeres is accelerated. Those cells with the shortest telomeres, such as those of tumor metastasis would be the most susceptible."

Goldstein, 249 *Science* 1129, 1990, discusses various theories of cellular senescence including that of attrition of telomeres. He states:

"However, such a mechanism is not easily reconciled with the dominance of senescent HDF over young HDF in fusion hybrids, particularly in short-term heterokaryons. One could again invoke the concept of dependence and the RAD9 gene example, such that complete loss of one or a few telomeres leads to the elaboration of a negative signal that prevents initiation of DNA synthesis, thereby mimicking the differentiated state. This idea, although speculative, would not only explain senescent replicative arrest but also the chromosomal aberrations observed in senescent HDS that would specifically ensue after loss of telomeres." [Citations omitted.]

The role of telomere loss in cancer is further discussed by Jankovic et al. and Hastie et al., both at 350 *Nature* 1991, in which Jankovic indicates that telomere shortening is unlikely to significantly influence carcinogenesis in men and mice. Hastie et al. agree that if telomere reduction does indeed reflect cell turnover, this phenomenon is unlikely to play a role in pediatric tumors, and those of the central nervous system. Hastie et al., however, feel "our most original and interesting conclusion was that telomere loss may reflect the number of cell division in a tissue history, constituting a type of clock."

Kipling and Cooke, 1 *Human Molecular Genetics* 3, 1992, state:

"It has been known for some years that telomeres in human germline cells (e.g. sperm) are longer than those in somatic tissue such as blood. One proposed explanation for this is the absence of telomere repeat addition (i.e. absence of telomerase activity) in somatic cells. If so, incomplete end replication would be expected to result in the progressive loss of terminal repeats as somatic cells undergo successive rounds of division. This is indeed what appears to happen in vivo for humans, with both blood and skin cells showing shorter telomeres with increasing donor age, and telomere loss may contribute to the chromosome aberrations typically seen in senescent cells. Senescence and the measurement of cellular time is an intriguingly complex subject and it will be interesting to see to what extent telomere shortening has a causal role. The large telomeres possessed by both young and old mice would seem to preclude a simple relationship between telomere loss and ageing, but more elaborate schemes cannot be ruled out." [Citations omitted.]

Greider, 12 *BioEssays* 363, 1990, provides a review of the relationship between telomeres, telomerase, and senescence. She indicates that telomerase contains an RNA component which provides a template for telomere repeat synthesis. She notes that an oligonucleotide "which is complementary to the RNA up to and including the CAACCCCAA sequence, competes with d(TTGGGG)n primers and inhibits telomerase in vitro" (citing Greider and Blackburn, 337 *Nature* 331, 1989). She also describes experiments which she believes "provide direct evidence that telomerase is involved in telomere synthesis in vivo." She goes on to state:

"Telomeric restriction fragments in many transformed cell lines are much shorter than those in somatic cells. In addition, telomere length in tumor tissues is significantly shorter than in the adjacent non-tumor tissue. When transformed cell lines are passaged in vitro there is no change in telomere length. Thus if untransformed cells lack the ability to maintain a telomere length equilibrium, most transformed cells appear to regain it and to reset the equilibrium telomere length to a size shorter than seen in most tissues in vivo. The simplest interpretation of these data is that enzymes, such as telomerase, involved in maintaining telomere length may be required for growth of transformed cells and not required for normal somatic cell viability. This suggests that telomerase may be a good target for anti-tumor drugs." [Citations omitted.]

Blackburn, 350 *Nature* 569, 1991, discusses the potential for drug action at telomeres stating:

"The G-rich strand of the telomere is the only essential chromosomal DNA sequence known to be synthesized by the copying of a separate RNA sequence. This unique mode of synthesis, and the special structure and behavior of telomeric DNA, suggest that telomere synthesis could be a target for selective drug action. Because telomerase activity seems to be essential for protozoans or yeast, but not apparently for mammalian somatic cells, I propose that telomerase should be explored as a target for drugs against eukaryotic pathogenic or parasitic microorganisms, such as parasitic protozoans or pathogenic yeasts. A drug that binds telomerase selectively, either through its reverse-transcriptase or DNA substrate-binding properties, should selectively act against prolonged maintenance of the dividing lower eukaryote, but not impair the mammalian host over the short term, because telomerase activity in its somatic cells may normally be low or absent. Obvious classes of drugs to investigate are those directed specifically against reverse transcriptases as opposed to other DNA or RNA polymerases, and drugs that would bind telomeric DNA itself. These could include drugs that selectively bind the G°G base-paired forms of the G-rich strand protrusions at the chromosome termini, or agents which stabilize an inappropriate G°G base-paired form, preventing it from adopting a structure necessary for proper function in vivo. Telomeres have been described as the Achilles heel of chromosomes: perhaps it is there that drug strategies should now be aimed." [Citations omitted.]

Lundblad and Blackburn, 73 *Cell* 347, 1993, discuss alternative pathways for maintainance of yeast telomers, and state that:

". . . the work presented in this paper demonstrates that a defect in telomere replication need not result in the death of all cells in a population, suggesting that telomere loss and its relationship to mammalian cellular senescence may have to be examined further."

Other review articles concerning telomeres include Blackburn and Szostak, 53 *Ann. Rev. Biochem.* 163, 1984; Blackburn, 350 *Nature* 569, 1991; Greider, 67 *Cell* 645, 1991, and Moyzis 265 *Scientific American* 48, 1991. Relevant articles on various aspects of telomeres include Cooke and Smith, *Cold Spring Harbor Symposia on Quantitative Biology* Vol. LI, pp. 213–219; Morin, 59 *Cell* 521, 1989; Blackburn et al., 31 *Genome* 553, 1989; Szostak, 337 *Nature* 303, 1989; Gall, 344 *Nature* 108, 1990; Henderson et al., 29 *Biochemistry* 732, 1990; Gottschling et al., 63 *Cell* 751, 1990; Harrington and Grieder, 353 *Nature* 451, 1991; Muller et al., 67 *Cell* 815, 1991; Yu and Blackburn, 67 *Cell* 823, 1991; and Gray et al., 67 *Cell* 807, 1991. Other articles or discussions of some relevance include Lundblad and Szostak, 57 *Cell* 633, 1989; and Yu et al., 344 *Nature* 126, 1990.

SUMMARY OF THE INVENTION

This invention concerns methods for therapy and diagnosis of cellular senescence and immortalization utilizing techniques associated with control of telomere length and telomerase activity. Therapeutic strategies of this invention include reducing the rate or absolute amount of telomere repeat length loss or increasing the telomere repeat length during cell proliferation, thereby providing for the postponement of cellular senescence and reducing the level of chromosomal fusions and other chromosomal aberrations. In addition, inhibition of telomerase activity in vivo or in vitro may be used to control diseases associated with cell immortality, such as neoplasia, and pathogenic parasites.

Applicant has determined that the inhibition of telomere shortening in a cell in vitro is causally related to increasing the length of the replicative lifespan of that cell. Applicant has also determined that inhibition of telomerase activity in a cell in vitro is causally related to reducing the ability of that cell to proliferate in an immortal manner. Thus, applicant is the first to provide data which clearly indicates that inhibition of telomere shortening in vivo or in vitro, and that inhibition of telomerase activity in vivo or in vitro, is therapeutically beneficial. Prior to applicant's experiments, as indicated above, there was no consensus by those in the art that one could predict that such experiments would provide the data observed by applicant, or that such manipulations would have therapeutic utility.

The invention also concerns the determination of cellular status by diagnostic techniques that analyze telomere length and telomerase activity, as a diagnostic of cellular capacity for proliferation. Assays for telomere length are performed to provide useful information on the relative age and remaining proliferative capability of a wide variety of cell types in numerous tissues. Sequences are also described from the telomeres of budding yeasts which are highly variable from strain to strain and provide sequences for oligonucleotide probes that would enable the rapid identification of yeast strains, and in the case of human and veterinary pathogens, the diagnosis of the strain of the pathogen.

Telomerase activity and the presence of the enzyme is used as a marker for diagnosing and staging neoplasia and detecting pathogenic parasites. Applicant's experiments have, for the first time, determined a correlation between telomerase activity and the tumor cell phenotype, as well as a correlation between telomere length and the in vivo aged status of cells. As noted above, there was no consensus in the art that one could predict that such a relationship existed. In contrast, applicant has defined this relationship, and thus has now defined useful diagnostic tools by which to determine useful clinical data. Such data can be used to define a therapeutic protocol, or the futility of such a protocol.

Thus, in a first aspect, the invention features methods for the treatment of a condition associated with cellular senescence or increased rate of proliferation of a cell (e.g., telomere repeat loss associated with cell proliferation in the absence of telomerase). A first method involves administering to the cell a therapeutically effective amount of an agent active to reduce loss of telomeric repeats during its proliferation. Such therapeutics may be especially applicable to conditions of increased rate of cell proliferation.

By "increased rate of proliferation" of a cell is meant that the cell has a higher rate of cell division compared to normal cells of that cell type, or compared to normal cells within other individuals of that cell type. Examples of such cells include the $CD4^+$ cells of HIV-infected individuals (see example below), connective tissue fibroblasts associated with degenerative joint diseases, age-related macular degeneration, astrocytes associated with Alzheimer's Disease and endothelial cells associated with atherosclerosis (see example below). In each case, one particular type of cell or a group of cells is found to be replicating at an increased level compared to surrounding cells in those tissues, or compared to normal individuals, e.g., individuals not infected with the HIV virus. Thus, the invention features administering to those cells an agent which reduces loss of telomere length in those cells while they proliferate. The agent itself need not slow the proliferation process, but rather allow that proliferation process to continue for more cell divisions than would be observed in the absence of the agent. The agent may also be useful to slow telomere repeat loss occurring during normal aging (wherein the cells are proliferating at a normal rate and undergoing senescence late in life), and for reducing telomere repeat loss while expanding cell number ex vivo for cell-based therapies, e.g., bone marrow transplantation following gene therapy.

As described herein, useful agents can be readily identified by those of ordinary skill in the art using routine screening procedures. For example, a particular cell having a known telomere length is chosen and allowed to proliferate, and the length of telomere is measured during proliferation. Agents which are shown to reduce the loss of telomere length during such proliferation are useful in this invention. Particular examples of such agents are provided below. For example, oligonucleotides which are able to promote synthesis of DNA at the telomere ends are useful in this invention. In addition, telomerase may be added to a cell either by gene therapy techniques, or by of the enzyme or its equivalent into a cell administration, e.g., by injection or lipojection.

A second method for the treatment of cellular senescence involves the use of an agent to derepress telomerase in cells where the enzyme is normally repressed. Telomerase activity is not detectable in any normal human somatic cells, but is detectable in cells that have abnormally reactivated the enzyme during the transformation of a normal cell into an immortal tumor cell. Telomerase activity may therefore be appropriate only in germ line cells and some stem cell populations (though there is currently no evidence of the latter in human tissues). Since the loss of telomeric repeats leading to senescence in somatic cells is occuring due to the absence of adequate telomerase activity, agents that have the effect of activating telomerase would have the effect of adding arrays of telomeric repeats to telomeres, thereby imparting to mortal somatic cells increased replicative capacity, and imparting to senescent cells the ability to proliferate and appropriately exit the cell cycle (in the absence of growth factor stimulation with associated appropriate regulation of cell cycle-linked genes typically inappropriately expressed in senescence e.g., collagenase, urokinase, and other secreted proteases and protease inhibitors). Such factors to derepress telomerase may be administered transiently or chronically to increase telomere length, and then removed, thereby allowing the somatic cells to again repress the expression of the enzyme utilizing the natural mechanisms of repression.

Such activators of telomerase may be found by screening techniques utilizing human cells that have the M1 mechanism of senescence abrogated by means of the expression of SV40 T-antigen. Such cells when grown to crisis, wherein the M2 mechanism is preventing their growth, will proliferate in response to agents that derepress telomerase. Such activity can be scored as the incorporation of radiolabeled nucleotides or proliferating clones can be selected for in a colony forming assay.

Such activators of telomerase would be useful as therapeutic agents to forestall and reverse cellular senescence, including but not limited to conditions associated with cellular senescence, e.g., (a) cells with replicative capacity in the central nervous system, including astrocytes, endothelial cells, and fibroblasts which play a role in such age-related diseases as Alzheimer's disease, Parkinson's disease, Huntington's disease, and stroke, (b) cells with finite replicative capacity in the integument, including fibroblasts, sebaceous gland cells, melanocytes, keratinocytes, Langerhan's cells, and hair follicle cells which may play a role in age-related diseases of the integument such as dermal atrophy, elastolysis and skin wrinkling, sebaceous gland hyperplasia, senile lentigo, graying of hair and hair loss, chronic skin ulcers, and age-related impairment of wound healing, (c) cells with finite replicative capacity in the articular cartilage, such as chondrocytes and lacunal and synovial fibroblasts which play a role in degenerative joint disease, (d) cells with finite replicative capacity in the bone, such as osteoblasts and osteoprogenitor cells which play a role in osteoporosis, (e) cells with finite replicative capacity in the immune system such as B and T lymphocytes, monocytes, neutrophils, eosinophils, basophils, NK cells and their respective progenitors, which may play a role in age-related immune system impairment, (f) cells with a finite replicative capacity in the vascular system including endothelial cells, smooth muscle cells, and adventitial fibroblasts which may play a role in age-related diseases of the vascular system including atherosclerosis, calcification, thrombosis, and aneurysms, and (g) cells with a finite replicative capacity in the eye such as pigmented epithelium and vascular endothelial cells which may play an important role in age-related macular degeneration.

In a second aspect, the invention features a method for treatment of a condition associated with an elevated level of telomerase activity within a cell. The method involves administering to that cell a therapeutically effective amount of an inhibitor of telomerase activity.

The level of telomerase activity can be measured as described below, or by any other existing methods or equivalent methods. By "elevated level" of such activity is meant that the absolute level of telomerase activity in the particular cell is elevated compared to normal cells in that individual, or compared to normal cells in other individuals not suffering from the condition. Examples of such conditions include cancerous condition. Examples of such associated with the presence of cells which are not normally present in that individual, such as protozoan parasites or opportunistic pathogens, which require telomerase activity for their continued replication. Administration of an inhibitor can be achieved by any desired means well known to those of ordinary skill in the art.

In addition, the term "therapeutically effective amount" of an inhibitor is a well recognized phrase. The amount actually applied will be dependent upon the individual or animal to which treatment is to be applied, and will preferably be an optimized amount such that an inhibitory effect is achieved without significant side-effects (to the extent that those can be avoided by use of the inhibitor). That is, if effective inhibition can be achieved with no side-effects with the inhibitor at a certain concentration, that concentration should be used as opposed to a higher concentration at which side-effects may become evident. If side-effects are unavoidable, however, the minimum amount of inhibitor that is necessary to achieve the inhibition desired may have to be used.

By "inhibitor" is simply meant any reagent, drug or chemical which is able to inhibit a telomerase activity in vitro or in vivo. Such inhibitors can be readily identified using standard screening protocols in which a cellular extract or other preparation having telomerase activity is placed in contact with a potential inhibitor, and the level of telomerase activity measured in the presence or absence of the inhibitor, or in the presence of varying amounts of inhibitor. In this way, not only can useful inhibitors be identified, but the optimum level of such an inhibitor can be determined in vitro for further testing in vivo.

One example of a suitable telomerase inhibitor assay is carried out in 96-well microtiter plates. One microtiter plate is used to make dilutions of the test compounds, while another plate is used for the actual assay. Duplicate reactions of each sample are performed. A mixture is made containing the appropriate amount of buffer, template oligonucleotide, and Tetrahymena or human telomerase extract for the number of the samples to be tested, and aliquots are placed in the assay plate. The test compounds are added individually and the plates are pre-incubated at 30° C. $^{32}$P-dGTP is then added and the reaction allowed to proceed for 10 minutes at 30° C. The total volume of each reaction is 10 $\mu$l. The reaction is then terminated by addition of Tris and EDTA, and half the volume (5 $\mu$l) spotted onto DE81 filter paper. The samples are allowed to air dry, and the filter paper is rinsed in 0.5 M NaPhosphate several times to wash away the unincorporated labeled nucleotide. After drying, the filter paper is exposed to a phosphor imaging plate and the amount of signal quantitated. By comparing the amount of signal for each of the test samples to control samples, the percent of inhibition can be determined.

In addition, a large number of potentially useful inhibitors can be screened in a single test, since it is inhibition of telomerase activity that is desired. Thus, if a panel of 1,000 inhibitors is to be screened, all 1,000 inhibitors can potentially be placed into microtiter wells. If such an inhibitor is discovered, then the pool of 1,000 can be subdivided into 10 pools of 100 and the process repeated until an individual inhibitor is identified. As discussed herein, one particularly useful set of inhibitors includes oligonucleotides which are able to either bind with the RNA present in telomerase or able to prevent binding of that RNA to its DNA target or one of the telomerase protein components. Even more preferred are those oligonucleotides which cause inactivation or cleavage of the RNA present in a telomerase. That is, the oligonucleotide is chemically modified or has enzyme activity which causes such cleavage. The above screening may include screening of a pool of many different such oligonucleotide sequences.

In addition, a large number of potentially useful compounds can be screened in extracts from natural products. Sources of such extracts can be from a large number of species of fungi, actinomyces, algae, protozoa, plants, and bacteria. Those extracts showing inhibitory activity can then be analyzed to isolate the active molecule.

In related aspects, the invention features pharmaceutical compositions which include therapeutically effective amounts of the inhibitors or agents described above, in pharmaceutically acceptable buffers much as described below. These pharmaceutical compositions may include one or more of these inhibitors or agents, and be co-administered with other drugs. For example, AZT is commonly used for treatment of HIV, and may be co-administered with an inhibitor or agent of the present invention.

In a related aspect, the invention features a method for extending the ability of a cell to replicate. In this method, a replication extending amount of an agent which is active to reduce loss of telomere length within the cell is provided during cell replication. As will be evident to those of ordinary skill in the art, this agent is similar to that useful for treatment of a condition associated with an increased rate of proliferation of a cell. However, this method is useful for the treatment of individuals not suffering from any particular condition, but in which one or more cell types are limiting in that patient, and whose life can be extended by extending the ability of those cells to continue replication. That is, the agent is added to delay the onset of cell senescence characterized by the inability of that cell to replicate further in an individual. One example of such a group of cells includes lymphocytes present in patients suffering from Downs Syndrome (although treatment of such cells may also be useful in individuals not identified as suffering from any particular condition or disease, but simply recognizing that one or more cells, or collections of cells are becoming limiting in the life span of that individual).

It is notable that administration of such inhibitors or agents is not expected to be detrimental to any particular individual. However, should gene therapy be used to introduce a telomerase into any particular cell population, or other means be used to reversibly de-repress telomerase activity in somatic cells, care should be taken to ensure that the activity of that telomerase is carefully regulated, for example, by use of a promoter which can be regulated by the nutrition of the patient. Thus, for example, the promoter may only be activated when the patient eats a particular nutrient, and is otherwise inactive. In this way, should the cell population become malignant, that individual may readily inactivate telomerase of the cell and cause it to become mortal simply by no longer eating that nutrient.

In a further aspect, the invention features a method for diagnosis of a condition in a patient associated with an elevated level of telomerase activity within a cell. The method involves determining the presence or amount of telomerase within the cells in that patient.

In yet another aspect, the invention features a method for diagnosis of a condition associated with an increased rate of proliferation in that cell in an individual. Specifically, the method involves determining the length of telomeres within the cell.

The various conditions for which diagnosis is possible are described above. As will be exemplified below, many methods exist for measuring the presence or amount of telomerase within a cell in a patient, and for determining the length of telomeres within the cell. It will be evident that the presence or amount of telomerase may be determined within an individual cell, and for any particular telomerase activity (whether it be caused by one particular enzyme or a plurality of enzymes). Those in the art can readily formulate antibodies or their equivalent to distinguish between each type of telomerase present within a cell, or within an individual. In addition, the length of telomeres can be determined as an average length, or as a range of lengths much as described below. Each of these measurements will give precise information regarding the status of any particular individual.

Thus, applicant's invention has two prongs—a diagnostic and a therapeutic prong. These will now be discussed in detail.

The therapeutic prong of the invention is related to the now clear observation that the ability of a cell to remain immortal lies in the ability of that cell to maintain or increase the telomere length of chromosomes within that cell. Such a telomere length can be maintained by the presence of sufficient activity of telomerase, or an equivalent enzyme, within the cell. Thus, therapeutic approaches to reducing the potential of a cell to remain immortal focus on the inhibition of telomerase activity within those cells in which it is desirable to cause cell death. Examples of such cells include cancerous cells, which are one example of somatic cells which have regained the ability to express telomerase, and have become immortal. Applicant has now shown that such cells can be made mortal once more by inhibition of telomerase activity. As such, inhibition can be achieved in a multitude of ways including, as illustrated below, the use of oligonucleotides which, in some manner, block the ability of telomerase to extend telomeres in vivo.

Thus, oligonucleotides can be designed either to bind to a telomere (to block the ability of telomerase to bind to that telomere, and thereby extend that telomere), or to bind to the resident oligonucleotide (RNA) present in telomerase to thereby block telomerase activity on any nucleic acid (telomere). Such oligonucleotides may be formed from naturally occurring nucleotides, or may include modified nucleotides to either increase the stability of the therapeutic agent, or cause permanent inactivation of the telomerase, e.g., the positioning of a chain terminating nucleotide at the 3' end of the molecule of a nucleotide with a reactive group capable of forming a covalent bond with telomerase. Such molecules may also include ribozyme sequences. In addition, non-oligonucleotide based therapies can be readily devised by screening for those molecules which have an ability to inhibit telomerase activity in vitro, and then using those molecules in vivo. Such a screen is readily performed and will provide a large number of useful therapeutic molecules. These molecules may be used for treatment of cancers, of any type, including solid tumors and leukemias (including those in which cells are immortalized, including: apudoma, choristoma, branchioma, malignant carcinoid syndrome, carcinoid heart disease, carcinoma (e.g., Walker, basal cell, basosquamous, Brown-Pearce, ductal, Ehrlich tumor, in situ, Krebs 2, merkel cell, mucinous, non-small cell lung, oat cell, papillary, scirrhous, bronchiolar, bronchogenic, squamous cell, and transitional cell), histiocytic disorders, leukemia (e.g., b-cell, mixed-cell, null-cell, T-cell, T-cell chronic, HTLV-II-associated, lyphocytic acute, lymphocytic chronic, mast-cell, and myeloid), histiocytosis malignant, Hodgkin's disease, immunoproliferative small, non-Hodgkin's lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing's sarcoma, synovioma, adenofibroma, adenolymphoma, carcinosarcoma, chordoma, craniopharyngioma, dysgerminoma, hamartoma, mesenchymoma, mesonephroma, myosarcoma, ameloblastoma, cementoma, odontoma, teratoma, thymoma, trophoblastic tumor, adenocarcinoma, adenoma, cholangioma, cholesteatoma, cylindroma, cystadenocarcinoma, cystadenoma, granulosa cell tumor, gynandroblastoma, hepatoma, hidradenoma, islet cell tumor, leydig cell tumor, papilloma, sertoli cell tumor, theca cell tumor, leiomyoma, leiomyosarcoma, myoblastoma, myoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcomaphyllodes, fibrosarcoma, hemangiosarcoma, leiomyosarcoma, leukosarcoma, liposarcoma, lymphangiosarcoma, myosarcoma, myxosarcoma, ovarian carcinoma, rhabdomyosarcoma, sarcoma (e.g., Ewing's, experimental, Kaposi's, and mast-cell), neoplasms (e.g., bone, breast, digestive system, colorectal, liver, pancreatic, pituitary, testicular, orbital, head and neck, central nervous system, acoustic, pelvic, respiratory tract, and urogenital), neurofibromatosis, and cervical dysplasia), and for treatment of other conditions in which cells have become immortalized.

Applicant has also determined that it is important to slow the loss of telomere sequences, in particular, cells in association with certain diseases (although such treatment is not limited to this, and can be used in normal aging and ex vivo treatments). For example, some diseases are manifest by the abnormally fast rate of proliferation of one or more particular groups of cells. Applicant has determined that it is the senescence of those groups of cells at an abnormally early age (compared to the age of the patient), that eventually leads to death of that patient. One example of such a disease is AIDS, in which death is caused by the early senescence of $CD4^+$ cells. It is important to note that such cells age, not because of abnormal loss of telomere sequences (although this may be a factor), but rather because the replicative rate of the $CD4^+$ cells is increased such that telomere attrition is caused at a greater rate than normal for that group of cells. Thus, applicant provides therapeutic agents which can be used for treatment of such diseases, and also provides a related diagnostic procedure by which similar diseases can be detected so that appropriate therapeutic protocols can be devised and followed.

Specifically, the loss of telomeres within any particular cell population can be reduced by provision of an oligonucleotide which reduces the extent of telomere attrition during cell division, and thus increases the number of cell divisions that may occur before a cell becomes senescent. Other reagents, for example, telomerase, may be provided within a cell in order to reduce telomere loss, or to make that cell immortal. Those of ordinary skill in the art will recognize that other enzymatic activities may be used to enhance the lengthening of telomeres within such cells, for example, by providing certain viral sequences which activate telomerase or can otherwise function to synthesize telomere sequences within a cell. In addition, equivalent such molecules, or other molecules may be readily screened to determine those that will reduce loss of telomeres. Such screens may occur in vitro, and the therapeutic agents discovered by such screening utilized in the above method in vivo.

Other therapeutic treatments relate to the finding of unusual telomeric DNA sequences in a group of fungi, specifically a group of budding yeasts that includes some pathogens—*Candida albicans, Candida tropicalis* and *Candida oaratrorpicalis*—as well as nonpathogenic fungi. These results are described in more detail below. Drugs or chemical agents can be used to specifically exploit the unusual nature of the telomeric DNA of fungi. This includes the introduction of antisense polynucleotides specific to the telomeric repeat DNA sequences, in order to block telomere synthesis in these and any related pathogens. Such a block will lead to fungal death.

This approach is advantageous because of the unusual nature of the telomeric DNA in these fungi. The unusually high DNA sequence complexity of the telomeric repeats of these fungi provides specificity, and potential for minimal side effects, of the antifungal agent or the antisense DNA or RNA.

Agents that are potentially useful antifungal agents include: AZT, d4T, ddI, ddC, and ddA. The telomere synthesis of these fungi is expected to show differential inhibition to these drugs, and in some cases to be more sensitive than the telomere synthesis in the human or other animal or plant host cells.

We performed a preliminary test of the use of antisense techniques in living fungal cells. A stretch of 40 bp of telomeric DNA sequence, imbedded in a conserved sequence flanking a region of Candida albicans chromosomal DNA, was introduced on a circular molecule into Candida albicans cells. The transformed cells had high copy numbers of the introduced telomeric DNA sequence. 10% of the transformants exhibited greatly (~3-fold) increased length of telomeric DNA. This result indicates that telomeric DNA can be modulated in vivo by introduction of telomeric sequence polynucleotides into cells. This demonstrates the need to test a particular oligonucleotide to ensure that it has the desired activity.

With regard to diagnostic procedures, examples of such procedures become evident from the discussion above with regard to therapy. Applicant has determined that the length of the telomere is indicative of the life expectancy of a cell containing that telomere, and of an individual containing that cell. Thus, the length of a telomere is directly correlated to the life span of an individual cell. As discussed above, certain populations of cells may lose telomeres at a greater rate than the other cells within an individual, and those cells may thus become age-limiting within an individual organism. However, diagnostic procedures can now be developed (as described herein) which can be used to indicate the potential life span of any individual cell type, and to follow telomere loss so that a revised estimate to that life span can be made with time.

In certain diseases, for example, the AIDS disease discussed above, it would, of course, be important to follow the telomere length in $CD4^+$ cells. In addition, the recognition that $CD4^+$ cells are limiting in such individuals allows a therapeutic protocol to be devised in which $CD4^+$ cells can be removed from the individual at an early age when AIDS is first detected, stored in a bank, and then reintroduced into the individual at a later age when that individual no longer has the required $CD4^+$ cells available. These cells can be expanded in number in the presence of agents which slow telomere repeat loss, e.g., C-rich telomeric oligonucleotides or agents to transiently de-repress telomerase to ensure that cells re-administered to the individual have maximum replicative capacity. Thus, an individual's life can be extended by a protocol involving continued administration of that individual's limiting cells at appropriate time points. These appropriate points can be determined by following $CD4^+$ cell senescence, or by determining the length of telomeres within such $CD4^+$ cells (as an indication of when those cells will become senescent). In the case of AIDS, there may be waves of senescent telomere length in peripheral blood lymphocytes with bone marrow ten cells still having replicative capacity. In this way, rather than wait until a cell becomes senescent (and thereby putting an individual at risk of death) telomere length may be followed until the length is reduced below that determined to be pre-senescent, and thereby the timing of administration of new $CD4^+$ cells or colony stimulating factors can be optimized.

Thus, the diagnostic procedures of this invention include procedures in which telomere length in different cell populations is measured to determine whether any particular cell population is limiting in the life span of an individual, and then determining a therapeutic protocol to insure that such cells are no longer limiting to that individual. In addition, such cell populations may be specifically targeted by specific drug administration to insure that telomere length loss is reduced, as discussed above.

Other diagnostic procedures include measurement of telomerase activity as an indication of the presence of immortal cells within an individual. A more precise measurement of such immortality is the presence of the telomerase enzyme itself. Such an enzyme can be readily detected using standard procedures, including assay of telomerase activities, but also by use of antibodies to telomerase, or by use of oligonucleotides that hybridize to the nucleic acid (template RNA) present in telomerase, or DNA or RNA probes for the mRNAs of telomerase proteins. Immunohistochemical and insitu hybridization techniques allow the precise identification of telomerase positive cells in histological specimens for diagnostic and prognostic tests. The presence of telomerase is indicative of cells which are immortal and frequently metastatic, and such a diagnostic allows pinpointing of such metastatic cells, much as CD44 is alleged to do so. See, Leff, 3(217) *BioWorld Today* 1, 3, 1992.

It is evident that the diagnostic procedures of the present invention provide the first real method for determining how far certain individuals have progressed in a certain disease. For example, in the AIDS disease, this is the first methodology which allows prior determination of the time at which an HIV positive individual will become immunocompromised. This information is useful for determining the timing of drug administration, such as AZT administration, and will aid in development of new drug regimens or therapies. In addition, the determination of the optimum timing of administration of certain drugs will reduce the cost of treating an individual, reduce the opportunity for the drug becoming toxic to the individual, and reduce the potential for the individual developing resistance to such a drug.

In other related aspects, the invention features a method for treatment of a disease or condition associated with cell senescence, by administering a therapeutically effective amount of an agent active to derepress telomerase in senescing cells. A related aspect involves screening for a telomerase derepression agent by contacting a potential agent with a cell lacking telomerase activity, and determining whether the agent increases the level of telomerase activity, e.g., by using a cell expressing an inducible T antigen. Such an assay allows rapid screening of agents which are present in combinatorial libraries, or known to be carcinogens.

Applicant recognizes that known agents may be useful in treatment of cancers since they are active at telomerase itself, or at the gene expressing the telomerase. Thus, such agents can be identified in this invention as useful in the treatment of diseases or conditions for which they were not previously known to be efficacious. Indeed, agents which were previously thought to lack utility because they have little if any effect on cell viability after only 24–48 hours of treatment, can be shown to have utility if they are active on telomerase in vivo, and thus affect cell viability only after several cell divisions.

Other features and advantages of the invention will be apparent from the following description of the preferred embodiments thereof, and from the claims.

DESCRIPTION OF THE PREFERRED EMBODIMENTS

The drawings will first briefly be described.
Drawings

Figure 7:
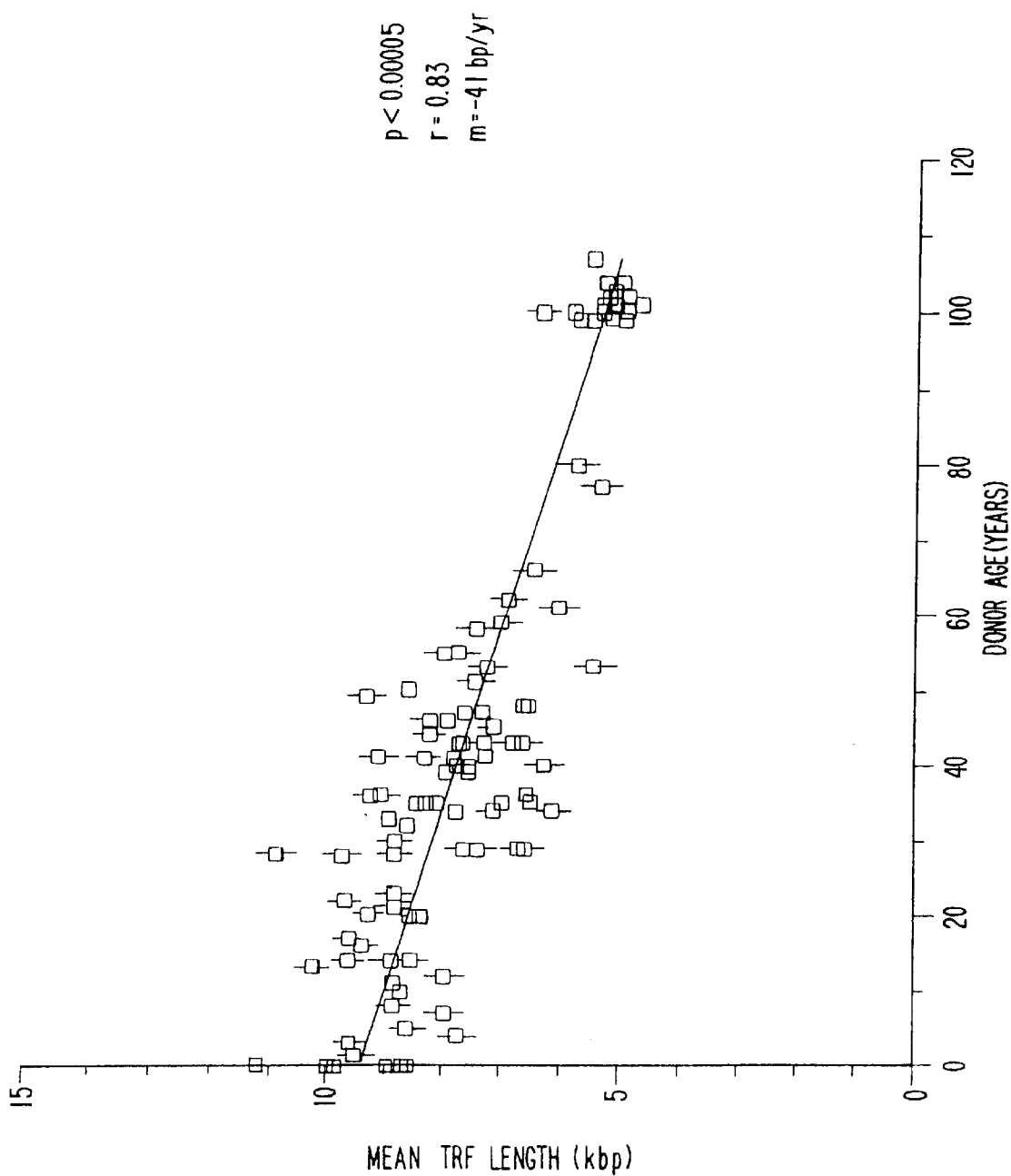
FIG. 7 is a plot of mean TRF length from PBLs plotted as a function of donor age. The slope of the linear regression line ($-41 \pm 2.6$ bp/y) is significantly different from 0 (p<0.00005).
Figure 8:
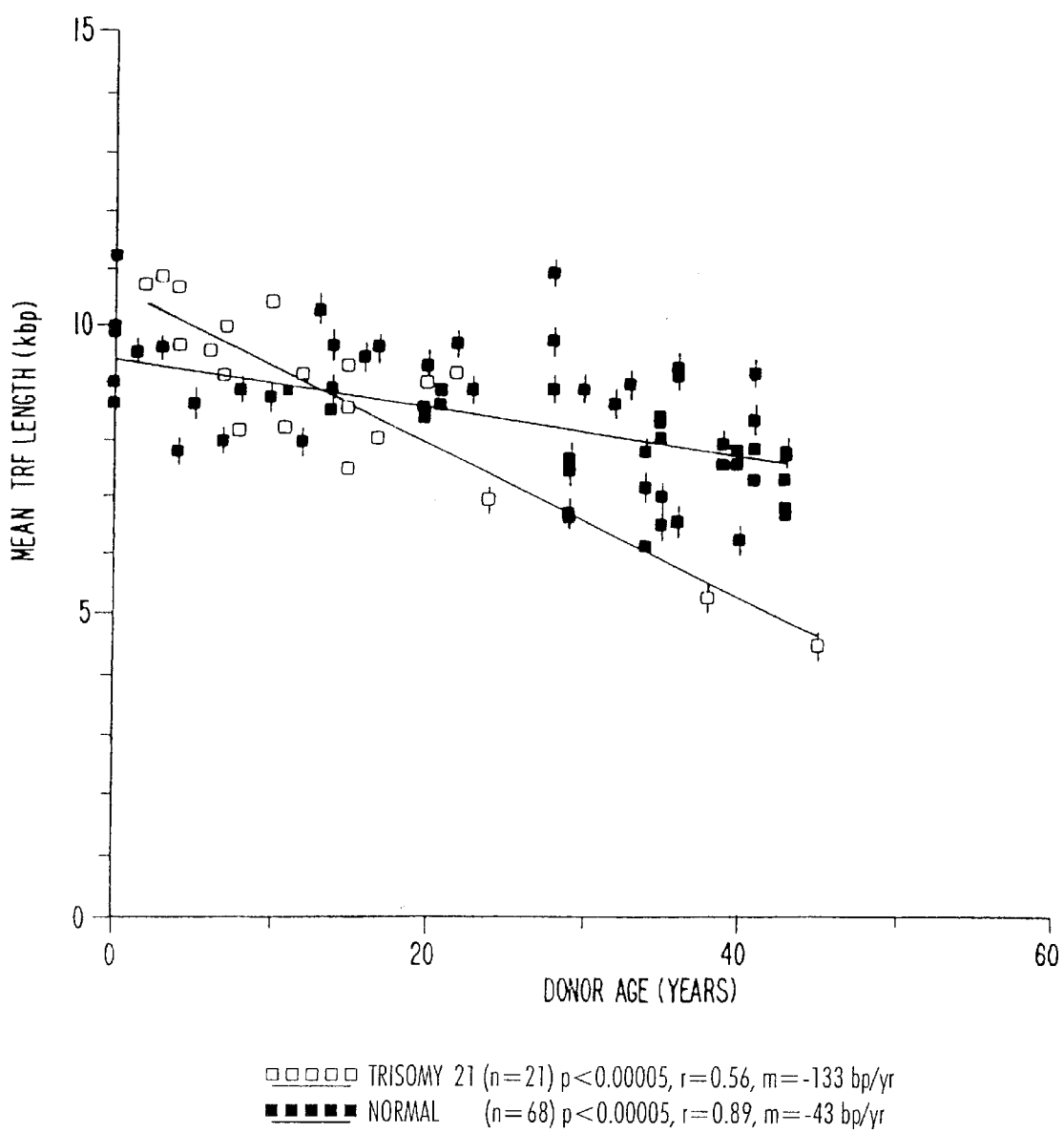

FIG. 8 is a plot showing accelerated telomere loss in Down's Syndrome (DS) patients. Genomic DNA isolated from PBLs of DS patients was analyzed as described in FIG. 7. Mean TRF length is shown as a function of donor age, for DS patients (open squares), and age-matched controls (solid squares). The slope of the linear regression lines ($-133 \pm 15$ bp/y, trisomy, vs $-43 \pm 7.7$, normals) are significantly different (p<0.0005).

Figure 9:
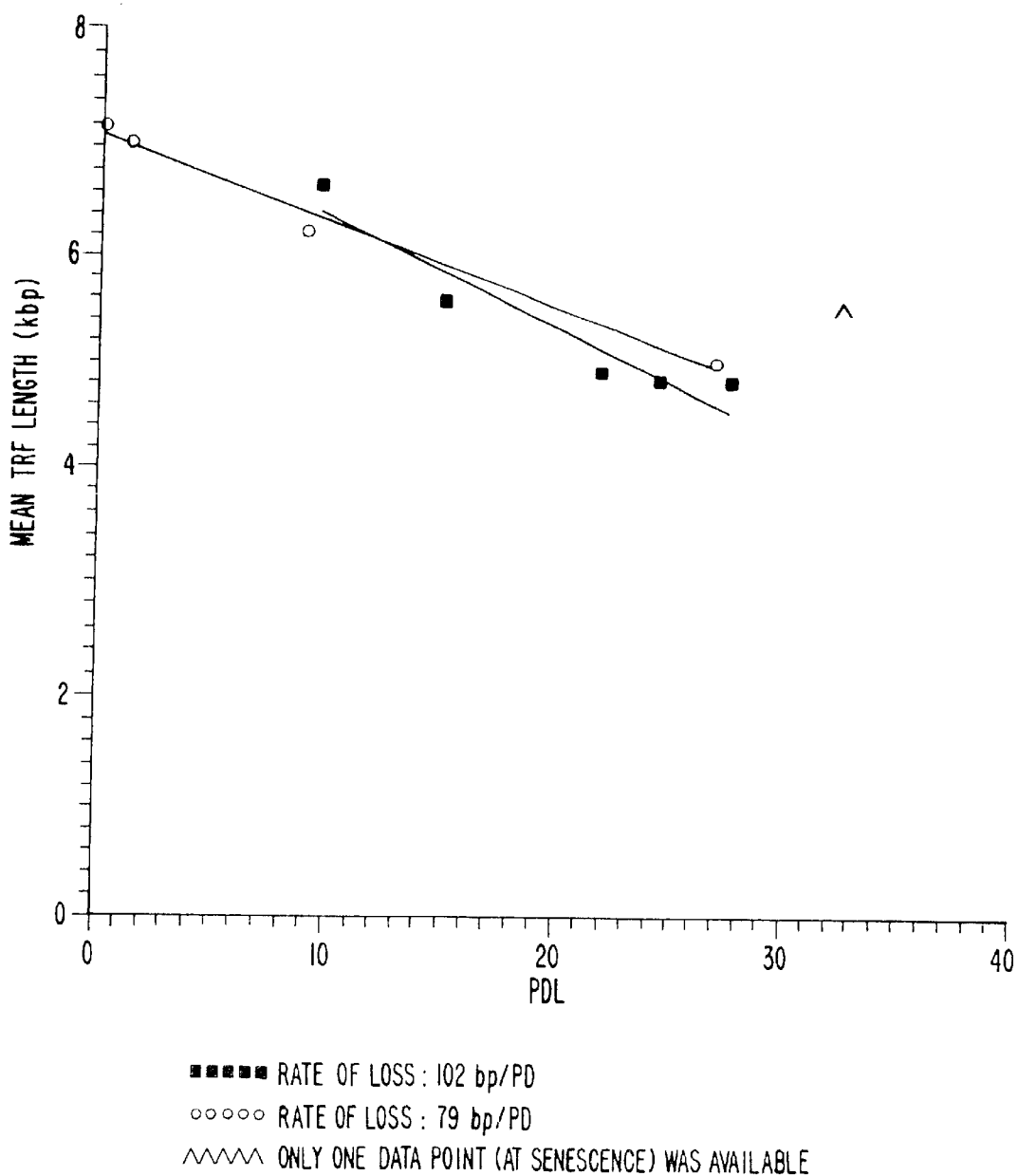

FIG. 9 is a plot showing decrease in mean TRF length in cultured T-lymphocytes as a function of population doubling (shown for DNA from two normal individuals). Donor ages for these cells were not available. The slopes of these lines ($-80 \pm 19$ (°) and $-102 \pm 5.4$ (O) bp/doubling) are significantly different from zero (p<0.0001). Mean TRF length at terminal passage from a third donor for which multiple passages were not available is also shown (upsidedown V-symbol).

Figure 10:
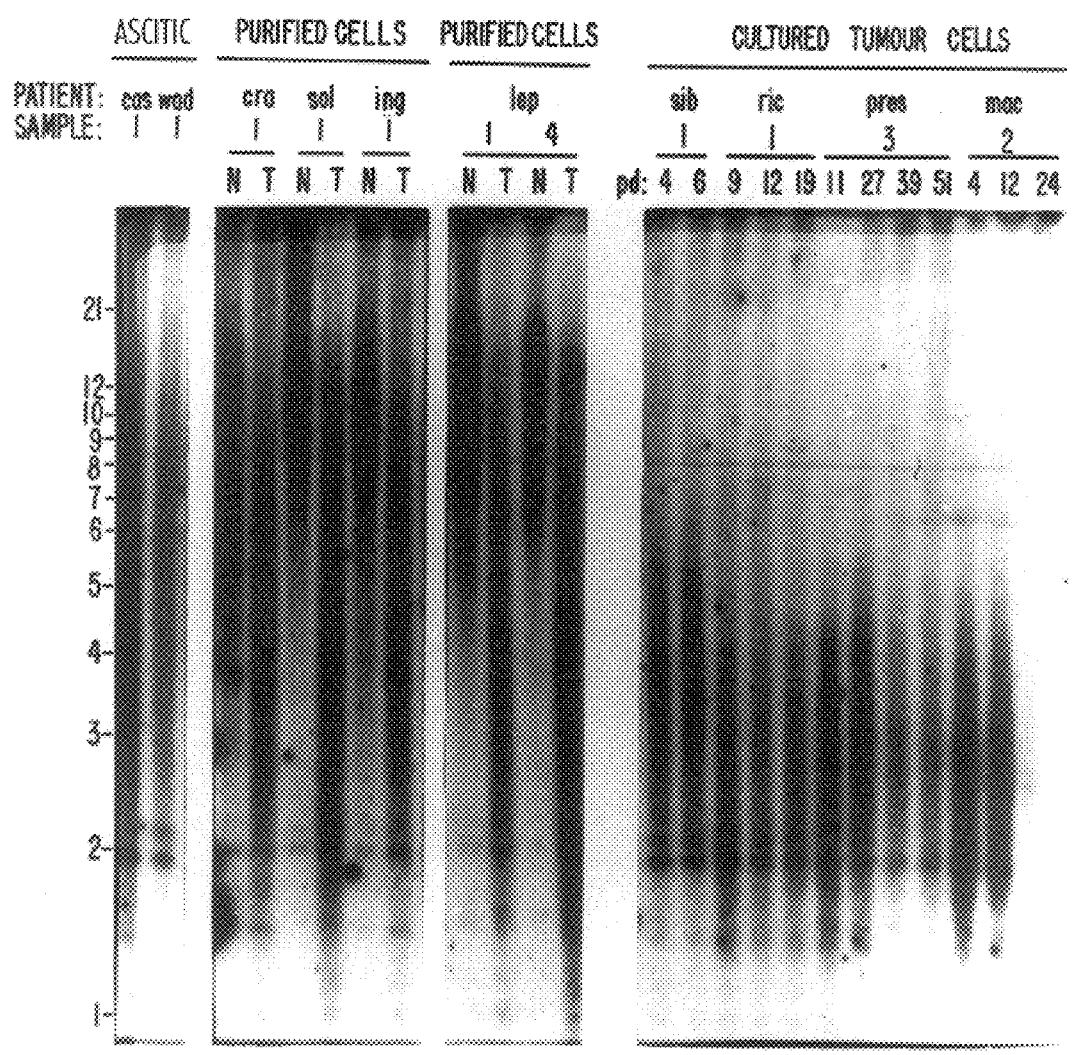

FIG. 10 is a copy of an autoradiogram showing TRF lengths of ovarian carcinoma and control normal cells. DNA from cells in ascitic fluid from 2 patients (cas and wad) was digested with HinfI and RsaI separated by electrophoresis, hybridized to the telomeric probe $^{32}P(CCCTAA)_3$, stringently washed and autoradiographed. The cells of ascitic fluid from 7 other patients were separated into adhering normal cells (N) and tumour clumps in the media (T). The DNA was extracted and run as above. DNA from patient was obtained from both the first and forth paracentesis. Tumour cells from patients were cultured and DNA was obtained at the respected population doubling (pd).

Figure 11:
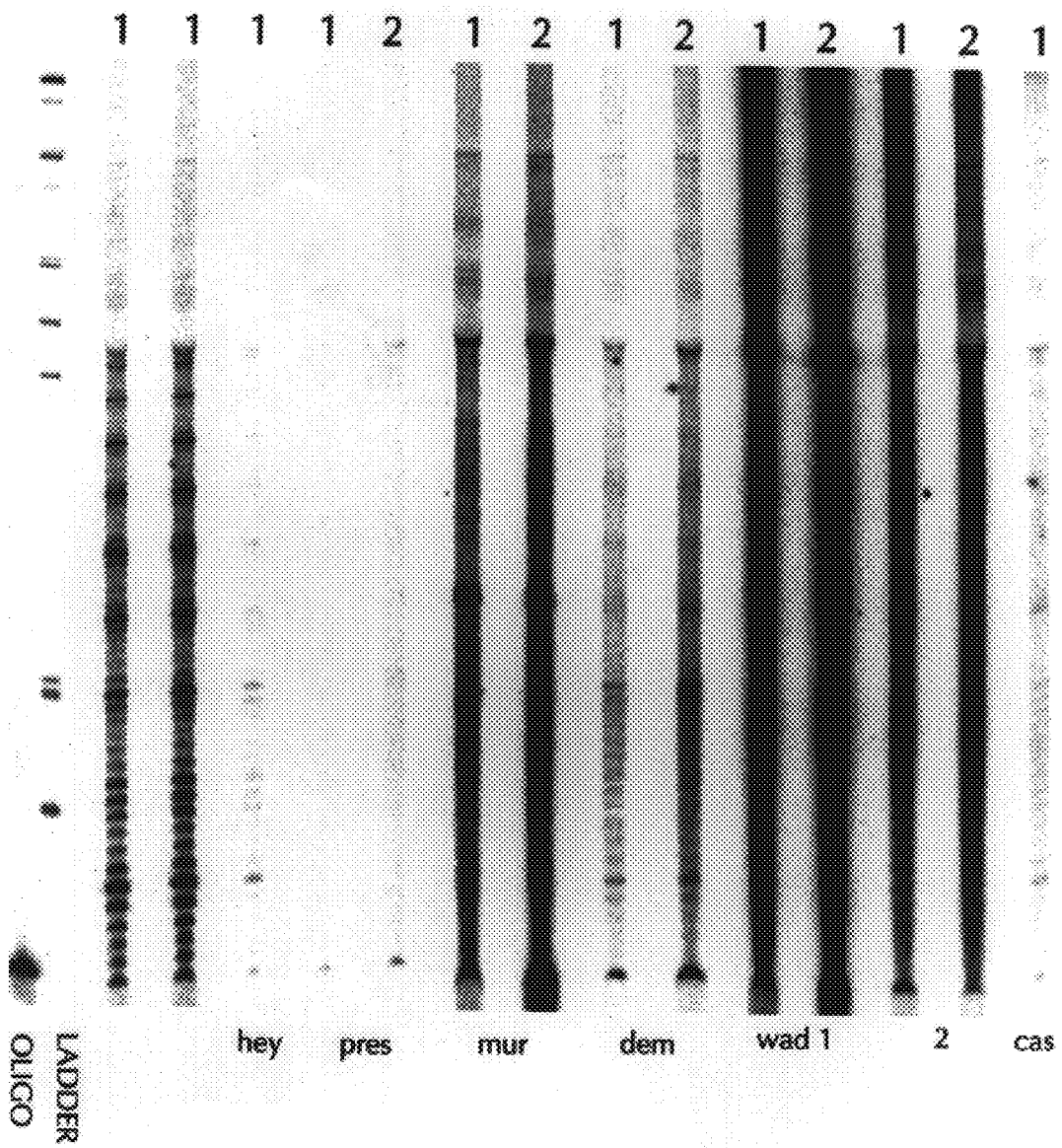

FIG. 11 shows telomerase activity in ovarian carcinoma cells. S100 extracts from the previously studied transformant cell line 293 CSH, the tumor cell line HEY, purified tumour cell population and cells directly from the ascitic fluid from patients were incubated with the telomere primer $(TTAGGG)_3$ in the presence of dATP and TTP, $^{32}PdGTP$ and buffer. The reaction products were separated on a sequencing gel and exposed to a PhosphoImager screen. Either single (1) or double reactions (2) were tested.

Figure 12:
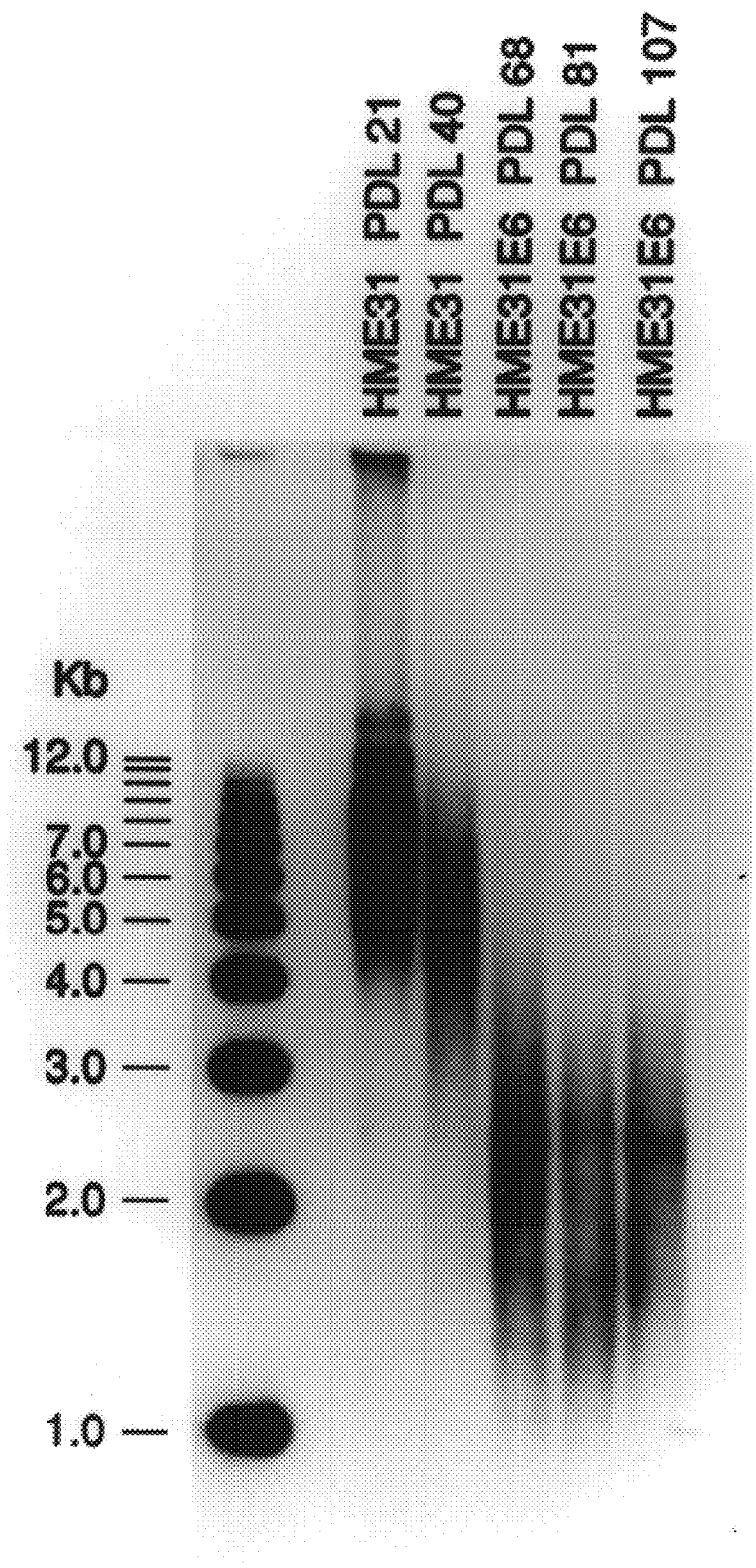

FIG. 12 is a copy of an autoradiogram showing TRF lengths in HME-31 cells and HME31-E6 cells to extended lifespan (PD68) and subsequent immortalization and stabilization of telomere length (PD81, 107).

Figure 13:
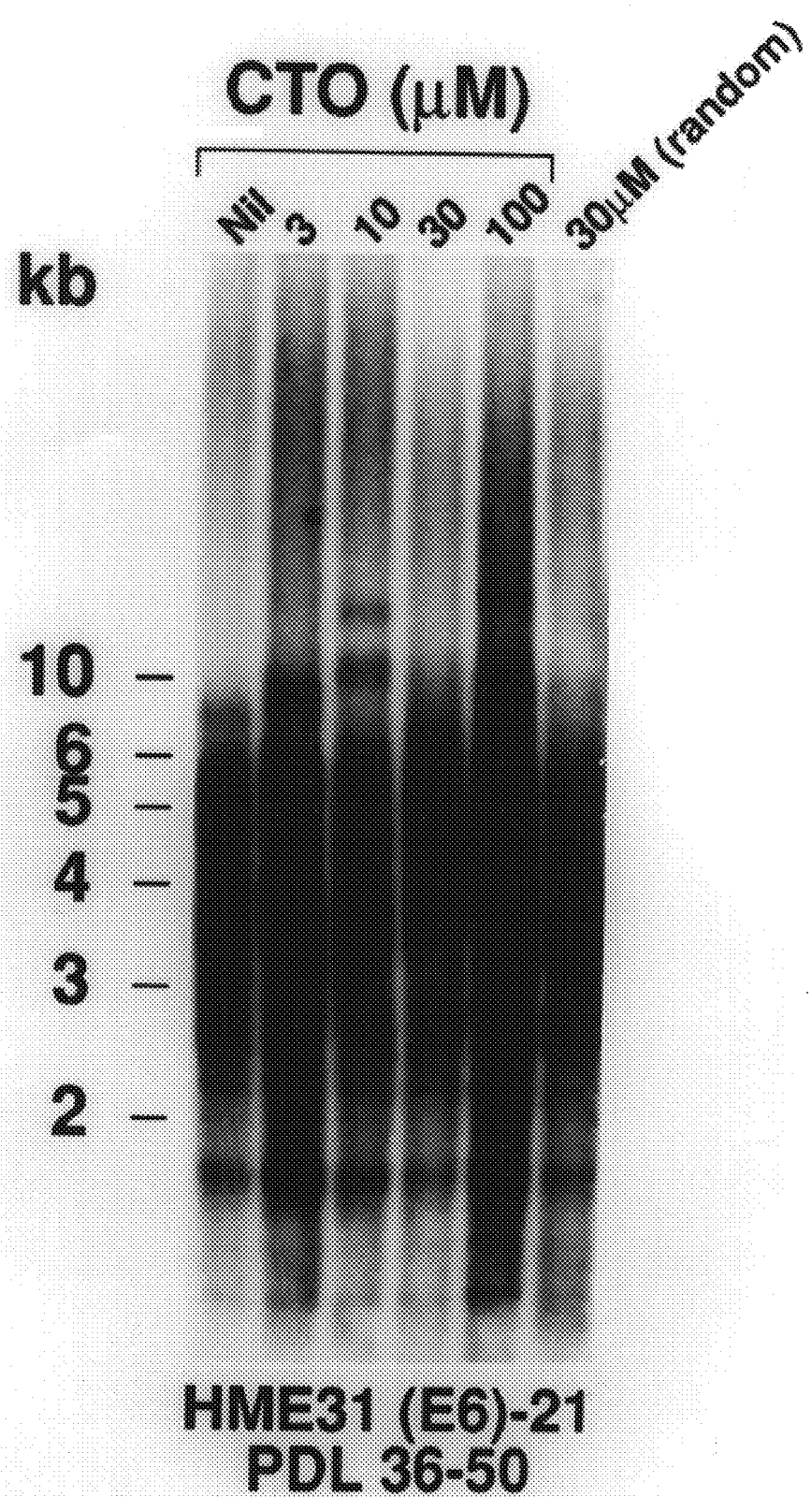

FIG. 13 is a copy of an autoradiogram showing the effect of CTR on telomere length during the senescence of HME31:E6 cells. An intermediate time point is chosen to show the dose-dependent protective effect of CTR oligonucleotide.

Figure 14:
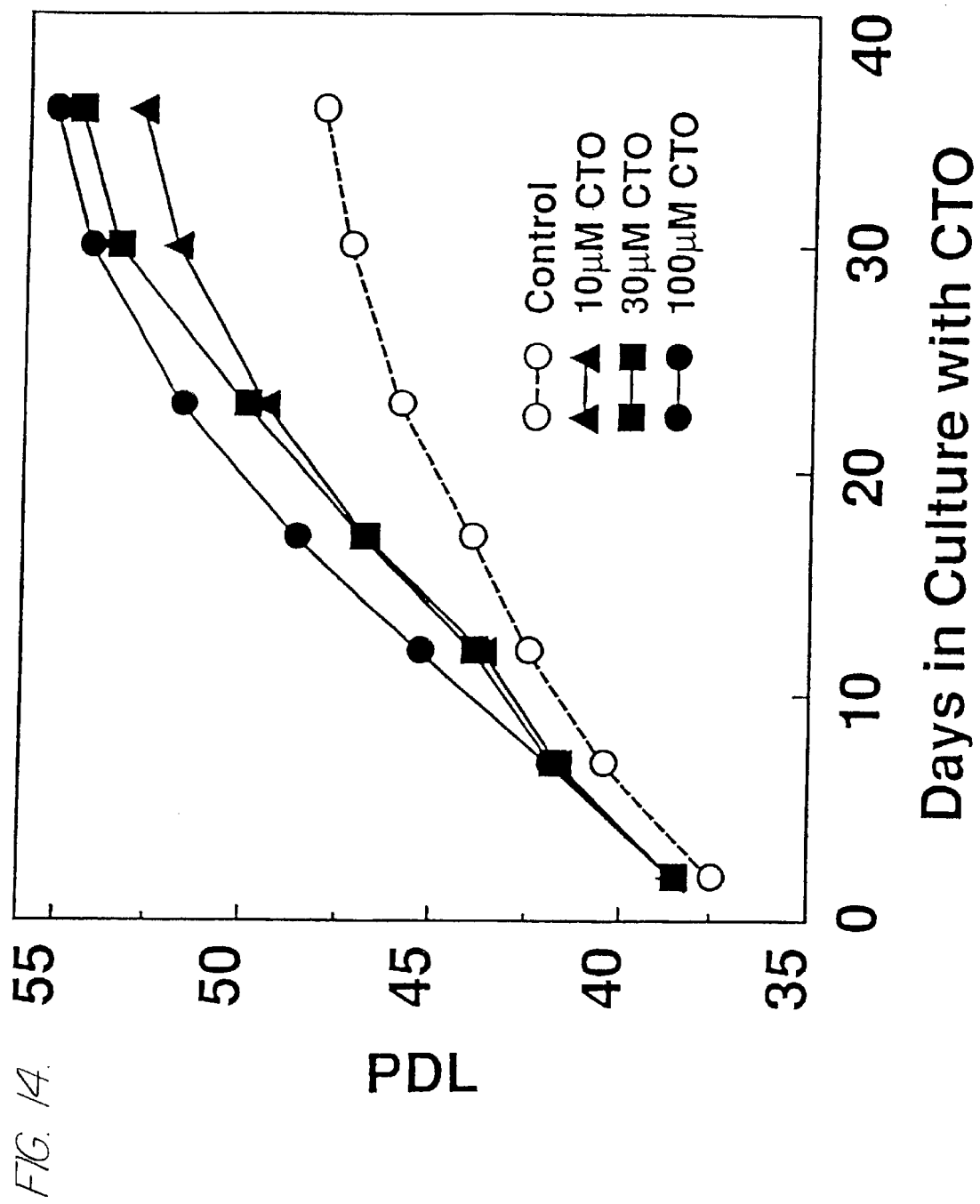

FIG. 14 is a graph showing extension of the life span of IMR90 lung fibroblast cells in response to the CTO oligonucleotide.

Figure 15:
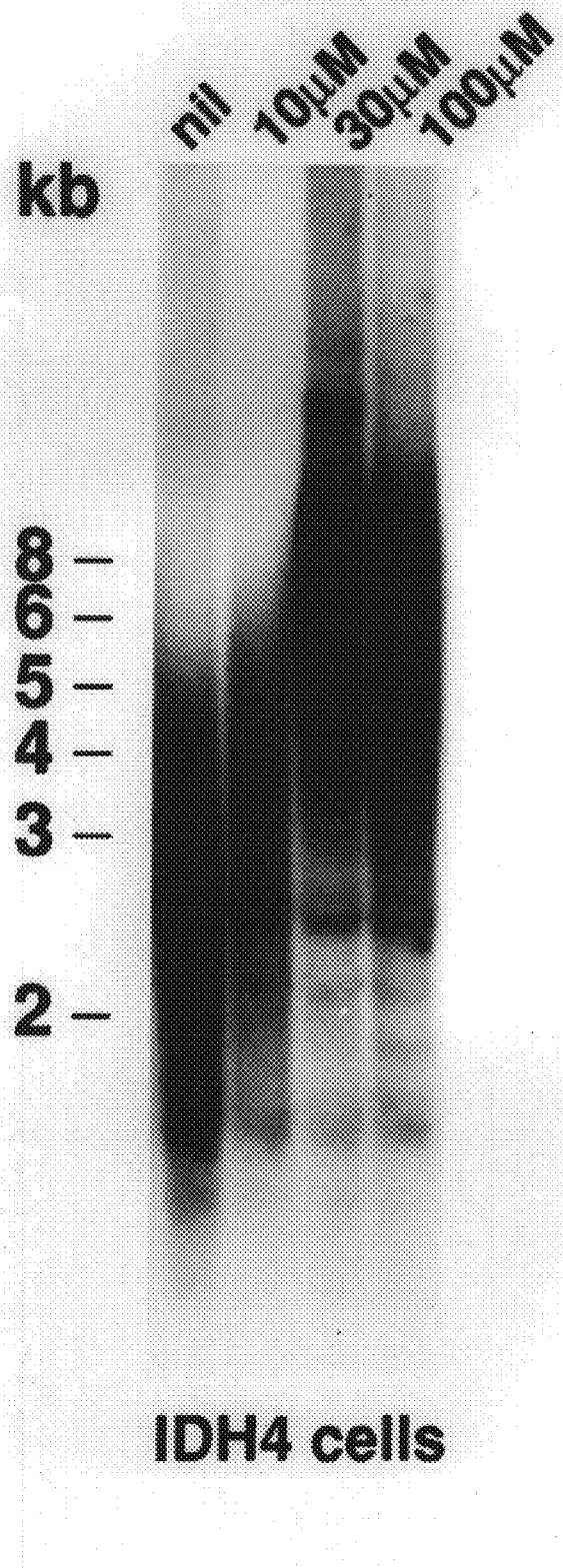
Figure 16:
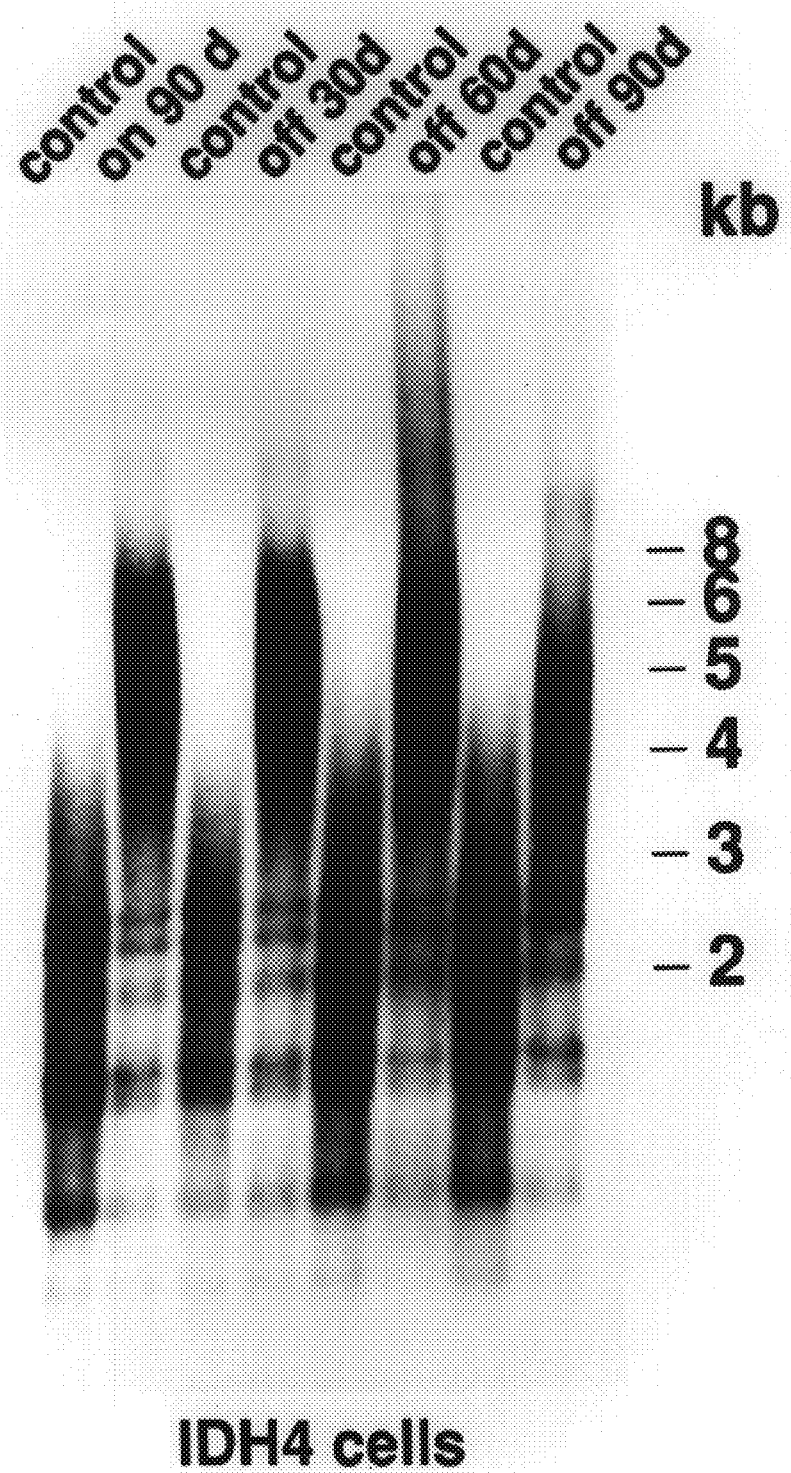

FIGS. 15 and 16 are copies of autoradiograms showing the effect of GTO on telomere length in IDH4 cells.

Figure 17:
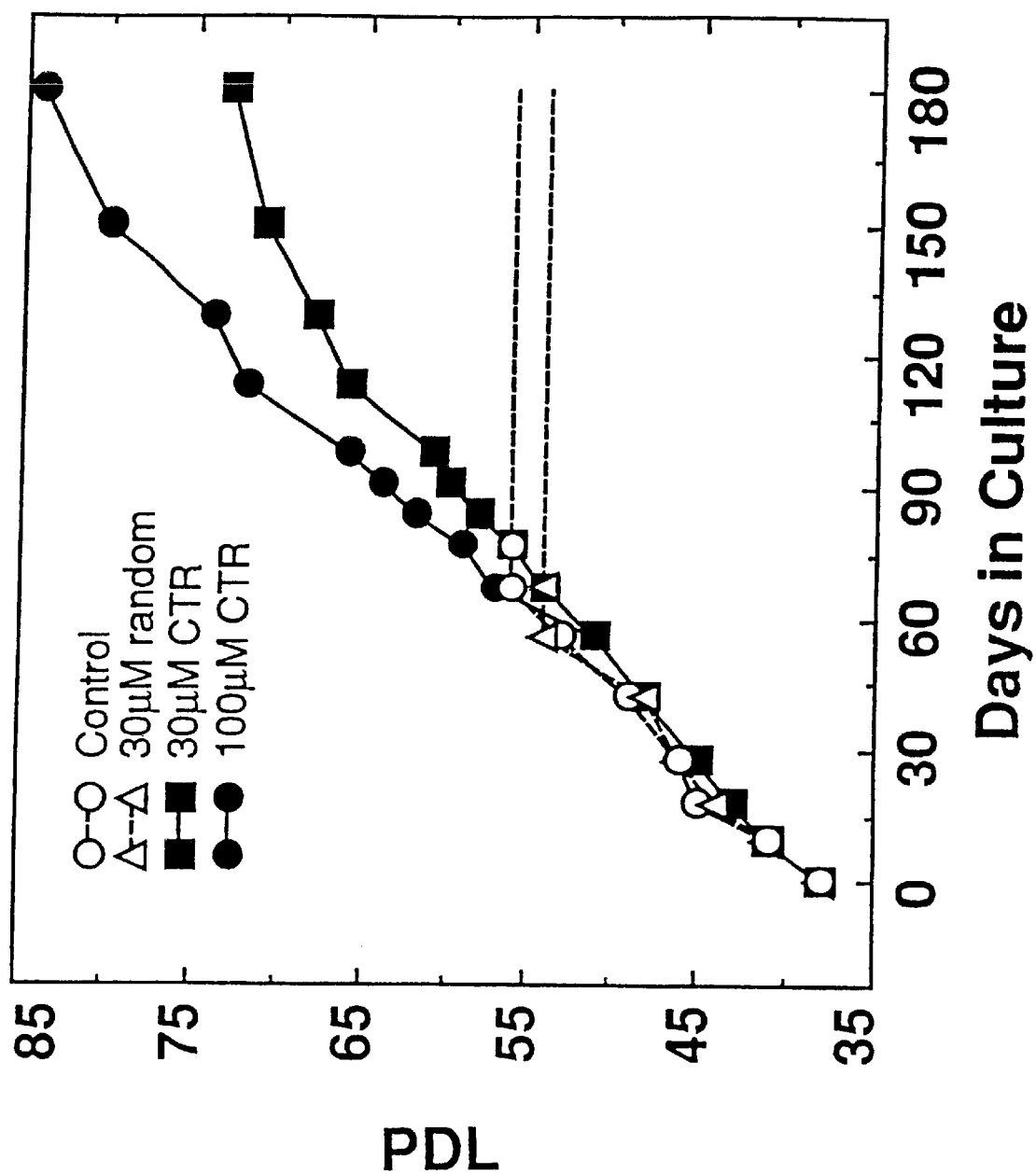

FIG. 17 is a graph showing extension of the life span of HME31:E6 human breast epithelial cells in response to the CTO oligonucleotide.

FIG. 18A. shows the templating portion of the Tetrahymena telomerase RNA with residues numbered 1 (5') through 9 (3') below it. The oligonucleotide primer with the sequence $T_2G_4T_2G_4$ binds to the template by the base-pairing shown. Elongation followed by template translocation are thought to occur as indicated.

FIG. 18B shows positions of major chain termination on the telomerase RNA template by different nucleoside triphosphate analogs. The telomerase RNA template sequence is shown as in FIG. 18A. Arrows indicate the position of maximal chain termination for each nucleoside triphosphate (derived from the nucleoside) analog shown.

FIGS. 19A–F are graphs showing that nucleoside analog triphosphates inhibit incorporation of a $^{32}P$ label in a Tetrahymena telomerase assay. The effect of adding increasing concentrations of the analog, unlabeled dGTP or unlabeled TTP on the incorporation of labeled nucleotides was measured using a quantitative telomerase reaction assay. Radioactivity incorporated (cpm) was plotted against the concentration of competitors indicated in each panel. (A. labeled with $[\alpha-^{31}P]TTP$. B—F. labeled with $[\alpha-^{32}P]dGTP$. F. Effect of streptomycin sulfate on the telomerase reaction. The incorporation in the presence of 40 mM sodium sulfate is shown as the control for streptomycin sulfate).

Figure 20A:
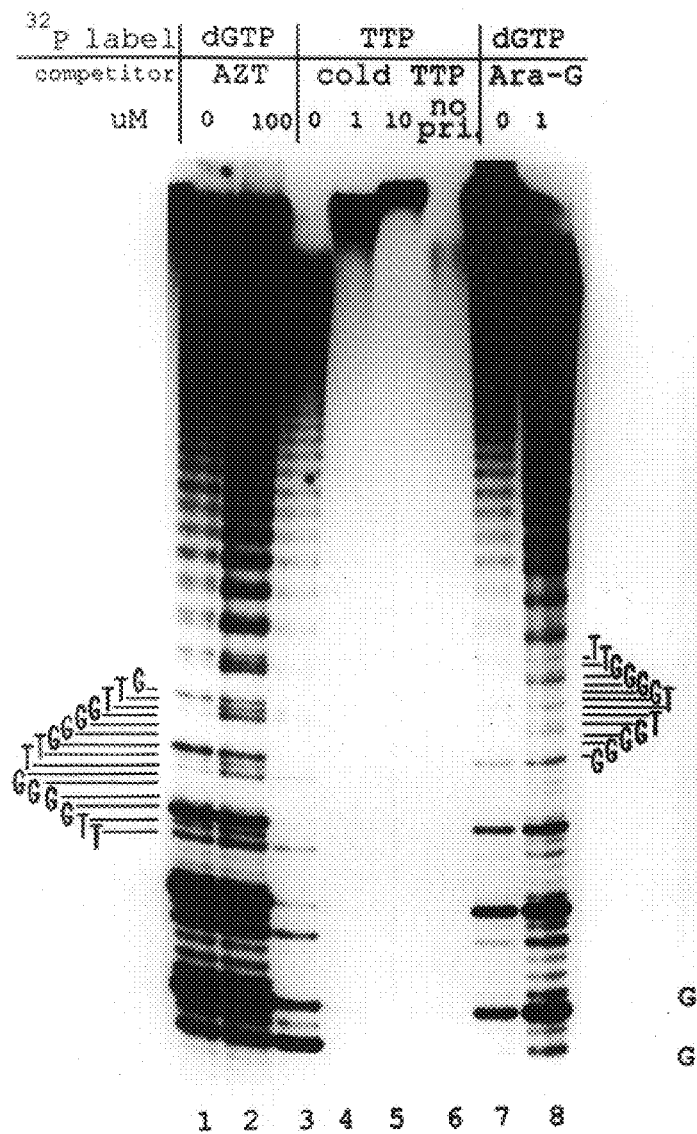

FIGS. 20A and B show the effect of nucleoside triphosphate analogs on pausing patterns and processivity of telomerase in vitro. Specifically, FIG. 20A shows telomerase reactions in the presence or absence of the indicated nucleoside triphosphate analogs. Unlabeled TTP competitor was also analyzed as a control, with and without primer in the reaction mix. Products were then analyzed on a denaturing polyacrylamide gel.

Figure 20B:
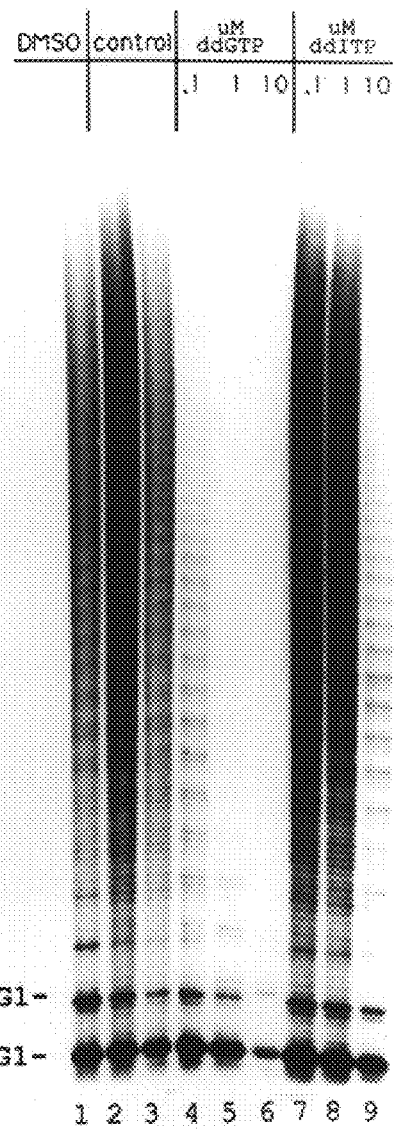

FIG. 20B shows standard telomerase reactions were performed in the presence of ddGTP (lanes 4–6), ddITP (lanes 7–9), or DMSO (lane 1). DMSO was the solvent for ddGTP and at the highest concentration tested (1%) showed no effect on the reactions compared with control reactions run without analog or DMSO (control lanes 2–3). Products were analyzed on a denaturing polyacrylamide gel.

Figures 21A, 21B, 21C, 21D:
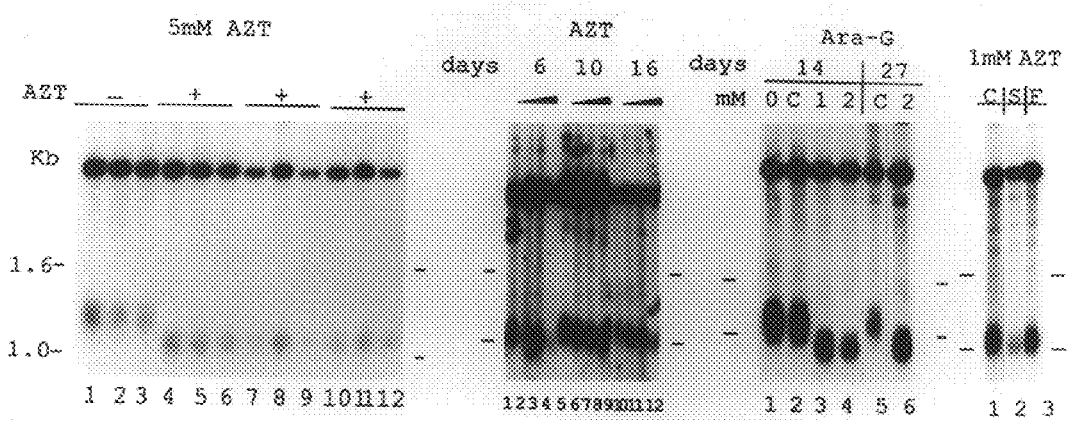

FIGS. 21A–D shows Southern blot analysis to demonstrate the effect of nucleoside analogs on telomere length in vivo, using a nick-translated $[\alpha-^{32}P]$-labeled plasmid containing a 3' rDNA fragment as probe. Genomic DNA was digested with PstI and BamHI and the rDNA telomeres analyzed. The telomeric PstI fragment from the rDNA is between the 1.6 and 1.0 kb markers, indicated as lines on both sides of each panel. The constant 2.8 kb band is the adjacent internal PstI rDNA fragment. Specifically, FIG. 21A shows results with a clone of *Tetrahymena thermophila* grown in 2% PPYS in the absence (−) and three clones in the presence (+) of 5 mM AZT. Each set of three lanes shows the results for a single cell clone grown vegetatively and transferred after 3 days (lanes 1, 4, 7, 10), 10 days (lanes 2, 5, 8, 11) and 16 days (lanes 3,6,9,12).

FIG. 21B shows that growth in different concentrations of AZT consistently resulted in concentration-dependent shortening of telomeres in log phase cells grown in thymine-deficient broth (Isobroth) plus AZT. DNA made from cells sampled at 6, 10, and 16 days show that shortened telomere lengths remain constant between 6 and 16 days in culture. Lanes 1, 5, 9, 0 mM AZT control; lanes 2, 6, 10, 0.01 mM AZT; lanes 3, 7, 11, 0.1 mM AZT; lanes 4, 8, 12, 1 mM AZT.

FIG. 21C shows cells grown vegetatively in 2% PPYS with no addition (lane 1), with 1% DMSO, the solvent for Ara-G, ("C", lanes 2 and 5), and with Ara-G (lane 3, 1 mM; lanes 4 and 6, 2 mM ) at 14 and 27 days in culture.

FIG. 21D shows analysis of DNA from single-cell cultures grown in Isobroth plus 1 mM AZT (lanes 2 and 3) segregated into two classes based on growth rate: "slow" ("S", 0–1 doubling per day, lane 2) or "fast" ("F", 2–4 doubling per day, lane 3). DNA from control cultures grown in the absence of AZT are indicated ("C", 2–4 doubling per day, lane 1). Several cultures were pooled in order to obtain sufficient DNA for analysis.

Figure 22:
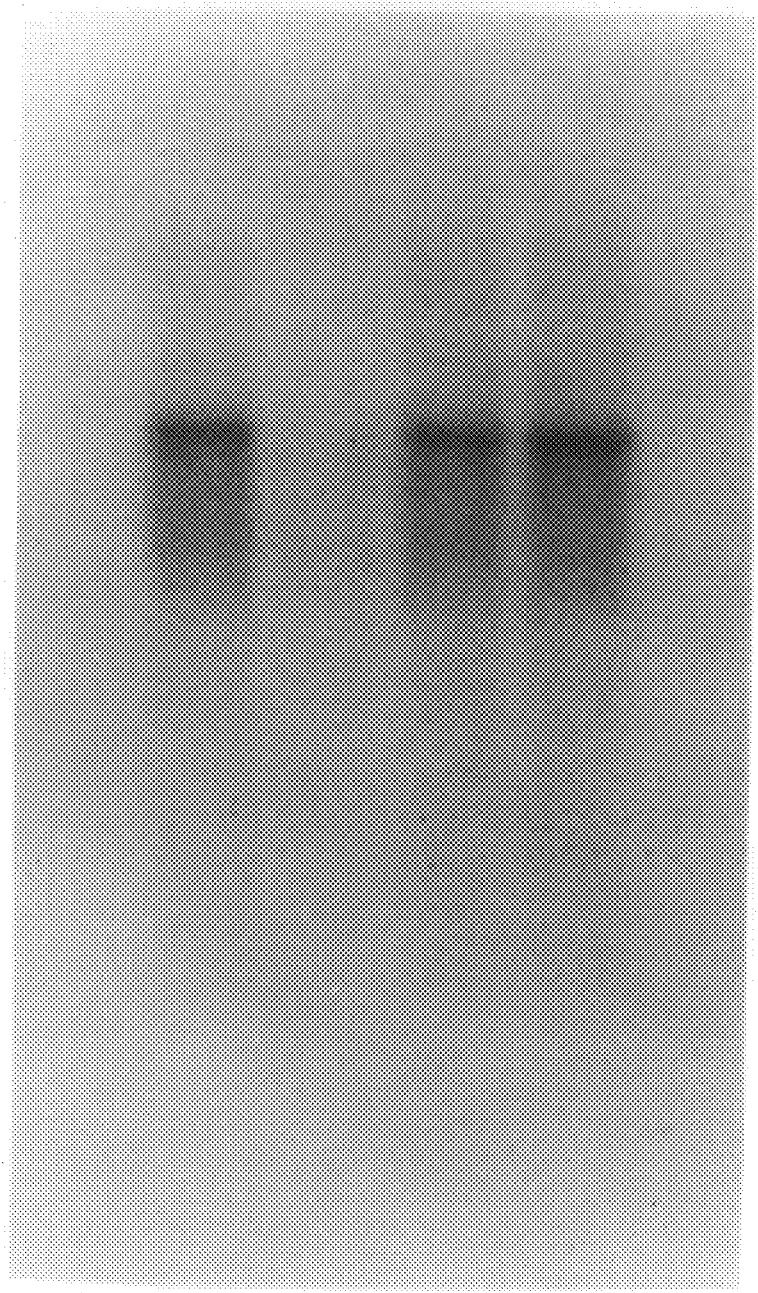

FIG. 22 shows PCR analysis of DNA from Tetrahymena cells conjugated in the presence of analog and starved for the duration of mating. A Telomeric primer and a 5' rDNA primer were used in PCR reactions with DNA from cells conjugated in the presence or absence of analog to detect the addition of telomeres to the 11 Kb rDNA formed during macronuclear development. A reaction was run without DNA as a control. Tests included use of 5 mM AZT; 1 mM Ara-G, and 1 mM Acyclo-G. SB210 cells were also mock-conjugated as a control. The expected product is approximately 1400 bp. In addition, 3' micronuclear rDNA primers were used on the same DNA to demonstrate the presence and competence of the DNA samples for PCR. The expected band is 810 bp. In the figure southern blot analysis of the 5' rDNA telomeric PCR reactions using a random-primed $^{32}$P-labeled 5'rDNA probe confirmed the 1400 bp PCR product as part of the 5'rDNA with telomeres, from the 11 Kb rDNA species formed transiently during macronuclear development. No hybridization is seen in the no DNA control (lane 1) or the SB210 mock-conjugated control (lane 6). Lane 2, no added analog; lane 3, 5 mM AZT., lane 4, 1 mM Ara-G; lane 5, 1 mM Acyclo-G; lane 6, mock-conjugated SB210 cell DNA. These results were reproduced in three separate experiments.

Figure 23:
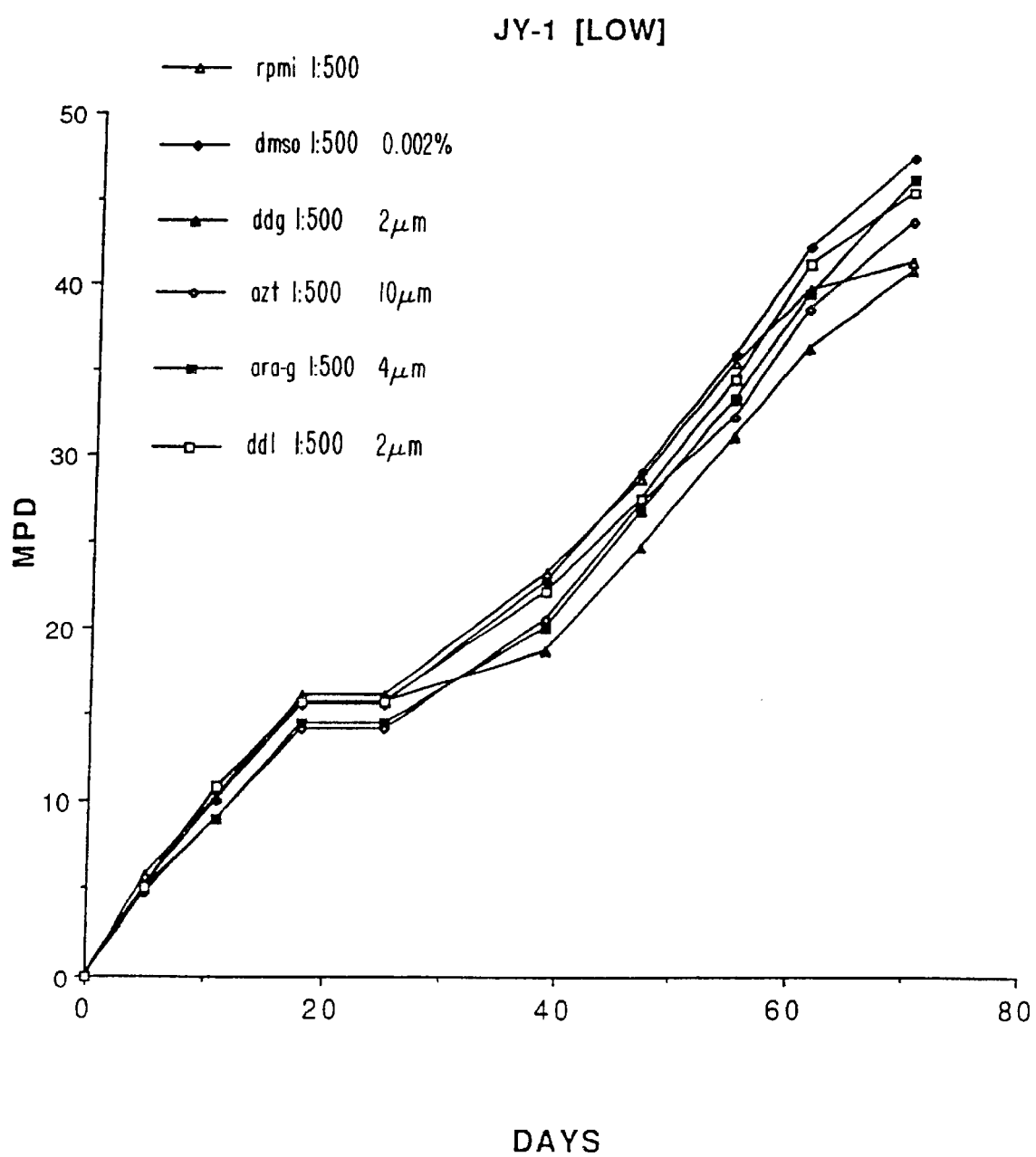

FIG. 23 shows growth of cultured JY lymphoma cells with RPMI medium and no added agents (control) and with a relatively low dose of ddG, AZT, ara-G, and ddI. The DMSO is a control for ddG.

Figure 24:
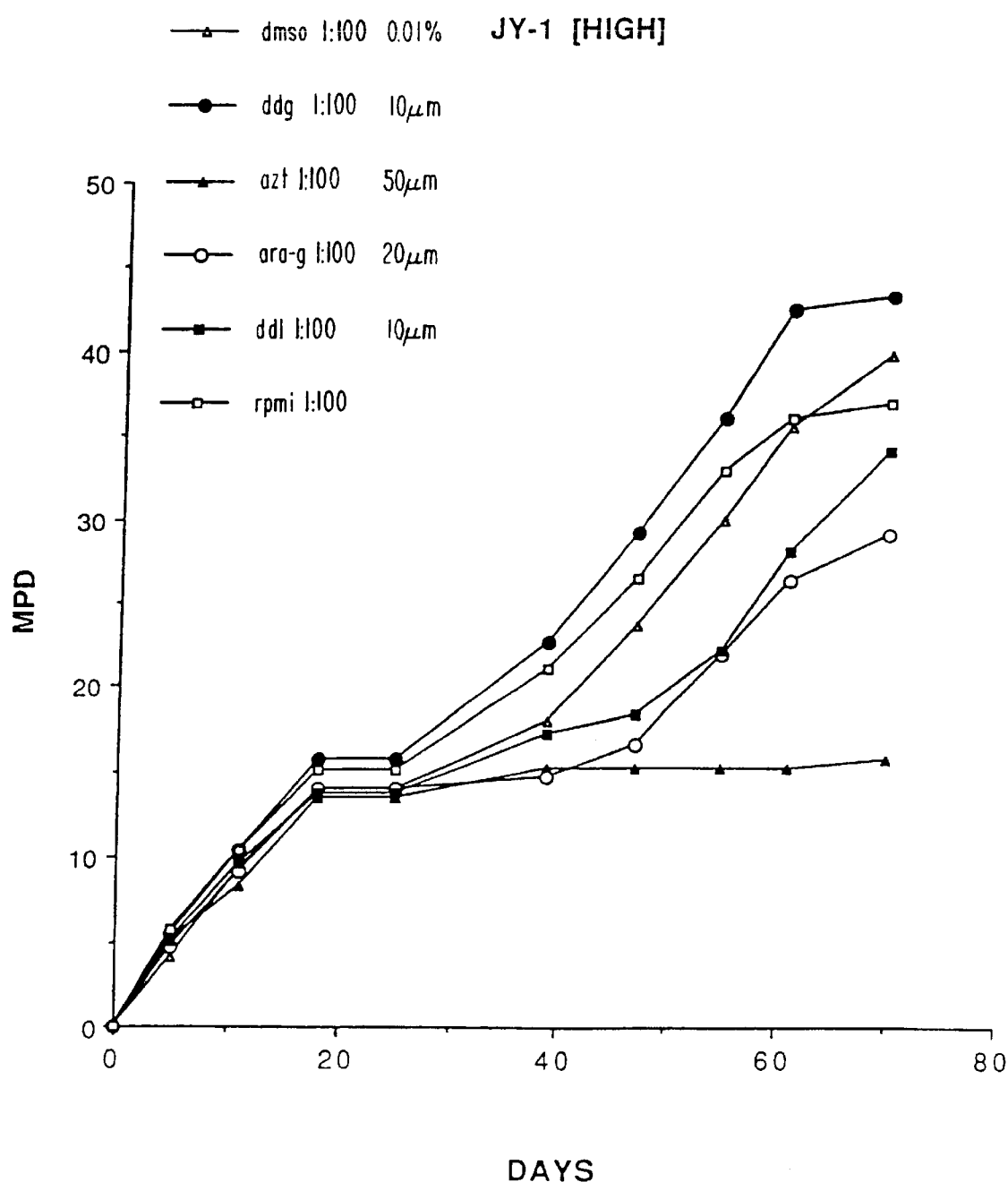

FIG. 24 shows the growth of cultured JY lymphoma cells cultured in an analogous manner to those in FIG. 23, but treated with relatively higher doses of potential telomerase inhibitors.

Figure 25A:
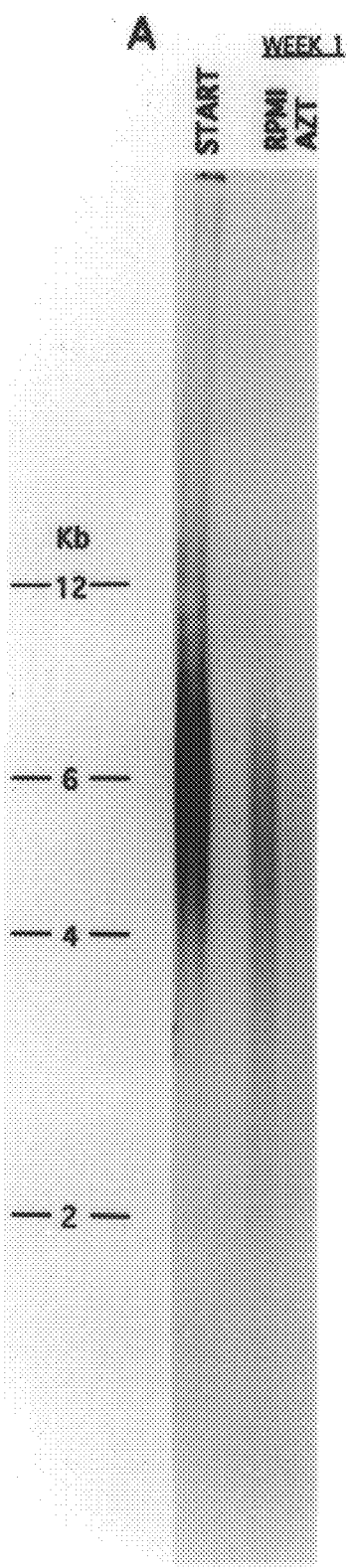
Figure 25B:
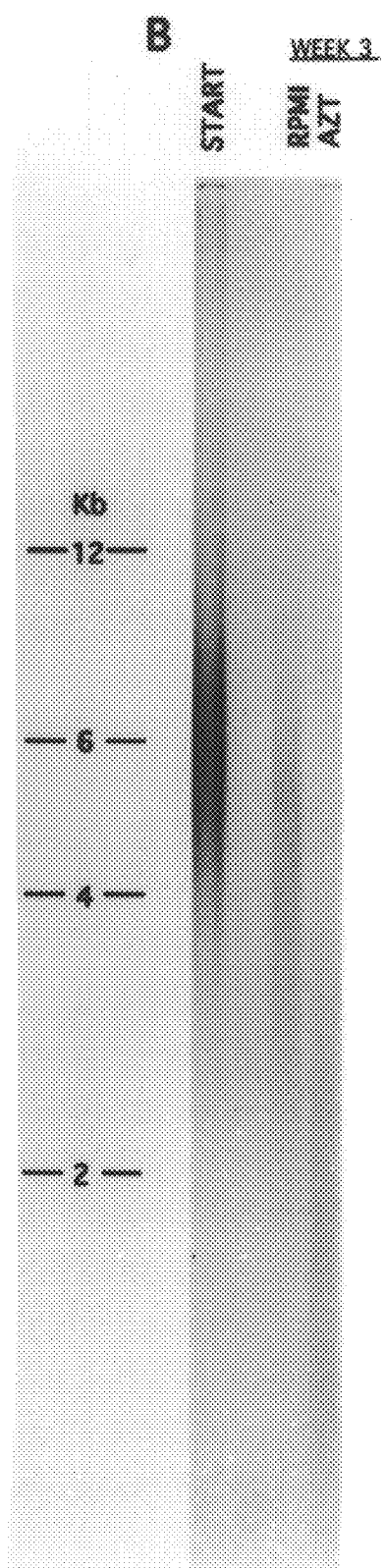

FIGS. 25A and 25B show Southern blot of DNA isolated from JY lymphoma cells at weeks one (FIG. 25A) and three (FIG. 25B) probed with the telomeric repeat sequence (TTAGGG)$_3$. The first lane is DNA from the cells at the start of the experiment, the second is the RPMI control, and the third is cells treated with AZT for the times indicated.

Figure 26:
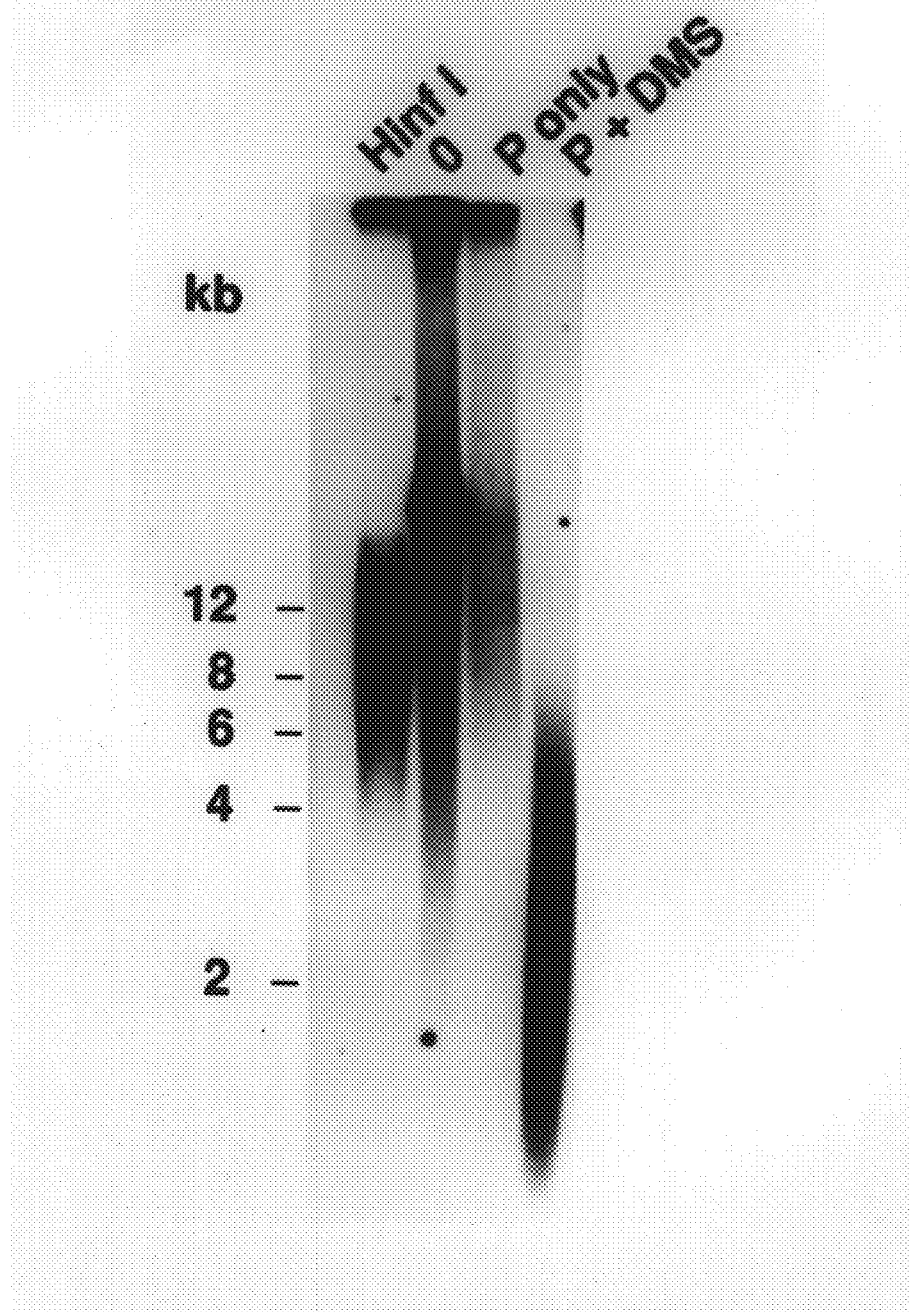

FIG. 26 shows fibroblast DNA hybridized by Southern blot to the telomeric (TTAGGG)$_3$ probe. Lane labeled "HinfI" is DNA digested with the restriction enzyme HinfI, the lane labeled "O" had no treatment, the lane labeled "P only" was treated with piperidine, and the lane labelled "P+DMS" was piperidine and dimethyl sulfate treated.

Figure 27:
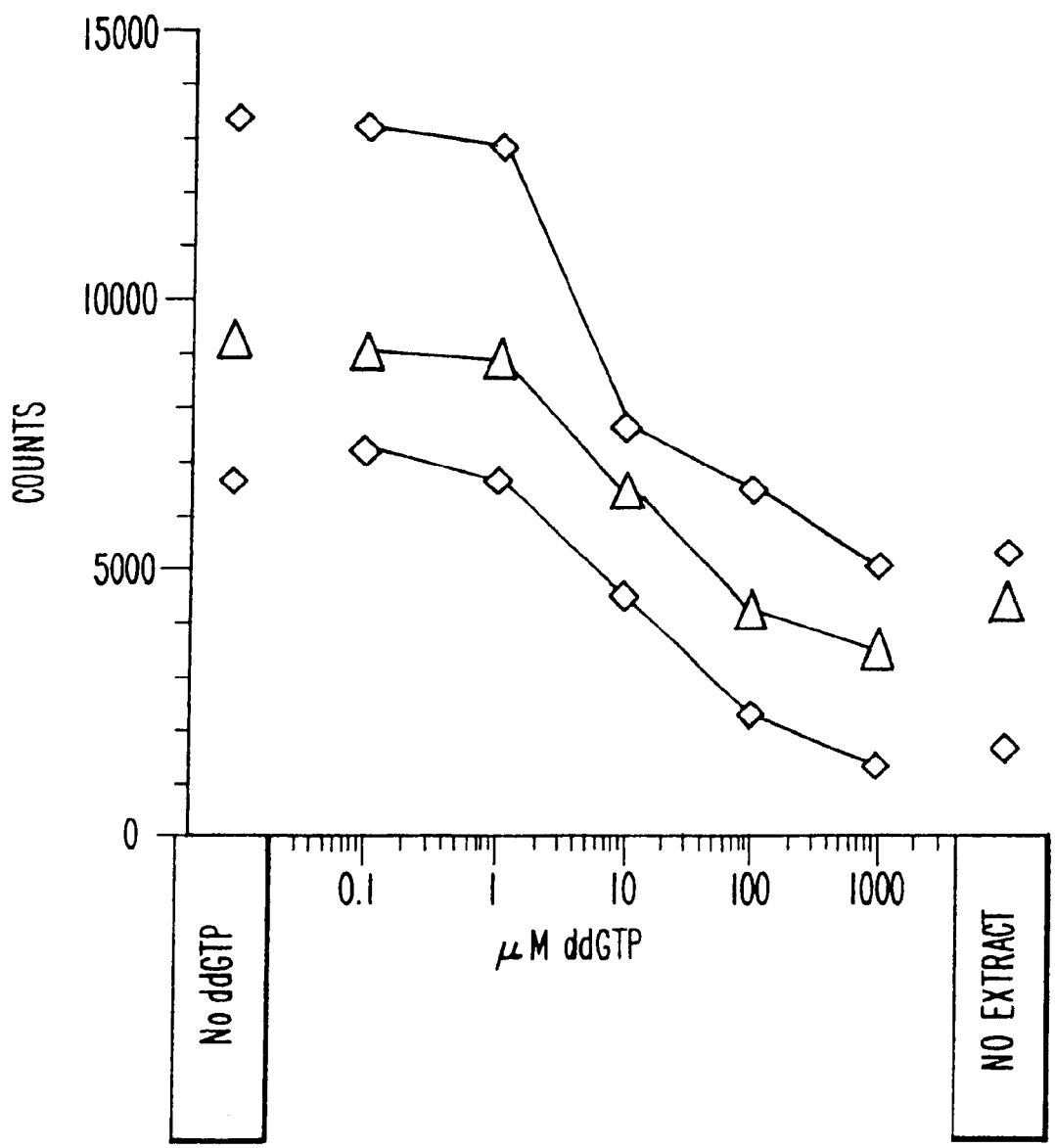

FIG. 27 shows the inhibition of human telomerase achieved by the agent ddG at various dosages in three separate experiments. The telomerase was derived from the tumor cell line 293.

Figure 28:
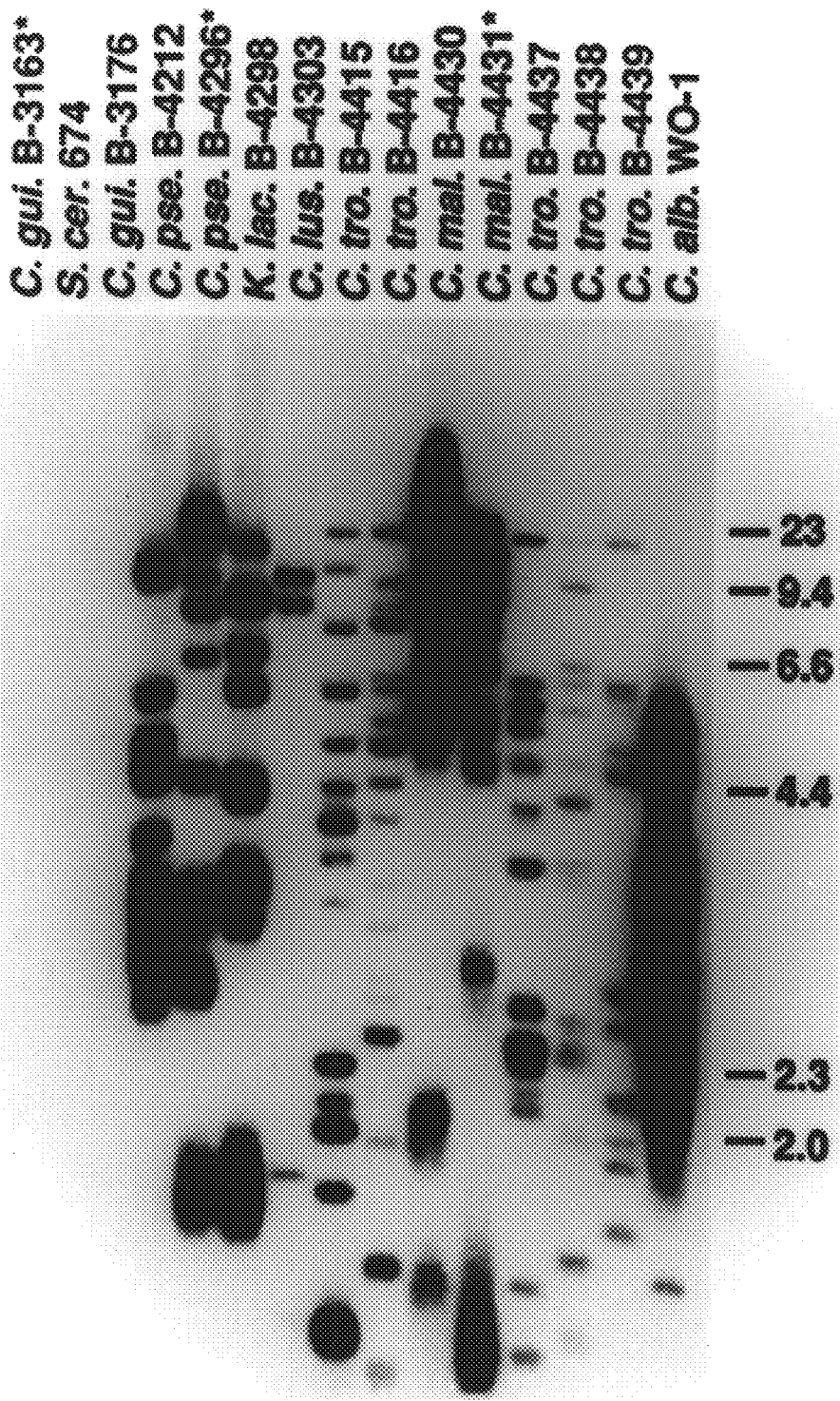

FIG. 28 shows hybridization of *C. albicans* telomeric repeats to genomic DNAs of a variety of other Candida species. Genomic DNAs of eight species of yeasts were digested with EcoRI, electrophoresed on 0.8% agarose, blotted, and then probed with a $^{32}$P-labeled telomeric fragment from C. albicans WO-1. Hybridization was carried out at 55° C. and washes were at the same temperature in Na$_2$HPO$_4$ at 200 mM Na$^+$ and 2% SDS. DNA size markers, measured in kilobase pairs (kb), are shown at the right. The species used here are *C. guillermondii, S. cerevisiae, C. pseudotropicalis, Kluyveromyces lactis, C. lusitaniae, C. maltosa, C. tropicalis,* and *C. albicans.* Asterisks indicate particular strains from which telomeres were cloned. Strains beginning with "B" are N.I.H. strains obtained from B. Wickes.

Figure 29A:
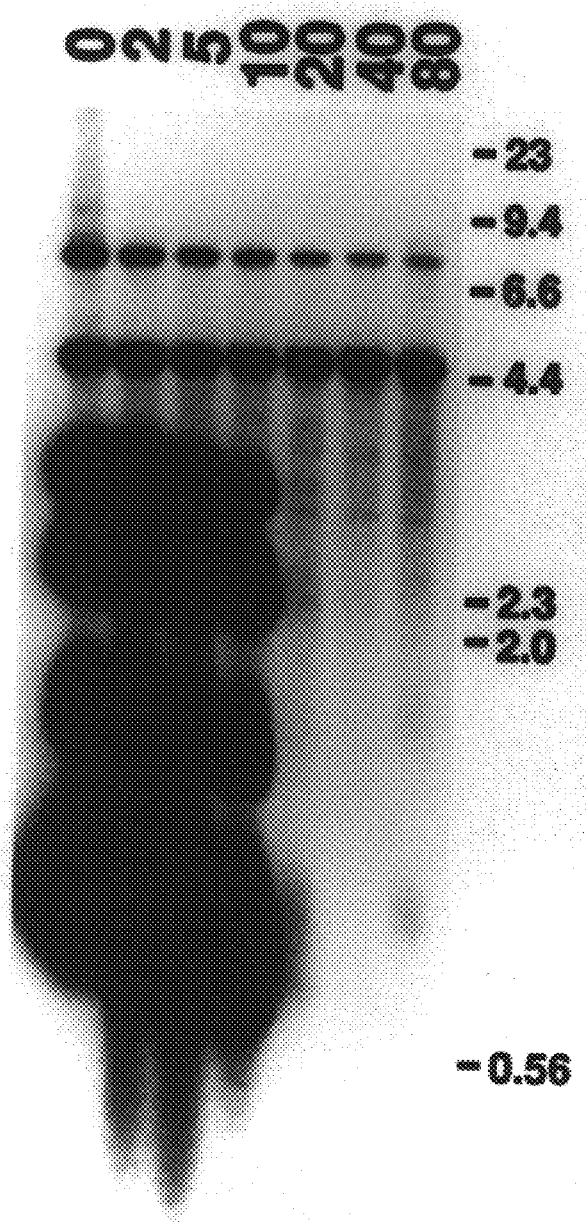
Figure 29B:
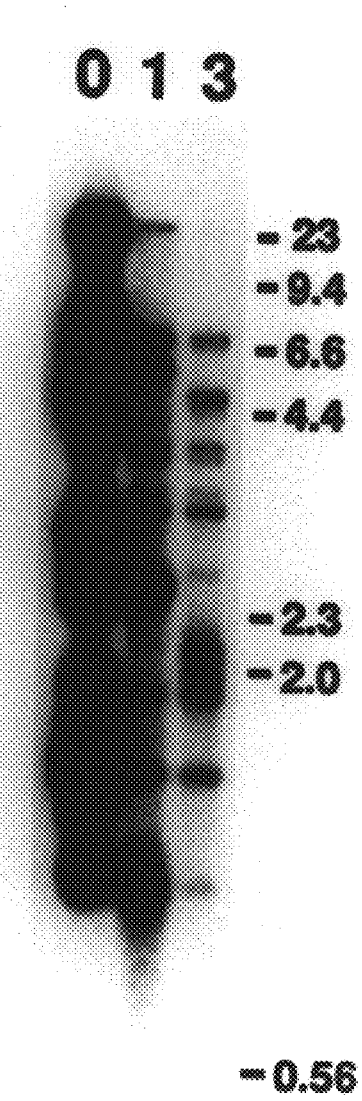

FIGS. 29A and 29B show Bal31 sensitivity of genomic copies of the tandem repeats in *K. lactis* ATCC 32143 (FIG. 29A) and *C. guillermondii* B-3163 (FIG. 29B). Uncut yeast genomic DNAs were incubated with Bal31 nuclease for increasing periods of time (given in minutes above each lane), then digested with EcoRI and electrophoresed on a 0.8% agarose gel, and blotted onto a nylon membrane. For *K. lactis,* probing was done with a $^{32}$P-kinased 25 base oligonucleotide identical in sequence to the *K. lactis* telomeric repeat shown in FIG. 30. Hybridization and washes were carried out at 49° C. For *C. guillermondii,* probing was done with $^{32}$P-labeled pCgui3, a pBluescript vector (Stratagene, LaJolla, Calif.) carrying a α-2 kb telomeric clone from *C. guillermondii.* Hybridizatijn and washing (in 200 mM Na$^+$) were carried out at 54° C. Most bands are gone by the 1 min. time point. Approximately three other bands are shortening but are not gone at 3 min. These latter bands presumably are homologous to the particular subtelomeric sequences present in pCgui3. DNA size markers (in kb) are indicated at the right of each panel.

FIG. 30 shows sequences of telomeric repeats from several budding yeast species. Specifically, telomere-enriched libraries were constructed from genomic DNA by standard methods. Uncut yeast genomic DNA was ligated to a blunt-ended linearized plasmid vector and then this ligated mix was digested with a restriction enzyme that cleaves both within the vector's polylinker and within a few kilobases of at least some of the putative telomeric ends of the species in question. No enzymatic pre-treatment was done to produce blunt-ends of the telomeres in the genomic DNA prior to the initial ligations. Plasmids were then recircularized with T4DNA ligase, and transformed into *E. coli* cells prior to screening for putative telomere clones by colony hybridization. The libraries from *C. maltosa, C. Rseudotrolicalis,* two strains of *C. tropicalis,* and *K. lactis* ATCC 32143, species which showed multiple bands that cross hybridized to the *C. albicans* telomeric repeat probe, were screened with this probe. A cloned *S. cerevisiae* telomere probe (repeat unit TG$_{2-3}$(GT)$_{1-3}$,) was used to screen the telomere—enriched library from *C. alabrata,* whose genomic DNA cross—hybridized with this, but not with the *C. albicans* telomeric repeat probe. *C. cuillermondii* DNA did not appreciably cross-hybridize with either the *C. albicans* or the *S. cerevisiae* telomeric probes at the stringencies tested. The telomere—enriched library from this species was screened using total genomic *C. guillermondii* DNA as a probe. This procedure can be used to identify all clones containing repetitive sequences and we reasoned that telomeres should be a reasonable percentage of the repetitive sequences found in telomere enriched libraries. Typically, a few hundred *E. coli* transformants were obtained for each small library and up to nine putative telomere clones were obtained from each. Nine repetitive DNA clones were obtained from *C. quillermondii,* three of which proved to be telomeric.

Figure 31A:
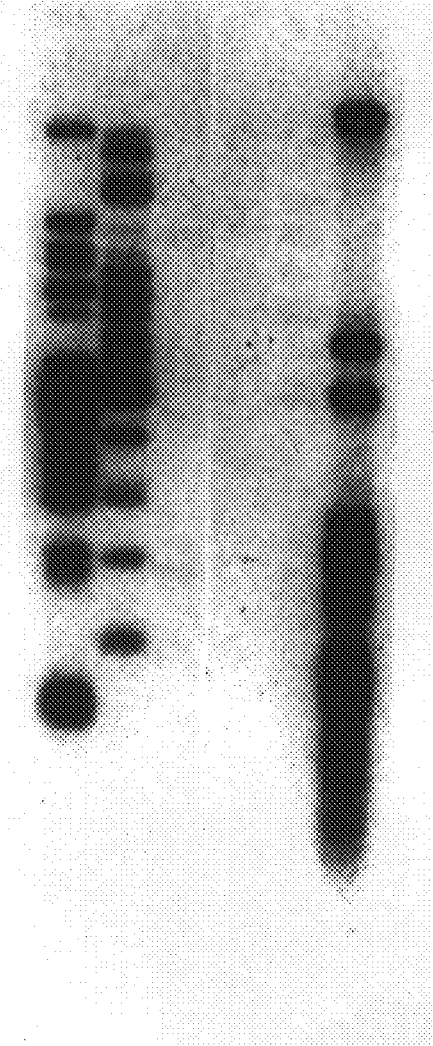
Figure 31B:
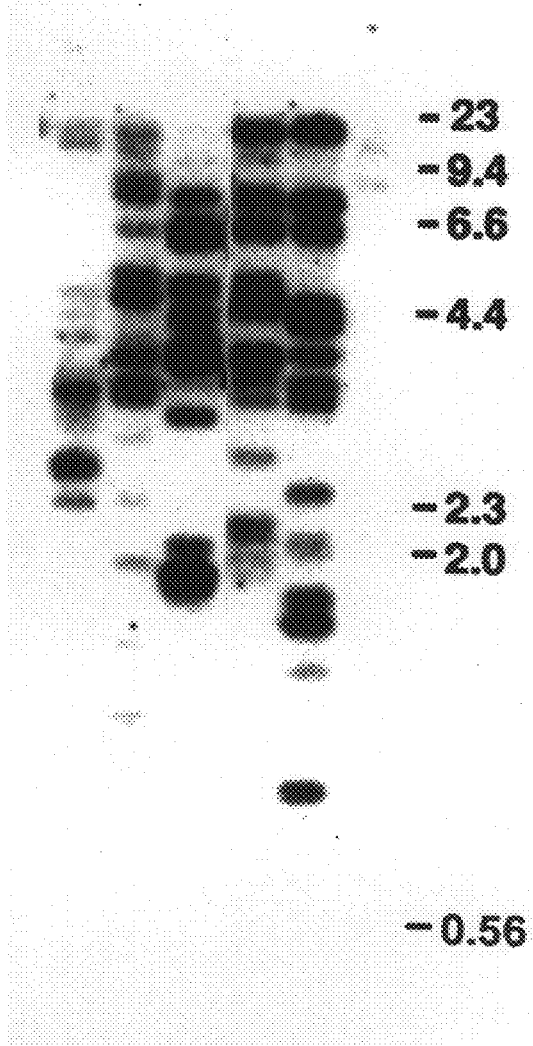

FIGS. 31A and 31B show two types of telomeric repeats present in certain *C. trovicalis* strains. Genomic DNAs from ten (only five here are shown) *C. troticalis* strains and *C. albicans* WO-1 were digested with ClaI, eletrophoresed on a 0.8% agarose gel, blotted, and probed with oligonucleotides specific to either the "AC form of *C. tropicalis* telomeric repeat (FIG. 31A) or to the "AA" form of repeat (FIG. 31B). Sequences of these two oligonucleotides are: 5'A<u>C</u>GGATGTCACG ("AC") and 5'GTGTA<u>A</u>GGATG ("AA") with the position of the dimorphic base shown underlined. Hybridization with the kinased "AC" probe was at 47° C., and hybridization with the "AA" probe at 24° C. Washes for both were in 2% SDS with 500 mM $Na^+$. The specificity of the "AA" probe is indicated by its failure to hybridize with the *C. albicans* telomeres, despite only one base mismatch and the fact that the *C. albicans* cells used here have much longer telomeres (and therefore many more telomeric repeats) than do *C. tropicalis* strains. The shortness of the *C. tropicalis* telomeres may explain why they appear to be particularly homogeneous in size, as is suggested by the relative sharpness of individual telomeric bands.

Figure 32:
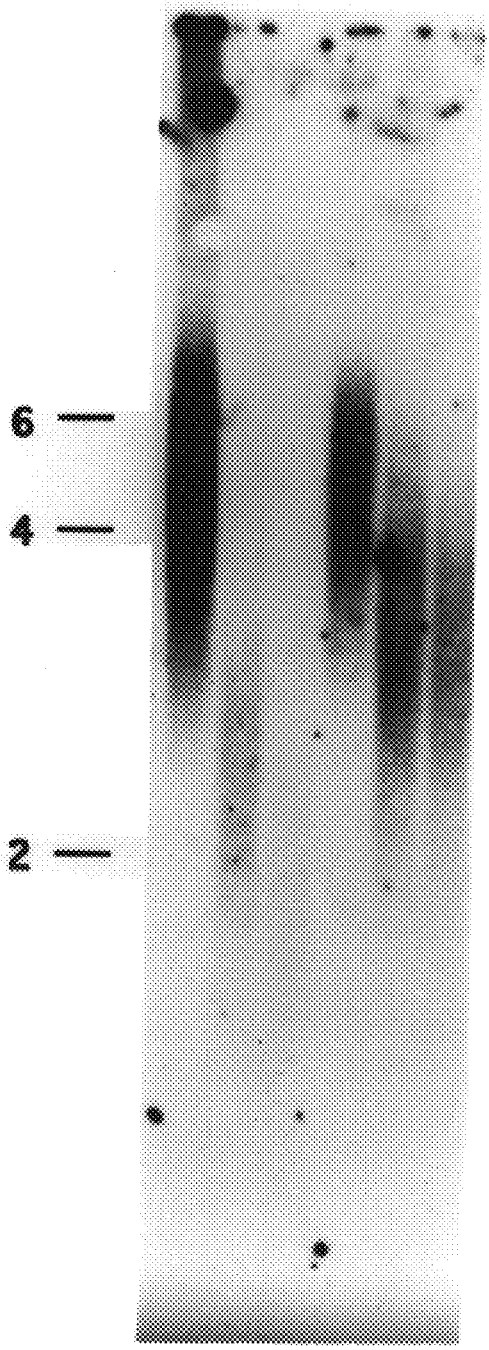

FIG. 32 shows a Southern blot of DNA isolated from JY cells hybridized to the $(TTAGGG)_3$ probe. Cells were treated over a 10 week period with either 10 $\mu$M ddG in 0.01% DMSO or medium with 0.01% DMSO only. Cells treated with ddG showed a marked decrease in mean telomere length consistant with the inhibition of telomerase activity.

Figures 33A, 33B:
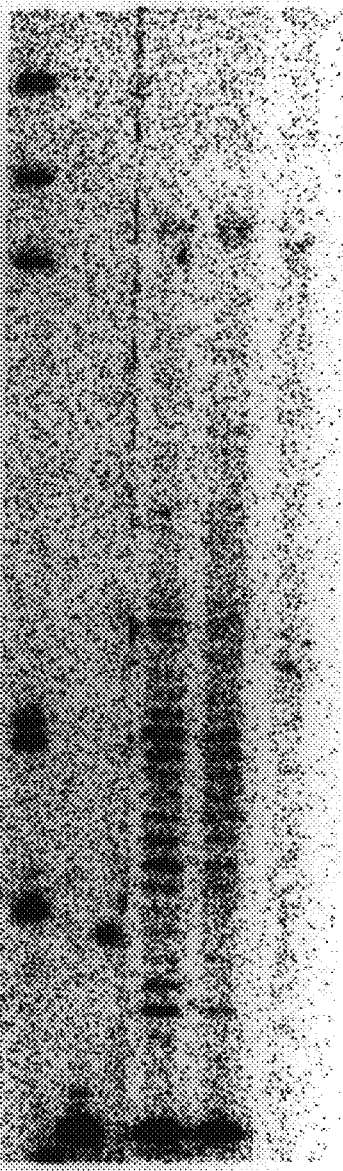

FIGS. 33A and 33B shows telomerase activity in cells from ascitic fluid. Specifically, S100 extracts were prepared, protein concentrations determined and telomerase activity assayed by incubating S100 extracts with an equal volume of reaction mixture containing buffer, telomere primer $(TTAGGG)_3$, $\alpha^{32}PdGTP$, TTP and dATP, at 30° C. for 1 hour. The reactions were terminated with RNase followed by deproteination with proteinase K. Unincorporated $\alpha^{32}PdGTP$ was removed using NICK SPIN columns (Pharmacia) according to the supplier's direction. Products were resolved on a sequencing gel and exposed to either a PhosphorImager screen (Molecular Dynamics). A ladder (L) and kinased $5'^{32}P(TTAGGG)_3$ (O) were run as markers.

FIGS. 33A and show telemerase assayed in S100 extracts with equal protein concentration (≈11 mg/ml) prepared from the control human cell line 293 CSH, a subline of 293 cell line, and from unfractionated ascitic fluid cells from patient Dem-1 and Rud-1. In lanes 1, 3 and 5 RNase was added to the extracts prior to addition of $\alpha^{32}PdGTP$.

FIG. 33B shows S100 extracts isolated and assayed for telomerase activity from the early passage cultures of cells from patients Pres-3 and Nag-1 compared to 293 cells. All extracts were assayed at a protein concentration of ≈2–3 mg/ml.

Telomeres and Telomerase

All normal diploid vertebrate cells have a limited capacity to proliferate, a phenomenon that has come to be known as the Hayflick limit or replicative senescence. In human fibroblasts, this limit occurs after 50–100 population doublings, after which the cells remain in a viable but non-dividing senescent state for many months. This contrasts to the behavior of most cancer cells, which have escaped from the controls limiting their proliferative capacity and are effectively immortal.

One hypothesis to explain the cause of cellular senescence concerns the role of the distal ends of chromosomes called telomeres. The hypothesis is that somatic cells lack the ability to replicate the very ends of DNA molecules. This results in a progressive shortening of the ends of the chromosomes until some function changes, at which time the cell loses the capacity to proliferate.

DNA polymerase synthesizes DNA in a 5' to 3' direction and requires a primer to initiate synthesis. Because of this, the "lagging strand" does not replicate to the very ends of linear chromosomes. The chromosome is thus shortened with every cell division. The ends of chromosomes are called telomeres, and are composed of long TTAGGG repeats. The enzyme telomerase can add TTAGGG repeats to the 3' end of the telomeric DNA, thus extending the DNA and preventing shortening.

Germline cells have long telomeres and active telomerase. Somatic cells lack telomerase activity, and their telomeres have been found to shorten with cell division both in vivo and in culture. Cancer cells are immortal, and have regained telomerase activity and thus can maintain their chromosome ends. Examples are provided below of definitive experiments which indicate that telomere shortening and telomerase activity are key factors in controlling cellular senescence and immortalization.

Methods

As noted above, the present invention concerns diagnosis and therapy associated with measuring telomeric length and manipulating telomerase-dependent extension or telomerase-independent shortening. While the invention is directed to humans, it may be applied to other animals, particularly mammals, such as other primates, and domestic animals, such as equine, bovine, avian, ovine, porcine, feline, and canine. The invention may be used in both therapy and diagnosis. In this case of therapy, for example, telomere shortening may be slowed or inhibited by providing DNA oligonucleotides by reactivating or introducing telomerase activity, or their functional equivalent, or indefinite proliferation can be reduced by inhibiting telomerase. In the case of diagnostics, one may detect the length of telomeres as to a particular chromosome or group of chromosomes, or the average length of telomeres. Diagnosis may also be associated with determining the activity of telomerase, or the presense of the components of the enzyme either on a protein or RNA level, in cells, tissue, and the like.

Information on the relative age, remaining proliferative capacity, as well as other cellular characteristics associated with telomere and telomerase status may be obtained with a wide variety of cell types and tissues, such as embryonic cells, other stem cells, somatic cells (such as hepatocytes in the context of cirrhosis), connective tissue cells (such as fibroblasts, chondrocytes, and osteoblasts), vascular cells (such as endothelial and smooth muscle cells), cells located in the central nervous system (such as brain astrocytes), and different neoplastic tissues, and parasitic pathogens where it is desirable to determine both the remaining replicative capacity of the hyperplastic cells and their capacity for immortal growth to predict growth potential.

Maintaining Telomere Length

Telomere length in cells in vitro or in vivo may be usefully maintained by a variety of procedures. These include those methods exemplified below. These examples, however, are not limiting in this invention since those in the art will recognize equivalent methods. It is expected that all the methods will be useful in manipulating telomere length now that applicant has demonstrated this experimentally. Such methods may be based upon provision of oligonucleotides or other agents which interact with telomeres to prevent shortening during cell division. In addition, the methods include treatment with agents which will include telomerase, or its equivalent activity, within a cell to prevent shortening. Finally, the methods also include modulation of gene expression associated with cell senescence.

Useful agents can be determined by routine screening procedures. For example, by screening agents which interact in an in vitro system with telomeres, and block loss of telomere ends, or aid increase in telomere length. Non-limiting examples of such methods are provided below. All that is necessary is an assay to determine whether telomere end shortening is reduced during cell division. The mechanism by which such agents act need not be known, so long as the desired outcome is achieved. However, by identifying useful target genes (e.g., the M2 mortality modulation gene(s)), antisense and equivalent procedures can be designed to more appropriately cause desired gene expression or non-expression (e.g., the de-repression of telomerase).

In a particular example (non-limiting in this invention) one can reduce the rate of telomere shortening, by providing a nucleic acid, e.g., DNA or RNA (including modified forms), as a primer to the cells. Such nucleic acid will usually include 2 to 3 repeats, more usually 2 repeats, where the repeats are complementary to the G-rich DNA telomere strand. Such oligonucleotides may be used to extend the proliferative capability of cells.

The oligonucleotides can be transferred into the cytoplasm, either spontaneously (i.e., without specific modification) or by the use of liposomes which fuse with the cellular membrane, or are endocytosed by employing ligands which bind to surface membrane protein receptors of the cell resulting in endocytosis. Alternatively, the cells may be permeabilized to enhance transport of the oligonucleotides into the cell, without injuring the host cells. Another way is to use a DNA binding protein, e.g., HBGF-1, which is known to transport an oligonucleotide into a cell. In this manner, one may substantially reduce the rate of telomere shortening from an average of about 50 bp per division, to an average of about 6–12 bp per division (see examples below), thus significantly extending the number of divisions occurring before induced cellular senescence.

By "senescence" is meant the loss of ability of a cell to replicate in the presence of normally appropriate replicative signals, and may be associated with the expression of degradative enzymes, such as collagenase. The term does not include quiescent cells which might be induced to replicate under appropriate conditions. This term is exemplified below in the examples, where the number of cell doubling prior to senescence is increased.

The above processes are useful in vivo. As already indicated, by using liposomes, particularly where the liposome surface carries ligands specific for target cells, or the liposomes will be preferentially directed to a specific organ, one may provide for the introduction of the oligonucleotides into the target cells in vivo. For instance, utilizing lipocortin affinity for phosphatidyl serine, which is released from injured vascular endothelial cells, the oligonucleotides may be directed to such site. Alternatively, catheters, syringes, depots or the like may be used to provide high localized concentrations. The introduction of such oligonucleotides into cells resulting in decreased senescence in response to cell division can have therapeutic effect.

The maintenance of telomere length has application in tissue culture techniques to delay the onset of cellular senescence. For instance, cell-based therapies which require the clonal expansion of cells for reintroduction into an autologous patient are limited to about 20–30 doublings. This invention allows, the expansion of cells in the case of gene therapy, both prior to genetic manipulation and then expansion of the manipulated cells, the maintenance of telomere length. This in turn allows normal cells to be cultivated for extended doublings in vitro. Experiments described below demonstrate the utility of this method in vitro, and demonstrate its applicability in vivo.

Critical shortening of telomeres leads to a phenomenon termed "crisis" or M2 senescence. See, Shay et al., 1992, supra. Among the cells in crisis, rare mutants may become immortalized in which M2 genes have altered regulation, and where expression of telomerase is reactivated and stabilizes the telomere length. An M2 regulatory gene may be modulated to provide a useful means of modulating telomere length and telomerase activity. The M2 genes may be identified by means of insertional mutagenesis into cells in M2 crisis utilizing a retrovirus. Cells wherein the M2 gene has been knocked out will then grow in response to the re-activation of telomerase, and such cells can supply a source or DNA from which to clone the M2 genes. This technique has yielded numerous cell clones in which the retrovirus has inserted into a common restriction fragment. The repression of the M2 regulatory gene(s) by antisense or other means can provide a means of activating telomerase reversibly, such that telomeres may be extended and then telomerase again repressed. In this manner, proliferative capacity may be extended with or without the addition of oligonucleotides to slow the telomere shortening. Such cells may then be used in cell-based therapies, such as bone marrow transplantation, reconstitution of connective tissue, and transplantation of early passage adrenal cortical cells, fibroblasts, epithelial cells, and myoblasts.

Telomerase Modulation

As discussed above, cancer cells contain telomerase activity and are thereby immortal. In addition, numerous types of parasitic pathogens are immortal and have active telomerase. Thus, it is useful to modulate (e.g., decrease) telomerase activity in such cells to impart a finite replicative life span. In contrast to the long telomeric tracts in normal human cells, tracts of telomeric DNA in protozoan cells, fungal cells, and some parasitic worms, as well as many cancer cells, are typically shorter. This makes these cells more vulnerable to telomerase inhibitors than normal human cells (e.g. germ line cells).

Thus, inhibition or induction of telomerase has applications in various situations. By inhibiting telomerase intracellularly, one may reduce the ability of cancer cells to proliferate. Telomerase may be competitively inhibited by adding synthetic agents, e.g., oligonucleotides comprising 2 or more, usually not more than about 50 repeats, of the telomeric motif of the 5'-3' G-rich strand (the strand which acts as the template). The oligonucleotides may be synthesized from natural or unnatural units, e.g., the derivatives or carbon derivatives, where a phosphate-oxygen is substituted with sulfur or methylene, modified sugars, e.g., arabinose, or the like. As discussed above, other equivalent agents may also be used to inhibit or cause expression of telomerase activity.

The oligonucleotides may be introduced as described above so as to induce senescence in the immortalized cells, in culture and in vivo. Where growing cells in culture, where one wishes to prevent immortalized cells from overgrowing the culture, one may use the subject oligonucleotides to reduce the probability of such overgrowth. Thus, by maintaining the oligonucleotides in the medium, they will be taken up by the cells and inhibit telomerase activity. One may provide for linkage to the telomeric sequence with a metal chelate, which results in cleavage of nucleic acid sequences. Thus, by providing iron chelate bound to the telomeric motif, the telomerase RNA will be cleaved, so as to be non-functional. Alternatively, a reactive group may be coupled to the oligonucleotide that will covalently bind to telomerase, or the 3' residue may be made to be dideoxy so as to force chain termination.

Alternatively, one may introduce a ribozyme, having 5' and 3'-terminal sequences complementary to the telomerase RNA, so as to provide for cleavage of the RNA. In this way, the telomerase activity may be substantially inhibited, so as to result in a significant limitation of the ability of the cancer cells to proliferate. Telomerase may also be inhibited by the administration of an M2 regulator gene product. By modulating the expression of any of the proteins directly regulating telomerase expression, one may also modulate cellular telomerase activity.

Alternatively, one may use a screening assay utilizing human or tetrahymena telomerase to screen small molecules e.g., nucleoside analogs like ava-G, ddG, AZT, and the like and RNA and DNA processing enzyme inhibitors, alkylating agents, and various potential anti-tumor drugs. These may then be further modified.

The nucleic acid sequences may be introduced into the cells as described previously. Various techniques exist to allow for depots associated with tumors. Thus, the inhibiting agents or nucleic acids may be administered as drugs, since they will only be effective only in cells which include telomerase. Since for the most part, human somatic cells lack telomerase activity they will be unaffected. Some care may be required to prevent entry of such drugs into germ cells, which may express telomerase activity.

The subject compositions can therefore be used in the treatment of neoplasia wherein the tumor cells have acquired an immortal phenotype through the inappropriate activation of telomerase, as well as various human and veterinary parasitic diseases; including human protozoal pathogens such as; amebiasis from Entamoeba histolytica, amebic meningoencephalitis from the genus Naegleria or Acanthamoeba, malaria from *Plasmodium vivax, Plasmodium ovale, Plasmodium malariae,* and *Plasmodium falciparum,* Leishmaniasis from such protozoa as *Leishmania donovani, Leishmania infantum, Leishmania chagasi, Leishmania tropica, Leishmania major, Leishmania aethiopica, Leishmania mexicana,* and *Leishmania braziliensis,* Chagas' disease from the protozoan *Trypanosoma cruzi,* sleeping sickness from *Trypanosoma brucei, Trypanosoma gambiense,* and *Trypanosoma rhodesiense,* Toxoplasmosis from *Toxoplasma gondii,* giardiasis from *Giardia lamblia,* cryptosporidiosis from *Cryptosporidium parvum,* trichomoniasis from *Trichomonas vaginalis, Trichomonas tenax, Trichomonas hominis,* pneumocystis pneumonia from *Pneumocystis carinii,* bambesosis from *Bambesia microti, Bambesia divergens,* and *Bambesia boris,* and other protozoans causing intestinal disorders such as *Balantidium coli* and *Isospora belli.* Telomerase inhibitors would also be useful in treating certain helminthic infections including the species: *Taenia solium, Taenia saginata, Diphyllobothrium lata, Echinococcus granulosus, Echinococcus multilocularis, Hymenolepis nana, Schistosoma mansomi, Schistosoma japonicum, Schistosoma hematobium, Clonorchis sinensis, Paragonimus westermani, Fasciola hepatica, Fasciolopsis buski, Heterophyes heterophyes, Enterobius vermicularis, Trichuris trichiura, Ascaris lumbricoides, Ancylostoma duodenale, Necator americanus, Strongyloides stercoralis, Trichinella spiralis, Wuchereria bancrofti, Onchocerca volvulus, Loa loa, Dracunculus medinensis,* and fungal pathogens such as: *Sporothrix schenckii, Coccidioides immitis, Histoplasma capsulatum, Blastomyces dermatitidis, Paracoccidioides brasiliensis, Candida albicans, Cryptococcus neoformans, Aspergillus fumigatus, Aspergillus flavus,* fungi of the genera Mucor and Rhizopus, and species causing chromomycosis such as those of the genera Phialophora and Cladosporium. and important veterinary protozoal pathogens such as: *Babesia caballi, Babesia canis, Babesia equi, Babesia felis, Balantidium coli, Besnoitia darlingi, Eimeria acervulina, Eimeria adenoeides, Eimeria ahsata, Eimeria alabamensis, Eimeria auburnensis, Eimeria bovis, Eimeria brasiliensis, Eimeria brunetti, Eimeria canadensis, Eimeria cerdonis, Eimeria crandallis, Eimeria cylindrica, Eimeria debliecki, Eimeria despersa, Eimeria ellipsoidalis, Eimeria fauvei, Eimeria gallopavonis, Eimeria gilruthi, Eimeria granulosa, Eimeria hagani, Eimeria illinoisensis, Eimeria innocua, Eimeria intricata, Eimeria leuskarti, Elmeria maxima, Elmeria meleagridis, Eimeria meleagrimitis, Eimeria mitis, Eimeria mivati, Eimeria necatrix, Eimeria neodebliecki, Eimeria ninakohlyakimorae, Eimeria ovina, Eimeria pallida, Eimeria parva, Eimeria perminuta, Eimeria porci, Eimeria praecox, Eimeria punctata, Eimeria scabra, Eimeria spinoza, Eimeria subrotunda, Eimeria subsherica, Eimeria suis, Eimeria tenella, Eimeria wyomingensis, Eimeria zuernii, Endolimax gregariniformis, Endolimax nana, Entamoeba bovis, Entamoeba gallinarum, Entamoeba histolytica, Entamoeba suis, Giardia bovis, Giardia canis, Giardia cati, Giardia lamblia, Haemoproteus meleagridis, Hexamita meleagridis, Histomonas meleagridis, Iodamoeba buetschili, Isospora bahiensis, Isospora burrowsi, Isospora canis, Isospora fells, Isospora ohioensis, Isospora rivolta, Isospora suis, Klossiella equi, Leucocytozoon caallergi, Leucocytozoon smithi, Parahistomonas wenrichi, Pentatrichomonas hominis, Sarcocystis betrami, Sarcocystis bigemina, Sarcocystis cruzi, Sarcocystis fayevi, hemionilatrantis, Sarcocystis hirsuta, Sarcocystis miescheviana, Sarcocystis muris, Sarcocystis ovicanis, Sarcocystis tenella, Tetratrichomonas buttreyi, Tetratrichomonas gallinarum, Theileria mutans, Toxoplasma gondii, Toxoplasma hammondi, Trichomonas canistomae, Trichomonas gallinae, Trichomonas felistomae, Trichomonas eberthi, Trichomonas equi, Trichomonas foetus, Trichomonas ovis, Trichomonas rotunda, Trichomonas suis,* and *Trypanosoma melophagium.* In addition, they can be used for studying cell senescence, the role of telomeres in the differentiation and maturation of cells from a totipotent stem cell, e.g., embryonic stem cells, or the like, and the role of telomerase in spermatogenesis.

Telomere Length

Procedures for measuring telomere length are known in the art and can be used in this invention. Typically, restriction endonuclease digestion is used (with enzymes which do not cleave telomeric DNA), and the length of the fragment having detectable telomere DNA is separated according to molecular weight by agarose gel electrophoresis. Given that the DNA sequence of a telomere is known, detection of such DNA is relatively easy by use of specific oligonucleotides. Examples of these methods are provided below.

For diagnosis, in detection of the telomeric length, one may study just a particular cell type, all cells in a tissue (where various cells may be present), or subsets of cell types, and the like. The preparation of the DNA having such telomeres may be varied, depending upon how the telomeric length is to be determined.

Conveniently, the DNA may be isolated in accordance with any conventional manner, freeing the DNA of proteins by extraction, followed by precipitation. Whole genomic DNA may then be melted by heating to at least about 80° C., usually at least about 94° C., or using high salt content with chaotropic ions, such as 6×SSC, quanidinium thiocyanate, urea, and the like. Depending upon the nature of the melting process, the medium may then be changed to a medium which allows for DNA synthesis.

(a) DNA Synthesis

In one method, a primer is used having at least about 2 repeats, preferably at least about 3 repeats of the telomeric sequence, generally not more than about 8 repeats, conveniently not more than about 6 repeats. The primer is added to the genomic DNA in the presence of only 3 of the 4 nucleoside triphosphates (having the complementary nucleosides to the protruding or G-rich strand of a telomere, e.g., A, T and C for human chromosomes), dATP, dTTP and dCTP. Usually at least the primer or at least one of the triphosphates is labeled with a detectable label, e.g., a radioisotope, which label is retained upon incorporation in the chain. If no label is used, other methods can be used to detect DNA synthesis. The primer is extended by means of a DNA polymerase, e.g., the Klenow fragment of DNA polymerase I, T7 DNA polymerase or Taq DNA polymerase The length of the extended DNA can then be determined by various techniques, e.g., those which separate synthesized DNA on the basis of its molecular weight, e.g., gel electrophoresis. The DNA synthesized may then be detected based on the label, e.g., counts incorporated per $\mu$g of DNA, where the counts will be directly proportional to telomere length. Thus, the measure of radioactivity in relation to the amount of DNA will suffice to quantitate telomere length.

If desired, telomeres of known length may be used as standards, whereby a determination of radioactivity may be read off a standard curve as related to telomere length. Instead, one may prepare tissues where individual cells may be assayed for relative telomere length by in situ hybridization. In this approach, for example, the primer is labeled with a detectable label, usually biotin or digoxygenin. Following annealing to prepared tissue sections or cells, the label is revealed histochemically, usually using autoradiography (if the label were radioactive), using avidin/streptavidin (if the label were biotin) or using antidigoxygenin antibodies (if the label were digoxygenin). The amount of signal per cell is proportional to the number of telomeric repeats, and thus to the telomere length. This can be quantitated by microfluorometry or analogous means, and compared to the signal from standard cells of known telomere length to determine the telomere length in the test sample.

(b) Restriction Endonuclease Digestion

Alternatively, one may use primers which cause covalent cross-linking of the primer to telomere DNA. In this situation, one may totally digest the DNA with restriction endonucleases which have 4 base recognition sites, which results in the production of relatively short fragments of DNA, except for telomeric DNA which lacks the recognition site. Restriction endonucleases which may find use include AluI, HinfI, MspI, RsaI, and Sau3A, where the restriction endonucleases may be used individually or in combination. After digestion of the genomic DNA, the primer may be added under hybridizing conditions, so as to bind to the protruding chain of the telomeric sequence. By providing for two moieties bound to the primer, one for covalent bonding to the telomeric sequence and the other for complex formation with a specific binding pair member, one can then provide for linking of a telomeric sequence to a surface. For example, for covalent bonding to the telomeric sequence, psoralen, or isopsoralen, may be linked to one of the nucleotides by a bond or chain and upon UV-radiation, will form a bridge between the primer and the telomere.

The specific binding pair member will normally be a hapten, which binds to an appropriate complementary member, e.g., biotin and strept/avidin, trinitrobenzoic acid and anti-trinitrobenzamide antibody, or methotrexate and dihydrofolate reductase. Rather than having the moiety for covalent bonding covalently bonded to the primer, one may add a compound into the medium which is intercalatable into the nucleic acid, so as to intercalate between double-stranded nucleic acid sequences. In this manner, one may achieve the same purpose. Use of a substantial excess of the intercalatable compound will cause it to also intercalate into other portions of DNA which are present. Various modifications of this process may be achieved, such as size separation, to reduce the amount of label containing DNA.

The specific binding pair member may be used for separation of telomeric DNA free of contaminating DNA by binding to the complementary pair member, which may be present on beads, on particles in a column, or the like. In accordance with the nature of the separation, the covalently bonded telomere strand may now be purified and measured for size or molecular weight. Again, if desired, standards may be employed for comparison of distribution values.

The specific binding pair member hapten can be present at the 5'-terminus of the primer or at intermediate nucleotides. Specifically, biotin-conjugated nucleotides are generally available and may be readily introduced into synthetic primer sequences in accordance with known ways.

The above-described techniques can also be used for isolating and identifying DNA contiguous to the telomere.

(c) Average Telomere Length

In methods of this invention it may be useful to determine average telomere length by binding a primer to a telomere prior to separation of the telomeric portion of the chromosomes from other parts of the chromosomes. This provides a double-stranded telomeric DNA comprising the telomeric overhang and the primer. A reaction may then be carried out which allows for specific identification of the telomeric DNA, as compared to the other DNA present. The reaction may involve extension of the primer with only 3 of the nucleotides (dNTPs), using a labeled nucleotide, covalent bonding of the primer to the telomeric sequence, or other methods which allow for separation of the telomeric sequence from other sequences. The length of the synthesized DNA detected then represents the average telomere length.

Telomere length can also be measured directly by the "anchored terminal primer" method. In this method, the 3' ends of genomic DNA are first "tailed" with dG nucleotides using terminal transferase. Telomeres, which are known to have 3' overhangs, then would have one of the three follwing conformations:

...5'TTAGGGTTAGGGTTAGGGGGGGGGGG...3'
...5'TTAGGGTTAGGGTTGGGGGGGGGGGG...3'
...5'TTAGGGTTAGGGTGGGGGGGGGGGGG...3'

Other ends of the genomic DNA which were generated by shearing would be tailed with G's but would not have the adjacent TTAGGG repeats. Thus, a mix of the following 3 biotinylated oligonucleotides would anneal under stringent conditions specifically to all possible telomere ends:

5'B-CCCCCCCCTAACCCTA
5'B-CCCCCCCCAACCCTAA Oligo Mix [M]
5'B-CCCCCCCCACCCTAAC

Oligo mix [M] consists of 16-base oligonucleotides with 5' biotin (B), but other combinations of 5'-C-tracts adjacent to the C-rich telomeric repeats could provide specific hybridization to the 3' end of the native telomeres.

Extension of the primer with a DNA polymerase such as Klenow, DNA Polymerase I, or Taq polymerase, in the presence of dCTP, DATP, dTTP (no dGTP, and with or without ddGTP) would stabilize the primer-template configuration and allow selection, using streptavadin beads, of the terminal fragments of DNA containing the telomeric DNA. The length of primer extension using Klenow (monitored with labeled nucleotides) would indicate the length of the telomeric (GTR) 3' overhang, since Klenow lacks 5'-3' exonuclease activity and would stall at the CTR. This length distribution could be indicative of the level of telomerase activity in telomerase-positive cells (i.e., longer extensions correspond to greater telomerase activity). In contrast, extension of the primer with DNA polymerase I, an enzyme with 5'-3' exonuclease activity as well as polymerase activity, would allow extension through the CTR until C's are encountered in the template strand (subtelomeric to the GTR). The length distribution of this reaction, monitored by labeled nucleotides, would be indicative of the length distribution of the GTR. In both cases, labeled products arising from biotinylated primers are selected with the streptavadin beads to reduce the signal from non-specific priming. Alternatively, re-priming and extension of the tailed chromosome end can take place after selection of the partially extended products with the streptavadin beads, and after denaturation of the C-rich strand from the duplex.

Experiments have confirmed that the G-tailing of chromosome ends can be carried out efficiently such that about 50 G residues are added per end, that the priming with the junction oligonucleotide mix is highly specific for the tailed telomeric ends, and that streptavadin beads select specifically for the extension products that originate from the biotinylated primers and not from other fortuitous priming events. The length of the extension products under the conditions outlined above thus provide a direct estimate of the length of the terminal TTAGGG repeat tract. This information is especially important in cases where stretches of TTAGGG repeats occur close to but not at the termini of chromosomes. No other method described to date is capable of distinguishing between the truly terminal TTAGGG repeats and such internal repeats.

The determination of telomere length as described above can be associated with a variety of conditions of diagnostic interest. Following telomere length in tumor cells provides information regarding the proliferative capacity of such cells before and following administration of inhibitors of telomerase (or other treatments which destabilizes the telomere length as discussed above). It also provides a means of following the efficacy of any treatment and providing a prognosis of the course of the disease.

Where diseased tissue is involved, the native tissue can be evaluated as to proliferative capability. By "proliferative capability" is meant the inherent ability of a cell or cells in a tissue to divide for a fixed number of divisions under normal proliferation conditions. That is, the "Hayflick" number of divisions, exemplified below in the examples. Thus, despite the fact that the tissue may have a spectrum of cells of different proliferative capability, the average value will be informative of the state of the tissue generally. One may take a biopsy of the tissue and determine the average telomeric length. Using the value, one may then compare the value to average normal healthy tissue as to proliferative capability, particularly where the tissue is compared to other tissue of similar age.

In cases of cellular diseases, such as liver disease, e.g., cirrhosis, or muscle disease, e.g., muscular dystrophy, knowledge of the proliferative capability can be useful in diagnosing the likely recuperative capability of the patient. Other situations involve injury to tissue, such as in surgery, wounds, burns, and the like, where the ability of fibroblasts to regenerate the tissue will be of interest. Similarly, in the case of loss of bone, osteoarthritis, or other diseases requiring reformation of bone, renewal capability of osteoblasts and chondrocytes will be of interest.

While methods are described herein to evaluate the proliferative capacity of a tissue by taking an average measure of telomere length it is noted that the tissue may have a spectrum of cells of different proliferative capability. Indeed, many tissues, including liver, regenerate from only a small number of stem cells (less than a few percent of total cells). Therefore, it is useful in this invention to use in situ hybridization (such as with fluorescently labeled telomeric probes), to identify and quantitate such stem cells, and/or the telomeric status of such cells on an individual, rather than collective basis. This is performed by measuring the fluorescent intensity for each individual cell nucleus using, e.g., automated microscopy imaging apparatus. In addition to in situ hybridization, gel electrophoresis is useful in conjunction with autoradiography to determine not only the average telomere length in cells in a tissue sample, but also the longest telomere lengths (possibly indicating the presence of stem cells) and the size distribution of telomere lengths (which may reflect different histological cell types within a tissue, see FIGS. 10–11). Thus, the autoradiogram, or its equivalent provides useful information as to the total telomere status of a cell, or group of cells. Each segment of such information is useful in diagnostic procedures of this invention.

d) Modified Maxam-Gilbert Reaction

The most common technique currently used to measure telomere length is to digest the genomic DNA with a restriction enzyme with a four-base recognition sequence like HinfI, electrophorese the DNA and perform a Southern blot hybridizing the DNA to a radiolabeled $(TTAGGG)_3$ probe. A difficulty with this technique is that the resulting terminal restriction fragments (TRFs) contain a 3–5 kbp stretch of subtelomeric DNA that lacks restriction sites and thereby adds significantly to the size of the measured telomere length. Another approach to eliminate this DNA and improve accuracy of telomere length assays utilizes the fact that this subtelomeric DNA contains G and C residues in both strands, and thus should be cleaved under conditions that cause breaks at G residues. In contrast, DNA composed exclusively of telomeric repeats will have one strand lacking G residues, and this strand should remain intact under G-cleavage conditions. The Maxam-Gilbert G-reaction uses piperidine to cleave guanine residies that have been methylated by dimethylsulfate (DMS) treatment. Although the original conditions of the Maxam-Gilbert G-reaction (treatment in 1M piperidine for 30 min. at 90° C.) breaks unmethylated DNA into fragments of 1–2 kbp and is thus non-specific, milder conditions (0.1M piperidine for 30 min. at 37° C.) leave untreated DNA intact. The DNA is therefore treated with DMS and piperidine as described above, precipitated with ethanol, electrophoresed, and hybridized on a Southern blot to the a $(TTAGGG)_3$ probe. The results of such a test are shown in FIG. 26.

Telomerase Activity

Telomerase activity is useful as a marker of growth potential, particularly as to neoplastic cells, or progenitor cells, e.g., embryonic stem cells. Human telomerase activity may be determined by measuring the rate of elongation of an appropriate repetitive sequence (primer), having 2 or more, usually 3 or more, repeats of the telomere unit sequence, TTAGGG. The sequence is labeled with a specific binding pair member at a convenient site, e.g., the 5'-terminus, and the specific binding pair member allows for separation of extended sequences. By using one or more radioactive nucleoside triphosphates or other labeled nucleoside triphosphate, as described previously, one can measure the incorporated radioactivity as cpm per unit weight of DNA as a function of unit of time, as a measure of telomerase activity. Any other detectable signal and label may also be used, e.g., fluorescein.

The activity may be measured with cytoplasmic extracts, nuclear extracts, lysed cells, whole cells, and the like. The particular sample which is employed and the manner of pretreatment will be primarily one of convenience. The pretreatment will be carried out under conditions which avoids denaturation of the telomerase, so as to maintain the telomerase activity. The primer sequence will be selected or labeled so as to allow it to be separated from any other DNA present in the sample. Thus, a haptenic label may be used to allow ready separation of the elongated sequence, which represents the telomerase activity of the sample. The nucleoside triphosphates which may be employed may include at least one nucleoside triphosphate which is labeled. The label will usually be radiolabel, but other labels may also be present. The labels may include specific binding pair members, where the reciprocal member may be labeled with fluorescers, enzymes, or other detectable label. Alternatively, the nucleoside triphosphates may be directly labeled with other labels, such as fluorescent labels.

The sequence elongation usually will be carried out at a convenient temperature, generally from about 20° C. to 40° C., and for a time sufficient to allow for at least about 100 bp to be added on the average to the initial sequence, generally about 30–90 minutes. After the incubation time to allow for the telomerase catalyzed elongation, the reaction may be terminated by any convenient means, such as denaturation, e.g., heating, addition of an inhibitor, rapid removal of the sequence by means of the label, and washing, or the like. The separated DNA may then be washed to remove any non-specific binding DNA, followed by a measurement of the label by any conventional means.

The determination of telomerase activity may be used in a wide variety of ways. It can be used to determine whether a cell is immortalized, e.g., when dealing with tissue associated with neoplasia. Thus, one can determine at the margins of a tumor, whether the cells have telomerase activity and may be immortalized. The presence and activity of the telomerase may also be associated with staging of cancer or other diseases. Other diagnostic interests associated with telomerase include measurement of activity as an assay for efficacy in treatment regimens designated to inhibit the enzyme.

Other techniques for measuring telomerase activity can use antibodies specific for the telomerase protein, where one may determine the amount of telomerase protein in a variety of ways. For example, one may use polyclonal antisera bound to a surface of monoclonal antibody for a first epitope bound to a surface and labeled polyclonal antisera or labeled monoclonal antibody to a second epitope dispersed in a medium, where one can detect the amount of label bound to the surface as a result of the telomerase or subunit thereof bridging between the two antibodies. Alternatively, one may provide for primers to the telomerase RNA and using reverse transcriptase and the polymerase chain reaction, determine the presence and amount of the telomerase RNA as indicative of the amount of telomerase present in the cells.

The following examples are offered by way of illustration and not by way of limitation.

EXAMPLES

The following are examples of specific aspects of the invention to merely illustrate this invention to those in the art. These examples are not limiting in the invention, but provide an indication of specific methodology useful in practice of the invention. They also provide clear indication of the utility of the invention and of the correlation between telomere length, telomerase activity and cellular senescence. Such correlation indicates to those in the art the breadth of the invention beyond these examples.

Example 1

Telomere Length and Cell Proliferation

The effects of telomere length modulation on cellular proliferation were studied. An average of 50 bp are lost per cell division in somatic cells. The telomere end is thought to have a single-stranded region as follows (although the amount of overhang is unknown):

5'TTAGGGTTAGGGTTAGGGTTAGGGT-
TAGGGTTAGGGTTAGGGTTAGGGTTAG GGTTA GGG
3'AATCCCAATCCC
(Seq. ID No. 1)

Applicant postulated that loss of this single-stranded overhang should be significantly slowed if cells were provided with a synthetic oligonucleotide of the sequence CCCTAACCCTAA (Seq. ID No. 2). This oligonucleotide should hybridize to the exposed single-stranded region, and serve as a primer for DNA synthesis by the normal DNA polymerase present in somatic cells. In this way, rather than shortening by an average of 50 bp per division, the telomeres may only shorten by a lesser amount per division, thus significantly extending the number of divisions required before telomere shortening induced cellular senescence. This hypothesis was tested by measuring both the change in proliferative lifespan and rate of telomere shortening in cultured cells treated with this indicated oligonucleotide, versus control oligonucleotides.

The efficacy of the CTO-12 oligonucleotide (5'-CCCTAACCCTAA-3' Seq. ID No. 2) to reduce telomere shortening associated with cellular senescence (FIG. 1) was studied using target cells cultured under standard cell culture conditions in minimal essential medium supplemented with 10% fetal calf serum. The cells were subcultivated every four days by trypsinization upon reaching confluency and were fed new medium at subcultivation or every two days, whichever came first. Cells at various population doubling levels were seeded at 10,000 cells per well and fed medium containing oligonucleotides at various concentrations. oligonucleotides studied were the cytidine-rich terminal oligonucleotide (CTO-12), guanidine-rich terminal oligonucleotide-12 bp (GTO-12, having the sequence 5'-TTAGGGTTAGGG-3' (Seq. ID No. 3)), and a 12 base pair randomer with a random nucleotide in every position. As an additional control, cells were fed identical medium without oligonucleotide. Cells were fed oligonucleotide every 48 hours from 10× stocks. (Such oligonucleotides may be modified to enhance stability, e.g., with phosphorothioates, dithioate and 2-O-methyl RNA.) In the case of phosphorothioates it would be desirable to use longer CTO primers such as 5'-CCCTAACCCTAACCCT-3', 5'-CCCTAACCCTAACCCTAA-3', or 5'-CCCTAACCCTAACCCTAACC-3'.

Figure 1:
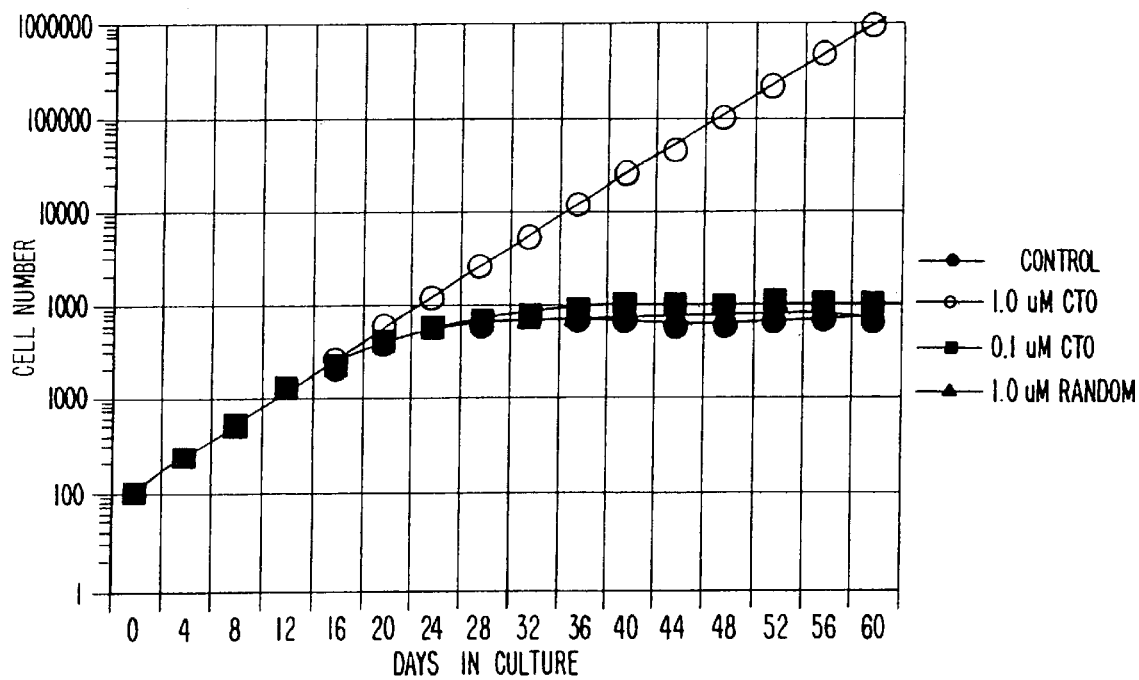
FIGS. 1–3 are graphs where the cell type and/or the culture conditions are varied, plotting days in culture (horizontal axis) length versus cell number (vertical axis).

Specifically, IMR-90 human lung fibroblasts with a proliferative capacity of approximately 55 population doubling (PD) were seeded at PD45 at 10,000 cells per well in a 48 well tissue culture dish, and fed medium only or medium supplemented with CTO-12 (at 1.0 $\mu$M and 0.1 $\mu$M) and 12 base pair randomer at 1.0 $\mu$N. As shown in FIG. 1, cells grown in medium without oligonucleotide, or with CTO-12 at less than 1.0 $\mu$M or with oligonucleotide of random sequence reached replicative senescence in a similar fashion at about 52 population doubling. Cells fed the CTO-12 oligonucleotide at 1.0 $\mu$M, however, continued to proliferate for approximately 10 doubling more than control cells.

Example 2
Inhibition of Telomerase in Cancer Cells

One way by which cancer cells are able to escape cellular senescence is by regaining telomerase activity, which permits them to maintain the length of their telomeres in the face of multiple rounds of cell division. The enzyme telomerase contains an RNA complementary to TTAGGG, which allows it to recognize the telomeres and extend them by the addition of additional TTAGGG repeats. In fact, one assay for telomerase uses a TTAGGGTTAGGG primer and measures the ability of cell extracts to synthesis a ladder of 6 bp additions to this substrate. Telomerase activity in cancer cells is likely to be present in limiting amounts since telomere length is relatively stable (thus only about 50 bp per telomere are added, so that lengthening and shortening are balanced).

Applicant hypothesized that feeding cells a synthetic TTAGGGTTAGGG oligonucleotide (Seq. ID No. 3) should competitively inhibit the ability of telomerase to elongate chromosome ends, and thus should lead to telomere shortening and senescence in cancer cells. Since somatic cells lack telomerase activity, the effects of this treatment should be strictly limited to cancer cells and the germ line.

Figure 2:
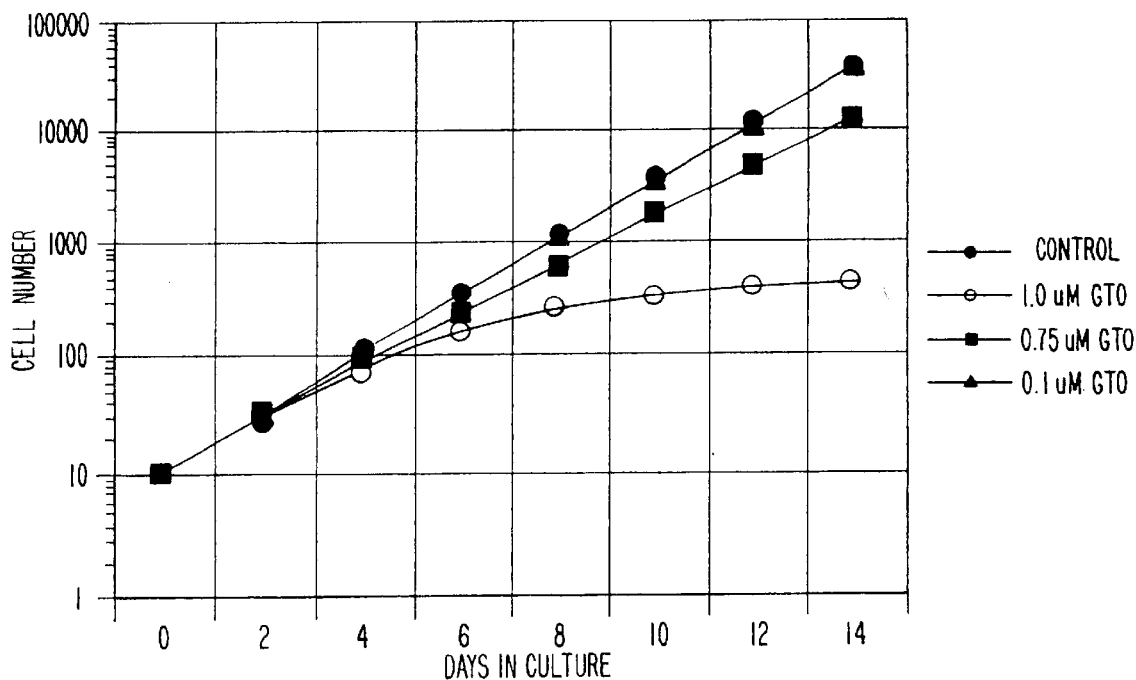
Figure 3:
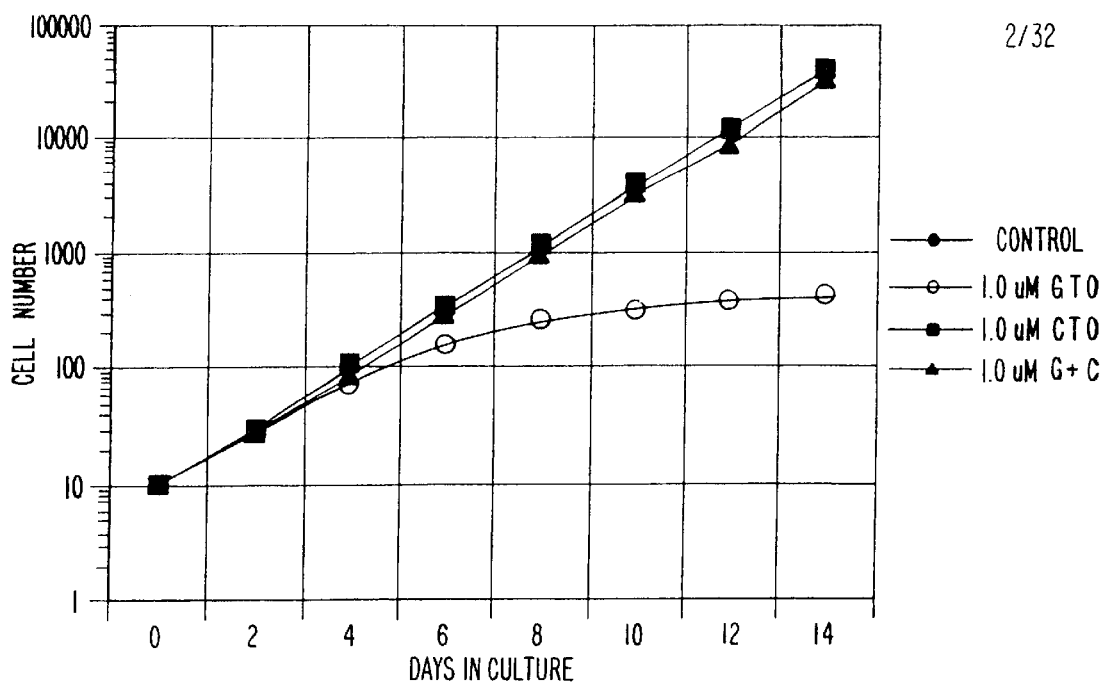

Specifically, MDA 157 human breast cancer cells with an immortal phenotype were seeded at 10,000 cells per well in 12 well tissue culture dishes and fed medium only or medium supplemented with GTO-12 (at 1.0 $\mu$M, 0.1 $\mu$M, and 0.01 $\mu$M). As shown in FIG. 2, cells grown in medium without oligonucleotide, or with doses of less than 1.0 $\mu$M continued replicating in an immortal phenotype. Cells fed the GTO-12 oligonucleotide, at 1.0 $\mu$M, however, ceased to proliferate after less than 10 doubling. Cells grown in the presence of 1.0 $\mu$M CTO-12 or 1.0 $\mu$M CTO-12 and 1.0 $\mu$M GTO-12 (G+C) continued to express the immortal phenotype suggesting that the GTO-12 oligonucleotide was not intrinsically toxic (FIG. 3). The lack of effect of the G+C mixture may reflect the CTO-12 oligonucleotide, competing with or base pairing with the GTO-12 oligonucleotide, this preventing its inhibitory effect on the cancer cell telomerase.

Example 3
Telomere Length as a Biomarker

In the U.S. and Western Europe, atherosclerosis is the principal contributor to mortality from cardiovascular diseases (Ross, 314 *N. Engl. J. Med.* 488, 1986). Atherosclerosis is characterized by the mural and focal formation of lipid and cell-rich lesions or "plaques" on the intimal surfaces of arterial tissues. This is followed by an age-dependent expansion of the lesion into the lumen, potentially leading to occlusion and to myocardial and/or cerebral infarction (Haust, (1981) in Vascular Injury and Atherosclerosis, ed. Moore, S. (Marcel Dekker Inc., New York), pp. 1–22; Ross and Glomset, 295(7) *N. Engl. J. Med.* 369, 1976; and Ross, 295(8) *N. Engl. J. Med.* 420, 1976). Prominent among the mechanisms proposed to explain the pathogenesis of atherosclerosis is the "response-to-injury" hypothesis (Ross, 314 *N. Engl. J. Med.* 488, 1986; Moore, (1981) in Vascular Injury and Atherosclerosis, ed. Moore, S. (Marcel Dekker Inc., New York), pp. 131–148; and Moore, 29(5) *Lab. Invest.* 478, 1971) in which repeated mechanical, hemodynamic and/or immunological injury to the endothelium is the initiating event.

A prediction of this hypothesis is that the intimal and medial tissue in the area comprising the atherosclerotic plaque will have a higher rate of cell turnover than the surrounding normal tissue. Several lines of evidence support this prediction. Ross et al., (Ross and Glomset, 295(7) *N. Engl. J. Med.* 369, 1976; Ross, 295(8) *N. Engl. J. Med.* 420, 1976) showed that cultured smooth muscle cells from fibrous plaques displayed lower responsiveness to growth serum when compared to cells from the underlying medial layer. Moss and Benditt 78(2) (1973) *Am. J. Pathol.* 175, 1973, showed that the replicative life-span of cell cultures from arterial plaques were equal to or less than the replicative life-spans from cells of nonplaque areas. Dartsch et al., 10 *Arteriosclerosis* 62, 1992, showed that human smooth muscle cells obtained from primary stenosing lesions became senescent in culture far later than smooth muscle cells from restenosing lesions. These results suggest that cells derived from regions of atherosclerotic plaques undergo more cellular divisions than cells from non-plaque areas hence rendering them older and nearer to their maximum replicative capacity.

Thus, to understand the pathogenesis of atherosclerosis, one must examine the alterations in the behavior of cell turnover on and adjacent to the arterial lesions. One requires a biomarker for the cell turnover of intimal and medial tissue. Several workers have examined biomarkers for the progression of atherosclerosis or for the propensity of an individual to develop atherosclerosis. The former objective entailed the measurement of a number of biochemical compounds which are detected in the plasma but originate from the endothelium. Examples are serum Type III collagen (Bonnet et al., 18 *Eur. J. Clin. Invest.* 18, 1988), von Willebrand's Factor (Factor VIII)(Baron et al., 10 *Arteriosclerosis* 1074, 1990), cholesterol, triglycerides, apolipoprotein B (Stringer and Kakkar, 4 (1990) *Eur. J. Vasc. Sure.* 513, 1990), lipoprotein (a) (Breckenridge, 143 *Can. Med. Assoc. J.* 115, 1990; Mezdour et al., 48 *Ann. Biol. Clin. (Paris)* 139, 1990; and Scanu, 14 *Clin. Cardiol.* 135, 1991), endothelin (Lerman et al., 325 *N. Engl. J. Med.* 997, 1991) and heparin-releasable Platelet Factor 4 (Sadayasu et al., 14 (1991) *Clin. Cardiol.* 725, 1991). A number of markers originate from the cell surface (Hanson et al., 11 (1991) *Arterioscler. Thromb.* 745, 1991; and Cybulsky and Girnbrone, 251 *Science* 788, 1991). Other markers monitor physiological aberrations as a result of atherogenesis (Vita et al., 81 (1990) *Circulation* 491, 1990). Candidate genes used to delineate the RFLP profile of those susceptible to atherogenesis (Sepehrnia et al., 38 (1988) *Hum. Hered.* 136, 1988; and Chamberlain and Galton, 46 *Br. Med. Bull.* 917, 1990) have also been established. However, there have been relatively few markers developed to monitor directly cell turnover.

Applicant now shows that telomere length may serve as a biomarker of cell turnover in tissues involved in atherogenesis. The results show that endothelial cells lose telomeres in vitro as a function of replicative age and that in vivo telomere loss is generally greater for tissues of the atherosclerotic plaques compared to control tissue from non-plaque regions.

In general, telomere lengths were assessed by Southern analysis of terminal restriction fragments (TRF, generated through HinfI/RsaI digestion of human genomic DNA. TRFs were resolved by gel electrophoresis and hybridized with a telomeric oligonucleotide ($^{32}$P-(CCCTAA)$_3$) (Seq. ID No. 4). Mean TRF length decreased as a function of population doubling in human endothelial cell cultures from umbilical veins (m=−190 bp/PD, P=0.01), and as a function of donor age in iliac arteries (m=−120 bp/PD, P=0.05) and iliac veins (m=−160 bp/PD, P=0.05). Thus, mean TRF length decreased with the in vitro age of all cell cultures. When early passage cell cultures were assessed for mean TRF length as a function of donor age, there was a significant decrease for iliac arteries (m=−102 bp/y, P=0.01) but not for iliac vein (m=47 bp/y, P=0.14). Mean TRF length of medial tissue decreased significantly (P=0.05) as a function of donor age. Intimal tissues from one individual who displayed extensive development of atherosclerotic plaques possessed mean TRF lengths close to those observed for senescent cells in vitro (~6 kbp). These observations indicate that telomere size indeed serves as a biomarker for the replicative history of intima and media and that replicative senescence of endothelial cells is involved in atherogenesis.

Specifically, the following materials and methods were used to achieve the results noted below.

Endothelial Cell Cultures

Human umbilical vein endothelial cells (HUWVEC) were obtained from Dr. Thomas Maciag of the Jerome H. Holland Laboratory of the American Red Cross. Human endothelial cells from the iliac arteries and iliac veins were obtained from the Cell Repository of the National Institute of Aging (Camden, N.J.). Cells were grown at 37° C. in 5% $CO_2$ on 100 mm tissue plates whose interiors were treated with an overnight coating of 0.4% gelatin (37° C.). The supplemented media consisted of M199, 15% fetal bovine serum, 5 U/ml heparin and 20 µg/ml crude Endothelial Cell Growth Supplement (Collaborative Research) or crude Endothelial Cell Growth Factor (Boehringer-Mannheim). Cultures were trypsinized (0.05%, 3 minutes) at confluence, reseeded at 25% of the final cell density and refed every 2–3 days.

Tissue Samples

Tissue samples from the aortic arch, abdominal aorta, iliac artery and iliac vein were obtained from autopsies at the Department of Pathology, Health Sciences Center, McMaster University. Post-mortem times ranged from 5 to 8 hours. The intima was obtained by cutting open the arteries or veins and carefully scraping off the lumenal surface with a No. 10 scalpel (Lance Blades, Sheffield) (Ryan, 56 Envir. Health Per. 103, 1984). The resulting material was either treated directly for extraction of DNA or processed for cell culture.

The adventitial layer was removed by cutting or scraping the non-lumenal side of the vessel. The remaining medial layer was prepared for DNA extraction by freezing it in liquid-$N_2$ and grinding it in a liquid-$N_2$ chilled mortar and pestle (Kennedy et al., 158 Exp. Cell Res. 445, 1985). After the tissue was ground to a powder, 5 ml of frozen digestion Buffer (10 mM Tris; 100 mM NaCl; 25 mM EDTA; 0.5% SDS; pH 8.0) was added and ground into the powderized tissue. The powder was then transferred to a 50 ml Falcon tube and incubated at 48° C. until thawed. Proteinase K (10 mg/ml) was added to a final concentration of 0.2 mg/ml. After a 12–16 hour incubation, the solution was removed from the water bath and either prepared for DNA extraction or stored at 20° C.

Extraction and Restriction Enzyme Digestion of Genomic DNA

DNA was extracted as described previously (Harley et al., 345 Nature 458, 1990; Allsopp et al., 89 Proc. Natl. Acad. Sci. USA 10114, 1992). In brief, proteinase K-digested lysates were extracted twice with one volume of phenol:chloroform:isoamyl alcohol (25:24:1) and once with chloroform. Nucleic acid was precipitated by adding 2 volumes of 100% EtOH to the aqueous layer, washed once with 70% EtOH and finally resuspended in 100–200 µl of 10 mM Tris-HCl, 1 mM EDTA, pH 7.5. DNA was quantified by fluorometry and 1 µg was digested with 1 unit each of HinfI/RsaI for 3–24 hours at 37° C. Complete digestion was monitored by gel electrophoresis. The integrity of the DNA before and after digestion was monitored in control experiments by gel electrophoresis.

Southern Blot Hybridization

Electrophoresis of digested genomic DNA was performed in 0.5% agarose gels in a standard Tris, sodium borate, EDTA buffer for a total of 650–700 V/hr as described previously (Harley et al., 345 Nature 458, 1990; Allsopp et al., 89 Proc. Natl. Acad. Sci. USA 10114, 1992). After electrophoresis, the gel was placed onto 3 mm Whatman filter paper and dried under vacuum for 25 minutes at 60° C. Gels were denatured by soaking in 0.5 M NaOH, 1.5 M NaCl for 10 minutes at room temperature and then neutralized through immersion in 0.5 M Tris, 1.5 M NaCl. Genomic DNA was immersed in standard hybridization solution (Harley et al., 345 Nature 458, 1990) (6×SSC) with the telomeric $^2$P-(CCCTAA)$_3$ probe (Seq. ID No. 4) for 12–16 hours at 37° C. The telomeric smears were visualized through autoradiography on pre-flashed ($OD_{545}$=0.15) Kodak XAR-5 film. The mean lengths of the terminal restriction fragments (TRFs) were calculated from densitometric scans of the developed films as described previously (Harley et al., 345 Nature 458, 1990).

In vitro Results

Figure 4:
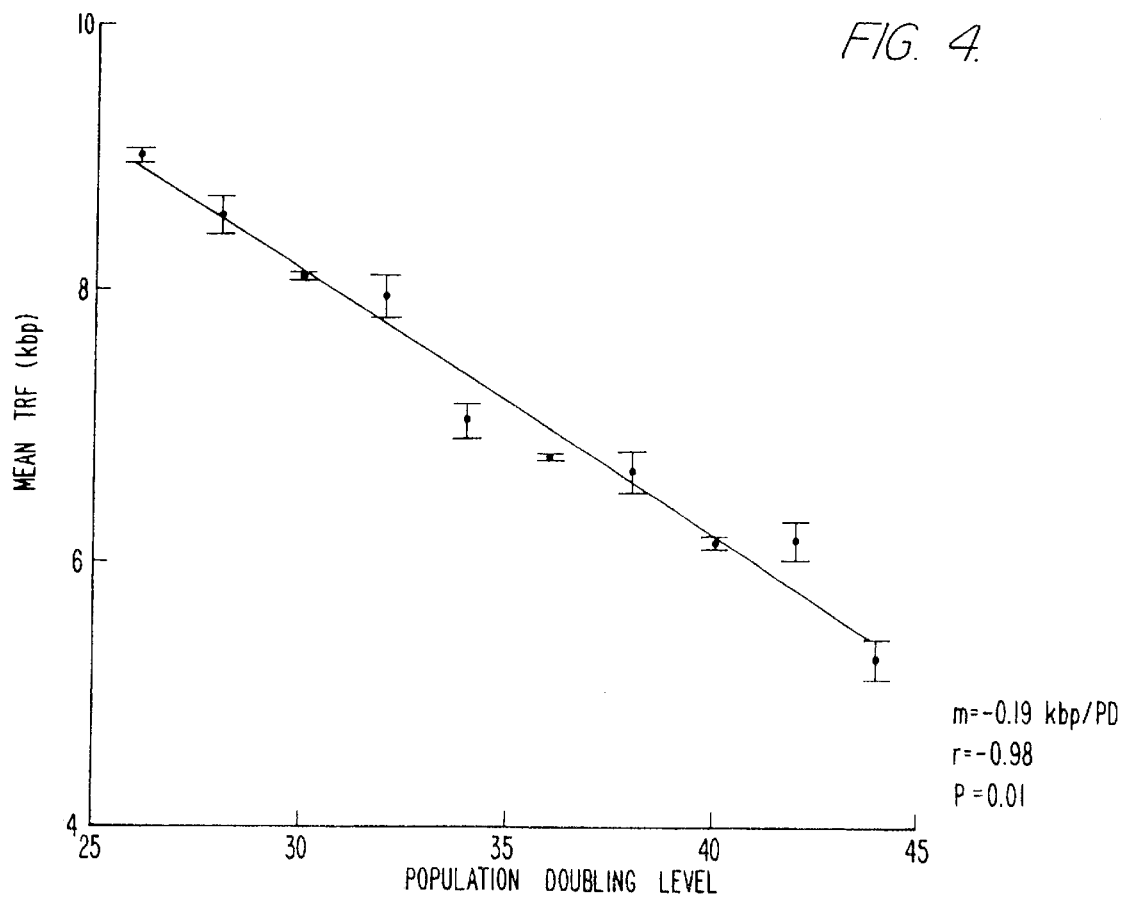
FIG. 4 is a linear plot of mean terminal restriction fragment (TRF) length versus PDL for human umbilical vein endothelial cell cultures. The plot had a slope (m) of $-190 \pm 10$ bp/PD, $r=-0.98$, $P=0.01$.

To determine the feasibility of employing telomere length as a biomarker for cell turnover in atherosclerosis, we first examined the change in telomere length in cultured endothelial cells where cell division can be directly monitored in vitro. The DNA was digested with HinfI and RsaI, and the resulting terminal restriction fragments (TRF) were subjected to Southern analysis. As in human skin fibroblasts (Allsopp et al., 89 Proc. Natl. Acad. Sci. USA 10114, 1992), mean TRF length decreased as a function of population doubling (PD). Thus, telomere length decreases with in vitro age of human umbilical vein endothelial cells. Mean TRF length decreased linearly (P=0.01) at a rate of 190±10 bp/PD (see FIG. 4). The Y-intercept, which signifies the mean TRF at 0 PDL is 14.0 kbp while mean TRF at senescence was 5.7±0.4 kbp.

To prove that telomere length decrease occurred in endothelial cells from other arterial and venous sources, mean TRF length versus population doubling level (PDL) was determined for several strains of endothelial cells from human iliac artery and human iliac vein. In both iliac arteries and iliac veins there was a significant (P=0.05) linear decrease in mean TRF length with age of culture: 120±60 bp per population doubling for the iliac artery and 160±30 bp per population doubling for the iliac veins from endothelial cells.

In vivo Results

Figure 5:
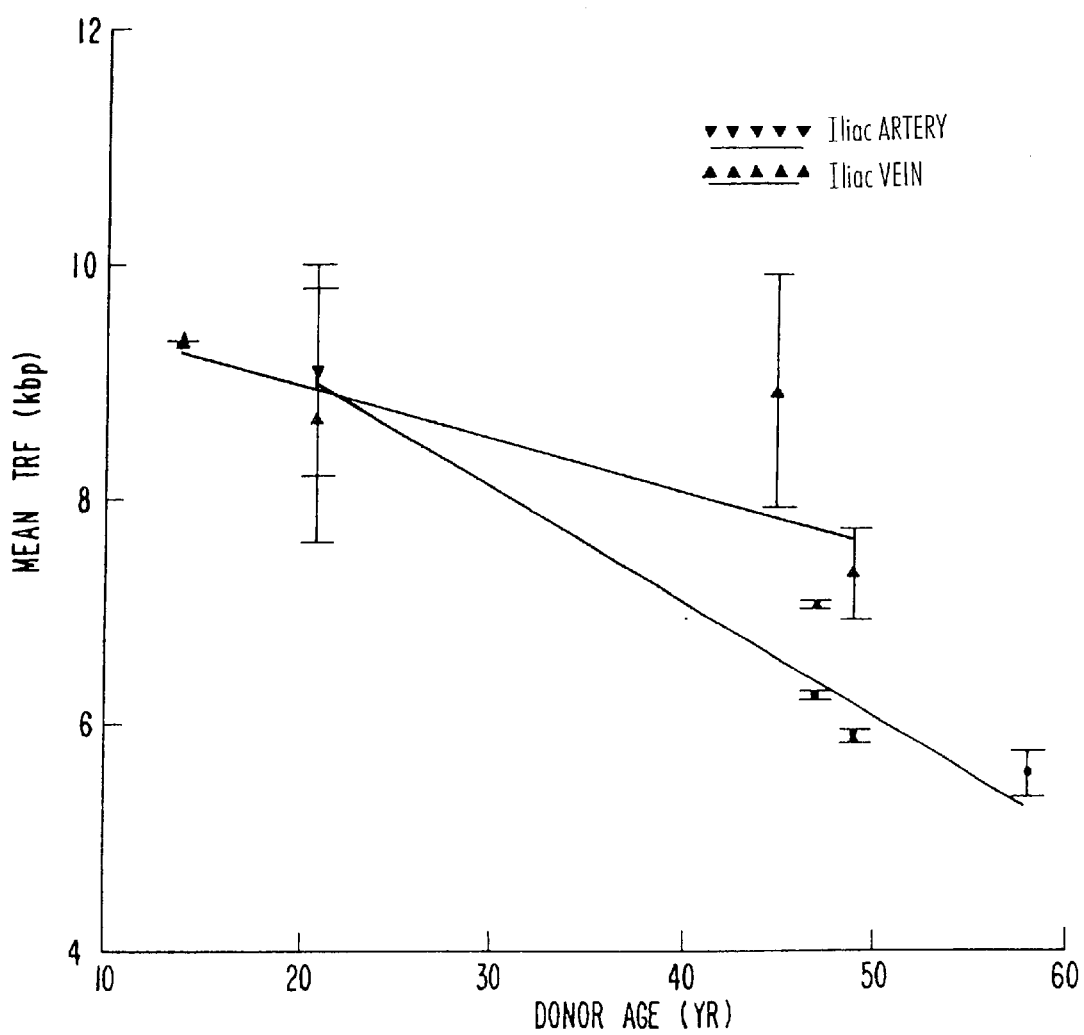
FIG. 5 is a plot of mean TRF of endothelial cell cultures from human iliac arteries and iliac veins as a function of donor age. Parameters for iliac arteries are: m=−102 bp/yr, r=−0.98, P=0.01 and for iliac veins are: m=−42 bp/yr, r=−0.71, P=0.14.

Formation of atherosclerotic plaques occurs more often in the iliac artery than in the iliac vein (Crawford, (1982) Pathology of Atherosclerosis (Butterworth and Co. Ltd., U.K.), p. 187–199), thus it is expected that turnover of intimal tissue in vivo from the iliac artery should be greater than that from the iliac veins. To test this, nine different strains of endothelial cell cultures from iliac arteries and veins of donors ranging in age from 14–58 years of age were cultivated and TRF lengths from the earliest possible PDL were determined (FIG. 5).

Consistent with the hypothesis of greater cell turnover in vivo in arteries than in veins, the rate of decrease in mean TRF length, was significant over the age range 20–60 years for iliac arteries (−100 bp/yr, P=0.01) and greater than for the iliac veins (−47 bp/yr, P=0.14). Among the nine strains of endothelial cells, there were cultures from the iliac artery and iliac vein from the same individuals for 3 of the donors, aged 21, 47 and 49 years. There was a significantly shorter mean TRF length in the cultures of iliac artery cells as compared to the venous cells for the two older donors. The younger donor showed no significant difference in mean TRF length between the two cultures, possibly reflecting relatively little difference in cell turnover between the vessels of the 21-year old donor.

Differences in mean TRF length of the cell cultures from iliac arteries and iliac veins in donors of different ages will reflect not only differences in original mean TRF length of the primary tissues but also differences in the rate of telomere loss between the different cultures in vitro during the time required to collect sufficient cells for analysis (approximately 5–10 PDL). To determine if there is a relationship between cell turnover and the extent of atherosclerotic plaque formation, we examined mean TRF length in primary tissue. Autopsies from 3, 11, 12, 14, 18, 26, 75-year old females and a 77-year old male were performed. Sections of the aortic arch, abdominal aorta, iliac artery and iliac vein were taken and the intimal and medial tissues separated and assessed for TRF length.

Sufficient intimal tissue could be obtained from the aortic arch, abdominal aorta, iliac arteries and iliac veins of 3 donors (aged 27, 75 and 77 years) for TRF analysis. There was a striking difference between the mean TRF lengths averaged over these sites in the 27-year old female (10.4±0.7 kbp) versus the 75-year old (8.8+0.6 kbp) and the 77-year old male (6.3+0.4 kbp). It is noteworthy that the 77-year old male had extensive atherosclerotic lesions in his vasculature and that the mean TRF length of his intimal tissue is close to that of endothelial cells, at senescence in vitro (approximately 6 kbp, FIG. 4).

Figure 6:
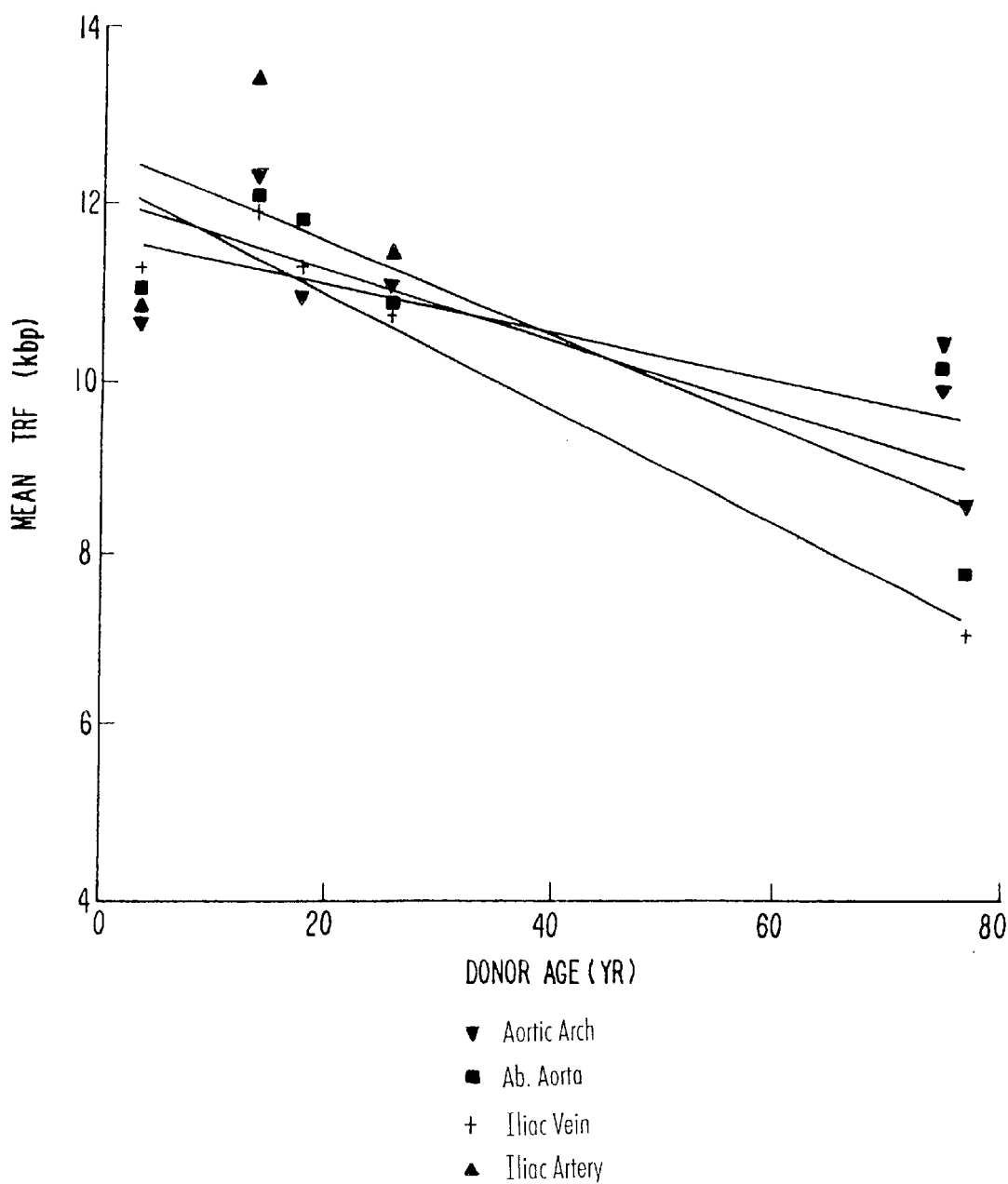
FIG. 6 is a plot of decrease in mean TRF of medial tissue from the aortic arch, abdominal aorta, iliac artery and iliac vein as a function of donor age. Parameters for linear plot are: m=−47 bp/yr, r=−0.85, P=0.05.

FIG. 6 shows that mean TRF of medial tissue (from the aortic arch) decreases with donor age at a small but significant rate (47 bp/yr, P=0.05). Thus, medial cells turnover in vivo occurs at a rate less than that of the venous or arterial endothelial cells.

In general, telomere loss in medial tissue underlying an atherosclerotic plaque was greater than those in non-plaque regions (Table 1). With the 75-year old female, mean TRF was significantly reduced in medial DNA from the plaque regions versus the non-plaque regions of both the aortic arch (P=0.04) and the abdominal aorta (P=0.01). For the 77-year old male, this was observed in the abdominal aorta (P=0.01).

TABLE 1

Mean TRF values for primary medial tissues of plaque and non-plaque areas

|  | Plaque Region | Non-Plaque Region | P |
|---|---|---|---|
| 75-year old Donor |  |  |  |
| Aortic Arch | 10.2 ± 0.5 | 11.1 ± 0.1 | 0.04 |
| Abdominal Aorta | 9.5 ± 0.6 | 11.0 ± 0.1 | 0.01 |

TABLE 1-continued

Mean TRF values for primary medial tissues of plaque and non-plaque areas

|  | Plaque Region | Non-Plaque Region | P |
|---|---|---|---|
| 77-year old Donor |  |  |  |
| Aortic Arch | 8.2 ± 0.4 | 8.4 ± 0.2 | NS |
| Abdominal Aorta | 7.1 ± 0.1 | 8.2 ± 0.4 | 0.01 |

These results show that mean TRF length decreases as a function of donor age for primary medial and intimal tissue, suggesting that cell turnover does occur in cardiovascular tissue. The decrease in mean TRF length for plaque regions versus clear regions of medial tissue from the same blood vessel is consistent with augmented cell turnover of tissue associated with atherosclerotic plaques. Thus, the results indicate that measurement of telomere length provides a biomarker for alterations of cellular turnover in tissues associated with cardiovascular diseases, i.e., cells of the intima and media.

Measurement of telomere length is a direct register of proliferative history but to obtain telomeric DNA one must obtain a biopsy of endothelial tissue. Since removal of the endothelium in itself can induce plaque formation, the biopsy strategy obviously entails ethical and practical problems. Based upon experience with autopsy samples one requires a minimal area of 1 cm² in order to perform a Southern analysis as described in this paper. For a practical biopsy, this is untenable. A detection technique to circumvent this problem may be confocal fluorescent microscopy.

Example 4
Simplified Test for Telomere Length

Telomere length has been found to be the best predictor of the remaining lifespan of cells cultured from donors of different ages. The ability to measure telomere length thus has significant clinical use. Because of their simple repetitive nature, telomeres lack DNA sequences recognized by many restriction enzymes. One way to measure telomere length is to digest DNA with restriction enzymes with 4-base recognition sites, which cuts most of the DNA into very small pieces and leaves the telomeres in relative large TRFs (Terminal Restriction Fragments). A Southern blot of the DNA is then probed with a radioactive TTAGGGT-TAGGGTTAGGG (Seq. ID No. 5) oligonucleotide, and the size of the TRF determined.

A much simpler method to measure telomere length exploits the fact that the telomere sequence lacks guanidine residues in the C-rich strand. Genomic DNA can be melted and mixed with the DNA synthesis primer CCCTAAC-CCTAACCCTAACCCTAA (Seq. ID No. 6) in the presence of DNA polymerase and only three deoxynucleotides (DATP, dTTP and radioactive dCTP). Rare complementary sequences scattered throughout the genome would fail to extend due to the lack of dGTP. The length of the extended DNA can then be determined from a simple gel electrophoresis. The amount of DNA synthesized (counts incorporated per μg of DNA) will be directly proportional to telomere length, and for diagnostic purposes a simple measure of radioactivity would then suffice to quantitate telomere length.

Example 5
Identification of DNA Sequences Near Telomeres

There are good reasons to believe that the regulatory factors that control cellular and organismal senescence are located near telomeres, and are themselves regulated by the length of the adjacent telomere. It is thus important to identify and clone them in order to be able to understand and manipulate the aging process. In addition, there is great interest in identifying unique telomeric DNA within the human genome project, since telomeric markers for mapping purposes are lacking for the ends of the chromosomes.

In one method, large telomeric DNA is purified as follows. A biotinylated CCCTAACCCTAA (Seq. ID No. 7) oligonucleotide is used to prime DNA synthesis in double-stranded genomic DNA. The only sequences with which this oligonucleotide can anneal will be the single-stranded base overhangs at telomere ends. The extended DNA will then be digested with a restriction enzyme such as NotI to produce large restriction fragments. Biotinylated fragments are retrieved using streptavidin coated magnetic beads, and analyzed by pulsed field electrophoresis. 46 fragments (one for each end of the 23 human chromosomes) are produced.

Multiple strategies can be used to pursue the successful isolation of large telomeric DNA. The DNA can be labeled and used to screen cDNA libraries in order to identify genes located near telomeres. The expression of these cDNAs can then be examined in young versus old cells in order to identify those which are differentially expressed as a function of cellular senescence, and which are thus candidates to be regulatory factors that control aging.

The purified telomeric DNA can also be digested with additional restriction enzymes, mixed with 100-fold excess of genomic DNA, melted and reannealed. Under these circumstances, the repetitive sequences in the telomeric DNA will anneal with genomic DNA while unique sequences in the purified DNA will self-anneal. Only the self-annealed unique sequences will contain restriction overhangs at each end, and thus a simple cloning of the annealed DNA will result in the successful cloning of only unique fragments.

Example 6
Telomere Loss in Down's Syndrome Patients

Loss of telomeric DNA from human chromosomes may ultimately cause cell cycle exit during replicative senescence. Since lymphocytes have a limited replicative capacity and blood cells were previously shown to lose telomeric DNA during aging in vivo, we wished to determine whether accelerated telomere loss is associated with the premature immunosenescence of lymphocytes in individuals with Down's Syndrome (DS), and whether telomeric DNA is also lost during aging of lymphocytes in vitro.

To investigate the effects of aging and trisomy 21 on telomere loss in vivo, genomic DNA was isolated from peripheral blood lymphocytes of 140 individuals (0–107 y) and 21 DS patients (0–45 y). Digestion with restriction enzymes HinfI and RsaI generated terminal restriction fragments (TRFs) which can be detected by Southern analysis using a telomere-specific probe, ($^{32}$P-(CCCTAA)$_3$). The rate of telomere loss was calculated from the decrease in mean TRF length as a function of donor age. DS patients showed a significantly higher rate of telomere loss with donor age (133±15 bp/y) compared to age-matched controls (41±7.7 bp/y) (P<0.0005), indicating that accelerated telomere loss is a biomarker of premature immunosenescence of DS patients, and may play a role in this process.

Telomere loss during aging in vitro was calculated for lymphocytes from two normal individuals grown in culture for 20–30 population doubling. The rate of telomere loss was 90 bp/cell doubling, that is, it was comparable to that seen in other somatic cells. Telomere lengths of lymphocytes from centenarians and from older DS patients were similar to those of senescent lymphocytes in culture, which suggests that replicative senescence could partially account for aging of the immune system in DS patients and elderly individuals.

The following materials and methods were used to obtain the results provided below.

Culture of Human Peripheral Blood T Lymphocytes

Adult peripheral blood samples were collected, and mononuclear cells were isolated by Ficoll-Hypaque gradient centrifugation then cryopreserved in liquid nitrogen. Cultures were initiated by mixing $10^{-6}$ mononuclear cells with $10^6$ irradiated (8000 Rad) lymphoblastoid cells (Epstein-Barr virus transformed B cells), or $10^6$ mononuclear cells with 10 µg/ml phytohemagglutinin (PHA-P, Difco) in each well of a 48-well cluster plate (Costar). After 8 to 11 days, cells were washed and plated in 2 ml wells of 24-well cluster plates at a concentration of $2-4 \times 10^5$/ml. Cultures were passaged every three to four days, or whenever viable cell concentration (determined by trypan blue exclusion) reached $\geq 8 \times 10^5$/ml. Cultures were terminated when they showed no proliferative response to irradiated lymphoblastoid cells and/or when there were no viable cells present in the entire visual field of the haemocytometer. Once transferred to the 2 ml wells, cells were continuously exposed to 25 U/ml of recombinant interleukin-2 (Amgen). The media used were (a) RPM1 (Irvine Scientific) supplemented with 10 to 20% fetal calf serum, 2 mM glutamine, and 1 mM Hepes; (b) AIM V™, a DMEM/nutrient mixture F-12 basal medium, containing purified human albumin, transferrin, and recombinant insulin (Gibco), supplemented with 25% Ex-cyte (an aqueous mixture of lipoprotein, cholesterol, phospholipids, and fatty acids, (Miles Diagnostics).

At each cell passage, the number of population doubling (PD) was calculated according to the formula:

$$PD = \ln(\text{final viable cell no. initial cell no.})/\ln 2.$$

Isolation of DNA

PBLs (including=15% monocytes) were isolated using Ficoll-Hypaque gradient centrifugation (Boyum et al., 21(97) Scan. J. Clin. Lab. Invest. 77, 1968) and washed 3 times in PBS. Cell pellets were resuspended in 500 µl of proteinase K digestion buffer (100 mM NaCl, 10 mM Tris pH 8, 5 mM EDTA, 0.5% SDS) containing 0.1 mg/ml proteinase K and incubated at 48° C. overnight. Lysates were extracted twice with phenol/chloroformisoamyl alcohol (25:24:1 v/v/v) and once with chloroform. DNA was precipitated with 95% ethanol and dissolved in TE (10 mM Tris, 1 mM EDTA, pH=8).

Analysis of Telomeric DNA

Genomic DNA (10 µg) was digested with HinfI and RsaI (BRL) (20 U each), re-extracted as above, precipitated with 95% ethanol, washed with 70% ethanol, dissolved in 50 µl TE, and quantified by fluorometry. One gg of digested DNA was resolved by electrophoresis in 0.5% (w/v) agarose gels poured on Gel Bound (FMC Bioproducts) for 700 V-h. Gels were dried at 60° C. for 30 minutes, denatured, neutralized, and probed with 5' end-labeled $^{32}$P-(CCCTAA) as described above. Autoradiograms exposed within the linear range of signal response were scanned with a Hoefer densitometer. The signal was digitized and subdivided into 1 kbp intervals from 2 kbp to 21 kbp for calculation of the mean TRF length (L) using the formula L=Σ, (OD$_i$L$_i$)/ΣOD$_i$, where OD$_i$= integrated signal in interval i, and L=TRF length at the mid-point of interval i.

TRF Length vs. Age

When measured as a function of donor age, mean TRF length in PBS of 140 unrelated normal individuals (aged 0–107 y) declined at a rate of 41±2.6 bp/y (p<0.00005, r-0.83). This rate of TRF loss for PBLs is close to that previously found for peripheral blood cells by Hastie et al., 346 Nature 866, 1990. When our data were separated according to gender it was noticed that males lost telomeric DNA at a rate slightly faster than that of females (50±4.2 vs 40±3.6 bp/y), but this difference did not reach statistical significance (p=0.1). The 18 centenarians (aged 99–107 y) among our population of normal individuals had a mean TRF length of 5.28±0.4 kbp (FIG. 7). Interestingly, the standard deviation of mean TRF values for the centenarians (0.4 kbp) was much smaller than that of other age groups. Although it is possible that this represents selection of a more homogeneous population of cells with age, it is also possible that the group of centenarians were less genetically diverse than the younger populations in our study.

Mean TRF length was also analyzed in PBLs of 21 Down's Syndrome individuals (aged 2–45 y) and the rate of loss was compared to 68 age-matched controls (aged 0–43 y). We found that cells from DS patients showed a significantly greater rate of telomere loss (133±15 bp/y vs 41±7.7 bp/y; one tailed t-test, t=5.71, p<0.0005) (FIG. 8).

To determine the rate of telomere loss as a function of cell doubling, we cultured normal lymphocytes from 2 individuals in vitro until replicative senescence and measured mean TRF length at several population doubling levels (FIG. 9). Mean TRF length decreased 90 bp/population doubling in these strains, within the range observed for other human somatic cell types. The mean TRF length at senescence for the lymphocyte cell strains shown here and one other analyzed at terminal passage (FIG. 9), was 5.1±0.35 kbp. The observed TRF values in vivo for PBLs of centenarians (5.3±0.4 kbp) and old DS patients (4.89±0.59 kbp), were close to this value, suggesting that a fraction of the cells from these individuals were close to the limit of their replicative capacity.

The results showing that telomeres in PBLs from normal individuals shorten during aging in vivo and in vitro extend similar observations on human fibroblasts (Harley et al., 345 Nature 458, 1990) and support the hypothesis that telomere loss is involved in replicative senescence. We also found that in Down's Syndrome, the rate of telomere loss in PBS in vivo was significantly higher than that in age-matched normal donors. Thus, accelerated telomere loss in PBS of trisomy 21, a syndrome characterized by premature immunosenescence and other features of accelerated aging (Martin, "Genetic Syndromes in Man with Potential Relevance to the Pathobiology of Aging", in: Genetic Effects on Aging, Bergsma, D. and Harrison D. E. (eds.), pp. 5–39, Birth Defects: Original article series, no. 14, New York: Alan R. Liss (1978)), could reflect early senescence of lymphocytes.

The increased rate of telomere loss in PBS from DS patients could reflect a higher turnover rate of cells in vivo due to reduced viability of the trisomy 21 cells. However, it is also possible that the rate of telomere loss in PBS from DS patients is greater per cell doubling than that in normal individuals.

The pathology of DS is similar in many ways to normal aging. Premature senescence of the immune system possibly plays a role in this similarity since DS patients have a high incidence of cancer and suffer from autoimmunity. In support of this idea, lymphocytes of older DS patients and old individuals share several characteristics, including diminished response of T-cells to activate and proliferate in response to antigen, low replicative capacity, and reduced B- and T-cell counts (Franceschi et al., 621 Ann. NY Acad. Sci. 428, 1991). Our finding that telomere length decreased faster in DS patients than normal individuals, and that the mean TRF length in centenarians and old DS patients in vivo were similar to that of senescent lymphocytes in vitro (≈5 kbp)1 extends these observations. Moreover, these data suggest that replicative senescence within the lymphoid lineage in vivo contributes to the compromised immune system of both elderly individuals and Down's Syndrome patients.

Example 7
Ovarian Cancer and Telomerase Activity

The following is an example of a method by which telomerase activity is shown to correlate with the presence of cancer cells. In addition, the length of TRF was determined as an indication of the presence of tumor cells. Generally, it was found that tumor cells had significantly lower TRF values than surrounding normal cells, and had telomerase activity. Thus, these two features are markers for the presence of tumor cells.

The following methods were used to obtain these results:
Separation of Tumor and Non-tumor Cells In one method, ascitic fluid was obtained by either diagnostic laparotomy or therapeutic paracentesis (from patients diagnosed as having ovarian carcinoma), and centrifuged at 600×g for 10 minutes at 4° C. The cell pellet was washed twice in 10 to 30 ml of phosphate buffered saline (PBS: 2.7 mM KCl, 1.5 mM $KH_2PO_4$, 137 mM NaCl and 8 mM $Na_2HPO_4$) and centrifuged at 570×g for 4 minutes at 4° C. After the final wash the cell pellet was resuspended in 20 ml of PBS and filtered through a 30 or 10 Am nylon mesh filter (Spectrum) which retains the tumor clumps but not single cells. The filters were backwashed to liberate highly purified tumor clumps. The flow-through was a combination of fibroblasts, lymphocytes and tumor cells.

In another method ascitic fluid cells were collected and washed as described above. The cellular pellet was resuspended in a-MEM with 10% fetal calf serum and cultured in 150 mm dishes. After 12 hours the media was removed and new plates were used to separate the adhering fibroblasts from the non-adhering cells in the medium. After 12 hours the media containing mostly tumor clumps was removed from the second plates and allowed to adhere in DMA F12 medium supplemented with 3% fetal calf serum, 5 ng/ml EGF, 5 µg/ml insulin, 10 gg/ml human transferrin, $5×10^{-5}$ M phosphoethanolamine and $5×10^{-5}$ M ethanolamine. These tumor cells were cultured for DNA analysis and S100 extracts.

DNA Extraction

Cells were lysed and proteins were digested in 10 mM Tris-HCl (pH 8.0), 100 mM NaCl, 25 mM EDTA, 0.5% SDS, 0.1 mg/ml proteinase K at 48° C. overnight. Following 2 extractions with phenol and 1 with chloroform, DNA was precipitated with ethanol and dissolved in 10 mM Tris-HCl (pH 8.0), 1 mM EDTA (TE).

Determination of TRF Length and Amount of Telomeric DNA

Genomic DNA was digested with HinfI and RsaI, extracted and precipitated as above, and redissolved in TE. DNA concentration was measured by fluorometry (Morgan et al., 7 Nucleic Acids Res. 547, 1979). DNA samples (1 µg each) were loaded onto a 0.5% agarose gel and electrophoresed for 13 hours at 90 V. The gel was dried at 60° C. for 30 minutes, denatured in 1.5 M NaCl and 0.5 M NaOH for 15 minutes, neutralized in 1.5 M NaCl, 0.5 M Tris-HCl (pH 8.0) for 10 minutes and hybridized to a 5' $^{32}P(CCCTAA)_3$ telomeric probe in 5×SSC (750 mM NaCl and 75 mM sodium citrate), 5× Denhart's solution (Maniatis et al., Molecular Cloning: A Laboratory Manual, Cold Spring Harbor Laboratory, Cold Spring Harbor (1982)) and 0.1× P wash (0.5 mM pyrophosphate, 10 mM Na$_2$HPO$_4$) at 37° C. for 12 hours. Following three high stringency washes in 0.24×SSC at 20–22° C. (7 minutes each), the gel was autoradiographed on pre-flashed (OD=0.15) Kodak XAR-5 X-ray films for 3 days with enhancing screens. Each lane was scanned with a densitometer and the data used to determine the amount of telomeric DNA and the mean TRF length as previously described (Harley et al., 345 *Nature* 458, 1990).

Preparations of S-100 Cell Extracts

A minimum of 6×10$^8$ cells were used for each extract. Ascitic fluid or purified ascitic fluid tumor cells (by the first method described above) were centrifuged at 570×g for 4 minutes at 4° C. Ascitic fluid tumor cells separated by the second method described above (grown in monolayer) were harvested by scraping with a rubber policeman, and centrifuged as above. The pellets were rinsed twice in cold PBS followed by centrifugation as above. The final pellet was rinsed in cold 2.3× Hypo buffer (1× Hypo buffer: 10 mM Hepes (pH 8.0)), 3 mM KCl, 1 mM MgCl$_2$, 1 mM DTT, 0.1 mM PMSF and 10 U/ml of RNAsin, 1 µM leupeptin and 10 µM pepstatin A, centrifuged for 5 minutes and resuspended in 0.75 volumes of 2.3× Hypo buffer. After incubation on ice for 10 minutes the sample was transferred to an ice cold 7 or 1 ml Dounce homogenizer and homogenized on ice using a B pestle (25–55 µm clearance). After a further 30 minutes on ice the samples having a volume larger than 1 ml were centrifuged for 10 minutes at 10,000 rpm (16,000×g) at 4° C. in a Beckman J3-13.1 swinging bucket rotor. One-fiftieth volume of 5 M NaCl was added, and the samples supernatant were centrifuged for 1 hour at 38,000 rpm (100,000×g) at 4° C. in a Beckman Ti50 rotor. Glycerol was added to a final concentration of 20% and the extract aliquoted and stored at −70° C. Samples less than 1 ml were centrifuged at 55,000 rpm for 1 hour at 4° C. in a TLA 100.2 rotor (Beckman) and NaCl and glycerol were added to the supernatant as above. Protein concentration in a typical extract was approximately 4 mg/ml.

Telomerase Assay

Telomerase activity was assayed by a modification of the method of Morin, 59 *Cell* 521, 1989. Aliquots (20 µl) of S-100 cell extract were diluted to a final volume of 40 Al containing 2 mM DATP, 2 mM dTTP, 1 mM MgCl$_2$, 1 µM (TTAGGG)$_3$ primer, 3.13 µM (50 µCi) a-$^{32}$P-dGTP (400 Ci/mmole), 1 mM spermidine, 5 mM β-mercaptoethanol, 50 mM potassium acetate, and 50 mM Tris-acetate (pH 8.5). In some experiments reaction volumes were doubled. The reactions were incubated for 60 minutes at 30° C. and stopped by addition of 50 µl of 20 mM EDTA and 10 mM Tris-HCl (pH 7.5) containing 0.1 mg/ml RNAseA, followed by incubation for 15 minutes at 37° C. To eliminate proteins, 50 µl of 0.3 mg/ml Proteinase K in 10 mM Tris-HCl (pH 7.5), 0.5% SDS was added for 10 minutes at 37° C. Following extraction with phenol and chloroform, unincorporated a-$^{32}$P-dGTP was separated by centrifuging the samples for 4 minutes at 500 g in a swinging bucket rotor through NICK SPIN columns (Pharmacia). DNA was precipitated by the addition of 5.3 µl of 4 M NaCl, 4 µg of carrier tRNA and 500 µl of ethanol at −20° C. DNA pellets were resuspended in 3 Al of formamide loading dye, boiled for 1 minute, chilled on ice and loaded onto an 8% polyacrylamide, 7 M urea sequencing gel and run at 1700 V for 2 hours using 0.6× TBE buffer. Dried gels were exposed to Kodak XAR-5 pre-flashed film at −70° C. with enhancing screen or to phosphoimager screens (Molecular Dynamics) for 7 days.

The results of the above experiments are shown in tables 2 and 3 below:

TABLE 2

Characteristics of ATCC Ovarian Carcinoma Cell Lines

| Cell line | Mean TRF Length (kbp) | Telomerase Activity |
|---|---|---|
| HEY | stable at 3.7 | + |
| CAOV-3 | stable at 3.7 | N.D. |
| SKOV-3 | Increases at 60 bp/pd | N.D. |

TABLE 3

Characteristics of Ovarian Carcinoma Tumor cells from Ascitic Fluid

| Patient | Description | Mean TRF Length (kbp) | Telomerase Activity |
|---|---|---|---|
| Pres-3 | Purified tumor cells | 3.7 | + |
| Mac-2 | Purified tumor cells | 3.7 | N.D. |
| Sib-1 | Purified tumor cells | 4.2 | N.D. |
| Ric 207 | Purified tumor cells | 3.3 | N.D. |
| Cra-1 | Purified tumor cells | 5.2 | N.D. |
| Ing-1 | Purified tumor cells | 5.8 | N.D. |
| Lep-1 | Purified tumor cells | 5.8 | N.D. |
| Lep-4 | Purified tumor cells | 5.6 | N.D. |
| Sol-1 | Purified tumor cells | 5.6 | N.D. |
| Rud-1 | Ascitic fluid cells | 3.4 | + |
| Murr-1 | Ascitic fluid cells | 3.8 | + |
| Dem-1 | Ascitic fluid cells | N.D. | + |
| Cas-1 | Ascitic fluid cells | 5.3 | + |
| Wad-1,2 | Ascitic fluid cells | 4.9 | N.D.* |

N.D. = not determined
*High background precluded detection

Table 4 shows the TRF length of cells from ascitic fluid. A minimum of 2 autoradiographs were scanned with a densitometer over the size range 2–21 kbp, and the densitometric values used to determine mean TRF length in kbp. Average standard deviation of the data was 0.5 kbp with the largest deviation being 2 kbp. The value following the three character patient code refers to the paracentesis number (i.e., OC1-1 is the first sample from patient OC1). Samples defined as E (early) were obtained near the time of presentation while samples L (late) were obtained near death. Paracenteses were performed 4 to 15 times over the course of 4 to 22 months.

TABLE 4

| Unfractionated | | Fractionated | | | Cultured cells | |
|---|---|---|---|---|---|---|
| Patient | TRF (kbp) | Patient | Normal TRF (kbp) | Tumour TRF (kbp) | Patient | Tumour* TRF (kbp) |
| OC1-1 | 3.8 | OC5-1 | 7.0 | 5.0 | OC18-2 | 3.4 |
| OC2-1 | 5.5 | OC6-1 | 9.2 | 5.4 | OC19-3 | 3.4 |

TABLE 4-continued

| Unfractionated | | Fractionated | | | Cultured cells | |
|---|---|---|---|---|---|---|
| Patient | TRF (kbp) | Patient | Normal TRF (kbp) | Tumour TRF (kbp) | Patient | Tumour* TRF (kbp) |
| OC3-1 | 5.4 | OC7-1 | 8.0 | 5.4 | OC20-1 | 4.2 |
| -2 | 4.4 | OC8-1 | 7.7 | 4.3 | OC21-1 | 3.3 |
| OC4-1 | 4.5 | OC9-1 | | 5.2 | OC5-1 | 4.3 |
| | | OC10-1 | | 3.9 | OC22-13 | 6.9 |
| | | OC11-2 | | 3.7 | | |
| | | OC12-1 | | 3.8 | | |
| | | OC13-1 | | 5.1 | | |
| | | Serial Samples | | | | |
| | | OC14-1 | (E) 9.4 | 5.0 | | |
| | | -4 | (L) 9.3 | 5.2 | | |
| | | OC15-1 | (E) 7.3 | 4.1 | | |
| | | -5 | (L) | 4.7 | | |
| | | OC16-1 | (E) | 3.9 | | |
| | | -2 | (E) | 3.4 | | |
| | | -7 | (L) | 3.9 | | |
| | | OC17-1 | (E) 7.7 | 4.3 | | |
| | | -15 | (L) | 4.7 | | |
| Means†: | 4.7 ± 0.7 | | 8.2 ± 0.9 | 4.5 ± 0.6 | | 3.7 ± 0.5 (4.2 ± 1.4)‡ |

*mean TRF length was determined for each of the samples over the course of at least 30 PD. Values were averaged since TRFs were stable in all populations
†average and standard deviation of the mean TRF lengths of all samples
‡mean value including OC22-13

Table 5 shows the telomerase activity in normal and tumor cells. Leukocytes and acsites cells were isolated and ascitic fluid cells fractionated into normal and tumor fractions and assayed for telomerase activity. Protein concntration in all extracts was <2 mg/ml, i.e., 20 fold higher than the lowest concentration at which activity was detected in control 293 CSH extract.

TABLE 5

| Unfractionated | | Fractionated | | |
|---|---|---|---|---|
| | Telomerase | | Telomerase activity | |
| Patient | activity | Patient | Normal | Tumour |
| OC4-1 | + | OC19-3 | N.D. | + |
| -5 | + | OC17-1 | — | N.D. |
| OC2-1 | ± | OC8-1 | — | N.D. |
| OC1-1 | + | LEK | — | N.D. |
| OC23-1 | + | | | |

In the TRF assay, each tumor clump had significantly lower TRF lengths than associated normal cells. (See FIG. 10).

In the telomerase assay, significantly greater telomerase activity was evident in the ascitic fluid of certain patients than in the control tumor lines HEY and PRES, or the control cell line 293 CSH (FIGS. 11, 33).

Example 8
Effect of HIV Infection on TRF Length

HIV infection leads to an acute viral infection manifesting itself as a virus-like syndrome, followed by a prolonged period of latency characterized by an absence of signs and symptoms. During this prolonged asymptomatic period (lasting usually 7–10 years), there is no diagnostic available for staging the course of the infection other than the presence or absence of antibodies to viral coat proteins. This does little to stage the disease or to help the physician measure the effectiveness of prophylactic agents.

While Meyaard et al., 257 Science 217, 1992, propose a programmed cell death for CD4$^+$ and CD8$^+$ cells of an HIV-infected individual, we propose that during those 7 to 10 years the immune system is able to keep the infection relatively repressed, but there is markedly increased turnover of the infected CD4$^+$ T-cells. This may be due in part to viral-mediated cell destruction. We propose that this essentially accelerates the replicative senescence of this particular subpopulation of T-cells, and with time results in a population of precursor pluripotent cells with markedly reduced proliferative capacity. Finally, this results in CD4$^+$ T-cells that are relatively unresponsive to stimuli to proliferate, as is typical of the replicative senescence of the cells observed in vitro.

We also propose that the replicative capacity of total peripheral lymphocytes or CD4$^+$ cells in particular, can be effectively determined by assaying telomere repeat length utilizing the method described above, e.g., with the oligonucleotide probe 5' TTAGGGTTAGGGTTAGGGTTAGGG (or one of similar or complementary sequence) hybridized to CD4$^+$ lymphocyte DNA isolated from the patient along with molecular size markers. These assays allow the physician to chart the course of the disease during the long intervening asymptomatic period, and to score the effectiveness of prophylactic therapeutics.

In order to determine whether TRF length is a useful marker in diagnosis of HIV infection, CD4$^+$ cell counting was performed on asymptomatic HIV-infected individuals, and compared to TRF length, measured as discussed above. As shown above, peripheral lymphocytes start with around 10 kb TRF length at birth, and reach a TRF length of 5.0 at approximately age 120. The results were as follows:

A 30 year old HIV+ with a CD4 count of 476 had a TRF of 7.6.
A 46 year old HIV– control, had a TRF of 7.0.
A 34 year old HIV+ with a CD4 count of 336, had a TRF of 7.7.
A 46 year old HIV– control, had a TRF of 7.1.
A 32 year old HIV+ with a CD4 count of 448, had a TRF of 6.9.
A 33 year old HIV+ with a CD4 count of 358, had a TRF of 5.0 (i.e., at a length observed for senescent cells)

The results indicate that the 33 year old HIV+ patient has a senescent telomere length in his CD4+ cells, which means that they are at the end of their replicative capacity. In contrast, the CD4+ count provided no indication of the status of this patient. Indeed, one patient actually had a lower CD4+ count.

Two weeks after the assay was performed, this patient experienced a precipitous drop in CD4+ count, going from 358 to 159, and was therefore diagnosed AIDS, and rapidly acquired leukoplakia on the tongue. The other patients remain asymptomatic. Thus, this diagnostic procedure is able to distinguish patients near the end of the course of HIV infection, whereas the previously used marker (CD4+ count) could not.

The accelerated replicative senescence of CD4+ lymphocytes during the course of HIV infection provides an appropriate indication for therapies designed to forestall telomere shortening, e.g., utilizing the CTO oligonucleotide described above. In addition, as described above, CD4+ cells of an individual at an early stage of infection can be banked for later administration to the individual. The efficacy of drugs, such as AZT, may also be determined to study whether the drug slows the rate of proliferation of CD4+ cells, and is thus useful at all stages of the disease. If not, it can be administered only when necessary during the course of the disease.

Example 9
Telomere Shortening in Human Mammary Epithelial(HME) Cells

Referring to FIG. 12, when digested with a restriction enzyme having a 4-base recognition site (like Hinf1), most genomic DNA is digested into small fragments. However, because the repetitive telomeric sequences lack restriction sites, telomeres retain relatively large terminal restriction fragments (TRFs) composed of 2–5 Kb of subtelomeric DNA and age-dependent amounts of telomeric repeats. As previously described for human fibroblasts, lymphocytes and endothelial cells, telomere length shortens in normal human mammary epithelial cells during in vitro cellular senescence (compare TRF length in lanes 1 (PDL 21) and 2 (PDL 40)). In human mammary epithelial cells expressing E6 of human papilloma virus 16, the TRF length continues to shorten during the extended lifespan period until crisis and subsequently immortalization occurs (lane 3 (PDL 68)). The TRFs generally stabilize in immortalized cells (lane 4 (PDL 81) and lane 5 (PDL 107)) consistent with the re-expression of telomerase activity.

Example 10
Slowing Telomere Loss in Mammary Epithelial Cells Results in Increased Replicative Lifespan Normal human mammary epithelial cells can be established from organoids (obtained from reduction mammoplasty) and can be cultured in defined condition in a standard medium (MCDB170) devoid of serum. Epithelial cells with typical cobblestone morphology spread around organoids plated in this medium. After the first subcultivation these cultures enter a period of growth arrest for 2–3 weeks until a population of small, highly birefringent and rapidly dividing cells expand among larger cells. The medium (MCDB 104) apparently selects for a less differentiated cell type with increased growth potential. These cells can be subcultured for 40–45 additional doubling before undergoing cellular senescence.

As in Example 1, the change in proliferative lifespan and rate of telomere shortening in cultured mammary epithelial cells treated with the indicated amounts of CTO (occasionally referred to as C-Rich Terminal Repeat (CTR)) versus control random oligonucleotides. Normal human mammary epithelial cells from a donor (31) were infected with the E6 gene of human papilloma virus 16. This gene product binds p53 protein and permits HME31 cells to have extended life span by proliferating from PDL 42 to PDL 62 when crisis occurs. During this extended lifespan period the TRFs shorten from an average of approximately 5 kb to 2.5 kb (compare in FIG. 12 HME31 PD 40 to HME31E6 PD 68).

As is demonstrated in FIG. 13, experiments initiated using HME31E6 cells at PDL 36 were cultured in the presence of 3, 10, 30 and 100 $\mu$M CTO. As controls the cells were cultured without oligonucleotides (nil) or with 30 $\mu$M random oligonucleotide. FIG. 13 demonstrates that compared to the nil control and the 30 $\mu$M random oligonucleotide, there was a dose related retardation of TRF shortening between PDL 36 and 50. This is most easily seen by examining the subpopulation of telomere TRFs that migrate more slowly than the rest, giving a discrete trailing band. Cells were maintained in logarithmic growth with medium changed and fresh oligonucleotide added three times per week.

Human mammary epithelial cells expressing HPV16 E6 bypass M1 and have extended replicative lifespan. HME31 cells normally senesce at PDL 42–45. When expressing E6 they will bypass M1 and divide until they reach crisis (M2) at PDL 53–62. The TRFs in HME31 (E6) cells at PDL 40 are approximately 5–6 Kb while at PDL 62 they are 3–4 Kb (see FIG. 12). As is demonstrated in FIG. 17, experiments initiated using HME31E6 cells at PDL 36 were cultured in the presence of 30 $\mu$M and 100 $\mu$M CTR in defined medium without serum. As controls, the cells were cultured without oligonucleotide (control), or with a 30 $\mu$M random oligonucleotide with the base content matched to the CTR oligonucleotide. FIG. 17 demonstrates that compared to the control and the 30 $\mu$M random oligonucleotide, there was a dose-related extension of the replicative lifespan in cells treated with CTR oligonucleotides. The control cells divided approximately 20 times during the experiment, whereas the CTR-treated cells divided at least 40–50 times. These results correlate well with the retardation of telomere shortening observed in FIG. 13.

Example 11
Extension of Life Span of IMR90 Fibroblasts

Referring to FIG. 14, IMR-90 lung fibroblasts TRF at PDL 30 were treated with 10 $\mu$M, 30 $\mu$M or 100 $\mu$M phosphodiester CTO or with only media addition (control). The cells were cultured in medium containing regular defined supplemented calf serum. The cells were passaged in 24 well dishes and subcultivated by trypsinization upon reaching confluency at 25,000 cells per well. The cells were fed medium containing oligonucleotides at various concentrations daily. As a control, cells were fed identical medium without oligonucleotides. As is illustrated in FIG. 14, there was approximately a 12–15% extension of total life span with CTO. In these experiments the control cells divided approximately 15–18 times during the experiment, whereas the treated cells divided 23–26 times. IMR-90 telomeres shorten approximately 50 b.p. per division and the TRF length of the control IMR-90 fibroblasts at senescence was approximately 9 kb. Since the 100 $\mu$M CTO-treated IMR-90 cells senesced at PDL 55, the predicted difference in the rate of TRF loss between the control and the 100 $\mu$M CTO (9 kb vs 9.4 kb) is too small to be resolved using current techniques.

Example 12
GTO Experiments

As in Example 2, an immortalized human fibroblast cell line, IDH4, which has very short TRFs, was incubated with GTO oligonucleotide. Referring to FIGS. 15 and 16, cells were incubated in regular culture medium containing serum in the presence of 10 $\mu$M, 30 $\mu$M and 100 $\mu$M GTO. The cells were fed fresh phosphodiester GTO oligonucleotide every other day and subcultured when confluent for a total of 90 days. The cells were still growing in GTO after 90 days at all concentrations used even though they grew more slowly at the higher GTO concentrations and went through fewer population doubling (control, 45 PDL; 10 $\mu$M GTO 40 PDL; 30 $\mu$M 35 PDL; 100 $\mu$M 25 PDL). When TRF analysis was performed after 90 days the IDH4 cells regained TRF length in a dose dependent manner with 30 $\mu$M and 100 $\mu$M being approximately the same (FIG. 15). This suggests that the presence of excess single-stranded TTAGGG DNA in the cell was probably influencing the feedback regulation of telomerase and actually increasing telomerase activity and extending telomere length. The control and 30 $\mu$M GTO were passaged without oligonucleotide addition for an additional 90 days (approximately 35–40 PDL). As is illustrated in FIG. 16, the TRFs slowly shorten.

These data and those in Example 2, indicate that cell lines differ in their response to GTO oligonucleotide. Thus, prior to use of such an oligonucleotide in therapeutic compositions it is important to ensure that the target cells respond as desired. Should the effect seen above occur, then the oligonucleotide should be chosen to change the response to that shown in Example 2. This can be done by choosing an oligonucleotide which binds to telomerase at a different site from that bound by GTO. Applicant believes that the effect observed above is caused by binding of GTO to required proteins, allowing telomerase to be active to expand the telomeres. Thus, by choosing an oligonucleotide which does not bind such proteins the desired effect of reducing telomerase activity can be achieved.

Example 13
Small Molecule Inhibition of Telomerase

The following is an example of a method for screening for activity of small molecules as inhibitors of telomerase. Similar examples will be evident to those in the art. Compounds that can be screened include those which are not thought to be cytotoxic because they do not cause immediate cell death. Rather, such compounds act only after several generations of inhibition of telomerase activity. Thus, previous drugs tested by standard means should now be retested to determine their utility as claimed herein. Drugs which inhibit telomerase activity, or in some cases activate it in vivo (e.g. at the level of transcription) are useful in treatment of disease are discussed herein.

We analyzed the effects of various nucleoside analogs, which are chain-terminating inhibitors of retroviral reverse transcriptases, on *Tetrahymena thermophila* telomerase activity in vitro, and on telomere length and maintenance, cell division and conjugation of Tetrahymena cells in vivo. In vitro assays of telomerase activity showed that arabinofuranyl-guanosine triphosphate (Ara-GTP) and ddGTP were both very efficient inhibitors of incorporation of labeled nucleotides into telomeric DNA repeats, even at low inhibitor concentrations, while azidothymidine triphosphate (AZT-TP), dideoxyinosine triphosphate (ddITP) or ddTTP were less efficient inhibitors of incorporation. All of these nucleoside triphosphate analogs, however, produced analog-specific alterations of the normal banding patterns seen upon gel electrophoresis of the synthesis products of telomerase, suggesting that the competitive and/or chain terminating action differed at different positions along the RNA template.

The effects of these analogs in nucleoside form on Tetrahymena cell growth, conjugation, and telomere length were tested. Although cell division rates and viability were unaffected after several weeks in culture with Ara-G, telomeres were consistently and rapidly shortened in cultures containing AZT or Ara-G, and growth rates and viability of a fraction of cells were decreased in AZT. In short-term experiments with cultures containing ddG, ddI, or 3' deoxy-2',3'-didehydrothymidine (d4T), d4T also showed shortened telomeres. ddG or ddI had no effect on telomere length. AZT, Ara-G, Acycloguanosine (Acyclo-G), ddG and ddI were added to conjugating cells, but none showed any irreversible disruption of conjugation or macronuclear development, as shown by quantitation of the efficiency of formation of progeny cells. PCR analysis of DNA from cells mated in AZT did show a decrease in the formation of 11 Kb rDNA, a marker for telomere addition during Macronuclear developement.

The following materials and methods were used to obtain these results:

*Tetrahymena thermophila* strains SB210(VI) and PB9R (II), where numbers in parentheses indicate mating type, were maintained as stocks at room temperature in 1% PPYS (1% proteose peptone (Difco), 0.1% yeast extract (Difco) and 0.0015% Sequestrine (Ciba-Geigy)). Stocks were passaged every three to four weeks.

For analysis of macronuclear DNA from cultures containing the nucleoside analog AZT (Sigma), or controls lacking analog, at various timepoints during vegetative divisions, cells from stationary stock cultures were inoculated into 25 ml thymine-deficient Iso-sensitest broth ('Isobroth', Oxoid USA) in 250 ml flasks. Cultures were incubated at 30° C. with shaking (100 rpm) for 48 hours. Cells were counted and plated at 1000 cells/1.5 ml in 24-well plates (Falcon) and grown at 30° C., without shaking, for 48 hours. 5 $\mu$l of these log phase cells were used to inoculate 1 ml cultures (Isobroth) containing varied concentrations of nucleoside analog. Thereafter, every 2–4 days cells were transferred, either 5 $\mu$l per well, or 1–3 $\mu$l using a multi-pronged replicator into fresh 1 ml broth containing AZT. Remaining cells were pelleted and stored at −80° C. until processed for DNA analysis.

For analysis of macronuclear DNA from vegetative cultures containing the nucleoside analogs Ara-G (Calbiochem), ddG (Calbiochem), or ddI (Calbiochem), or controls lacking analog, stock cultures were grown overnight in 2% PPYS as described. Cells were counted and plated at 100 cells/2 ml in 2t PPYS containing varied amounts of analog, 1% DMSO (Fisher) (as a control for ddG and Ara-G), or 2% PPYS alone. Cells were replica plated into fresh medium every 2–6 days, and remaining cells were pelleted and stored at −80° C. until processed for DNA analysis.

For analysis of macronuclear DNA from vegetative cultures containing d4T (Sigma) or control lacking the analog, stock cultures (SB210 VI) were grown overnight in Isobroth as described. Cells were then counted and duplicate cultures inoculated at 500 cells/5 ml Isobroth in 50 ml conical tubes, and grown at 30° C., shaking 80 rpm. 500–2000 cells were transfered to fresh broth every 2–4 days, and the remainder pelleted and stored at −80° C. until processed for DNA analysis.

For analysis of rDNA from cells conjugated in the presence of nucleoside analogs, 50 ml overnight cultures (2%

PPYS) were starved by pelleting cells and resuspending in an equal volume of Dryl's solution before returning to 30° C. shaking (100 rpm) incubator for 18 hours. (1× Dryl's solution=0.5 g Na citrate, 0.16 g $NaH_2PO_4H_2O$, 0.14 g $Na_2HPO_4$ per liter, plus 15 ml of 9.98 g $CaCl_2 2H_2O/500$ ml). Cells were then counted and equal numbers mixed before pelleting (6 minutes in an IEC tabletop centrifuge, ¾ speed), and resuspended in Dryl's to 1.5–2×10⁶/ml. Cells were plated at an average density of 1.5 cells/well into 6-well plates (Falcon) and allowed to conjugate 6 hours, 30° C. without shaking. Mock-conjugated SB210 cells were treated identically but not mixed with PB9R cells. At 6 hours the cultures were checked for pairing (>90%, except SB210 controls) and either 1 ml Dryl's solution or 2% PPYS containing the nucleoside analog (Acyclo-G purchased from Sigma) or no added drug as control were added slowly with gentle swirling. Cultures were returned to 30° C. for an additional 18 hours before being harvested for DNA analysis.

For analysis of vegetative growth and macronuclear DNA from single-cell cultures containing the nucleoside analogs AZT or Ara-G, SB210 (VI) cells were grown from stationary stock cultures overnight at 30° C. with shaking (100 rpm) in 50 ml 2% PPYS or Isobroth. Cells were counted and added to the appropriate medium plus analog (Ara-G to 1 mM or DMSO to 1% as control in 2% PPYS; AZT to 10 µM or 1 mM, or no addition as control in Isobroth) and plated in 96-well plates (Falcon), 100 µl per well at a density of 1 cell per well. 5 plates were prepared for each analog or control. Wells were scored for cell growth and plates were replica plated every 1–2 days (Ara-G and DMSO plates) or every 2–4 days (AZT and Isobroth control plates) to maintain approximate inoculation densities of 1–10 cells per well for each passage. Occasionally individual wells were passaged by hand (1 µl inoculated per well using a pipettor) into several blank wells, to expand the number of live wells per plate as single-cell cultures were lost over time due to low probability of being transferred at each passage. After passaging, cells were pooled, pelleted and stored at −80° C. until processed for DNA analysis.

Total cellular DNA was prepared essentially as described by Larson 50 Cell, 477, 1987, except that the Hoechst 33258-CsCl gradient purification step was omitted.

Restriction digests, agarose gel electrophoresis, transfer of DNA to Nytran filters (Schleicher and Schuell), and hybridization with $^{32}$P-nick-translated or random-primed probes were carried out using standard procedures (Maniatis et.al. 1989). Telomere length was analyzed as described previously for Tetrahymena [Larson 50 Cell, 477, 1987].

For analysis of cycloheximide (CHX) sensitivity of cells conjugated in the presence of analog, 50 ml cultures of each cell type were grown overnight in 2% PPYS, starved in Dryl's for 18 hours, mated (5×10⁵cells/ml) for 6 hours, then analog was added. Cells were allowed to complete mating in the presence of the analog. Twenty-four hours after mixing, cells were diluted in Dryl's solution, counted and plated at 1 cell per well of 96-well plates in 1% PPYS without analog. Cells were grown for 4 days in a humid chamber at 30° C., without shaking. Cells were then replica plated into 1% PPYS plus 15 gg/ml cycloheximide, allowed to grow for four days before scoring, and percent of CHX-resistant wells was calculated. Because generation of progeny expressing the cycloheximide marker requires successful production of a new macronucleus, cells whose macronuclear development was disrupted by the analog are killed in CHX.

For PCR analysis of the 11 kb form of the rDNA from cultures conjugated in the presence of analog, 1.25 µM each of the telomeric primer $(C_4A_2)_4$ and a 25-mer rDNA primer (5' GTGGCTTCACACAAAATCTAAGCGC 3') located 1371 nucleotides from the 5' end of the rDNA were used in a "hot start" reaction containing 1 mM $MgCl_2$, 0.2 mM each dNTP, 1× PCR reaction buffer (Perkin Elmer Cetus), and 0.5 µl Amplitaq polymerase (Perkin Elmer Cetus). Sample DNA and polymerase were kept separate by the use of Ampliwax PCR Gem 100 wax beads (Perkin Elmer Cetus), following manufacturer's instructions. The samples were heated to 95° C. for 1 minute, and then cycled 40 rounds in a Perkin-Elmer thermocycler as follows: 1 minute at 94° C., 30 seconds at 58° C., 3 minutes at 68° C. Identical reactions were done using 3' micronuclear rDNA primers, 9610 nucleotides from the 5'end, and (5' CAATAATGTATTAAAAATATGCTACT-TATGCATTATC 3'), 10300 nucleotides from the 5' end.

Synthetic oligomers were prepared as described Greider 43 Cell, 405, 1985. Extracts were prepared as described by Blackburn et.al., 31 Genome 553, 1989.

A standard assay contained 50% by volume of heparin-agarose purified telomerase, 25 µM TTP, 1.25 µM $^{32}$P-labeled dGTP (400 Ci/mmol, Amersham), 1 µM oligo (either $(T_2G_4)_4$ or $(T_2G_4)_2$ mixed with water and heated at 90° C. for two minutes and cooled at 30° C. for 10 minutes), and 0.1 µl RNasin (40 U/ml, Promega) in a no-salt buffer. AZT-triphosphate was obtained from Burroughs Wellcome, N.C. Ara-G-triphosphate was purchased from Calbiochem and ddNTPs from Sigma. Reaction mixes were kept on ice until ready for use, and then mixed into tubes containing analog for incubation at 30° C. Reaction times were thirty minutes. Reaction rates under these conditions were determined previously to be linear over time for thirty minutes. Identical reactions were run without primers as controls. The reactions were then processed essentially as described by Greider and Blackburn 337 Nature, 331, 1989. For quantitative assays, aliquots of the reaction mixture were spotted in triplicate onto DE81 paper and washed as described Greider 43 Cell, 405, 1985. Incorporation of $^{32}$" P label from either $^{32}$P-TTP or $^{32}$P-dGTP was measured to monitor the reaction rate. For visualization of the elongation reaction products, samples were heated to 95° C. for 2 minutes and cooled on ice before loading onto a 12% polyacrylamide/8 M urea gel.

The model for the mechanism of the telomerase ribonucleoprotein enzyme from Tetrahymena is shown in FIG. 18A. The enzyme synthesizes TTGGGG repeats onto the 3' end of a suitable DNA primer by copying a template sequence in the RNA moiety of the enzyme. For ease of reference in discussing the results, the residues in the template region are numbered 1 to 9 (5' to 3' along the RNA). The standard telomerase assay used in this example consists of incorporation of dGTP and TTP substrates, one triphosphate $^{32}$P-labeled, into synthesized DNA in the reaction shown in FIG. 18A. For the experiments discussed in this example we used as the DNA primer either 1 µM $(T_2G_4)_4$ or $(T_2G_4)2_1$, under conditions in which the overall rate of incorporation of label was determined previously to be linear over time. Incorporation of $^{32}$P label from either $^{32}$P-TTP or $^{32}$P-dGTP was measured to monitor the reaction rate, and the distributions of elongation products were analyzed by denaturing polyacrylamide gel electrophoresis.

Figure 19A:
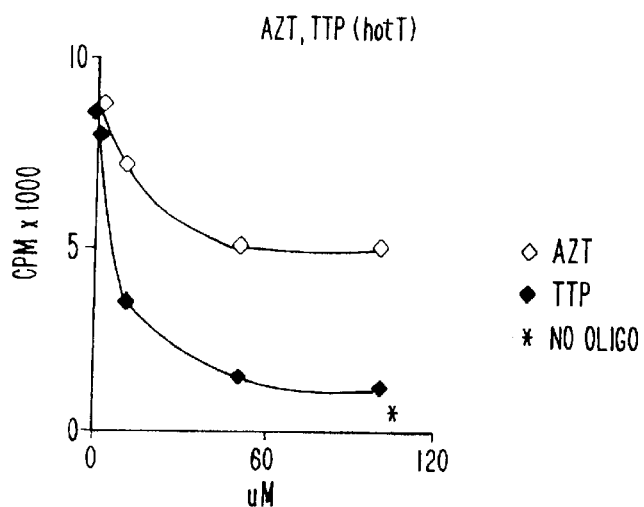
Figure 19B:
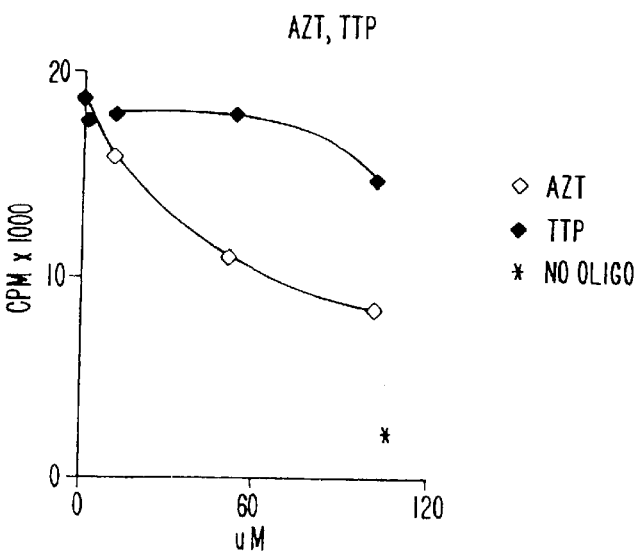

The effect of adding increasing amounts of AZT-triphosphate (AZT-TP) to the standard assay for telomerase activity is shown in FIG. 19A. A series of control reactions using unlabeled TTP added at the same concentrations as the AZT-TP was run in parallel (FIG. 19A). The unlabeled TTP inhibits incorporation of the $^{32}$P-labeled TTP by simple competition. Quantitation of label incorporated into product in this experiment enabled us to determine the $K_m$ for TTP to be ~5 µM. Compared with addition of unlabeled TTP competitor, AZT-TP had only a modest quantitative effect on the incorporation of $^{32}$P-labeled TTP (FIG. 19A). Since AZT incorporation leads to chain termination, this result indicates that AZT-triphosphate competes less efficiently for telomerase than TTP. Similar results were obtained when incorporation of $^{32}$P-dGTP was monitored (FIG. 19B), with 50% inhibition occurring at ~80 µM AZT-TP.

Figure 19C:
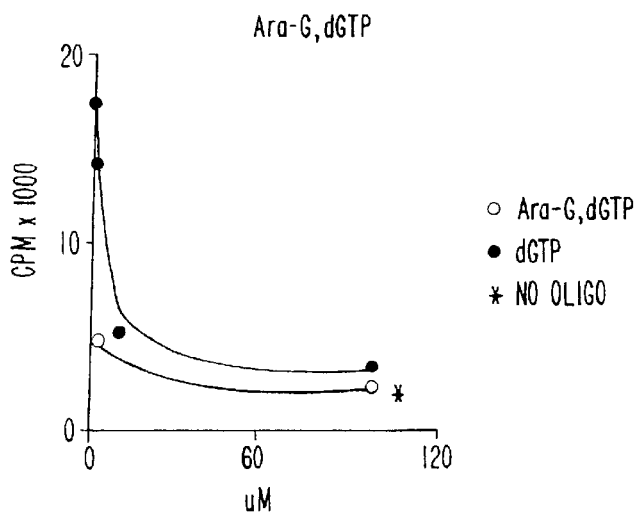
Figure 19D:
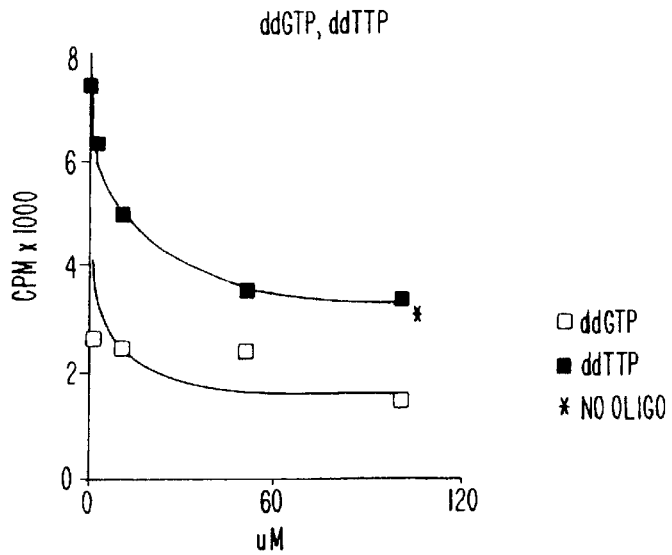
Figure 19E:
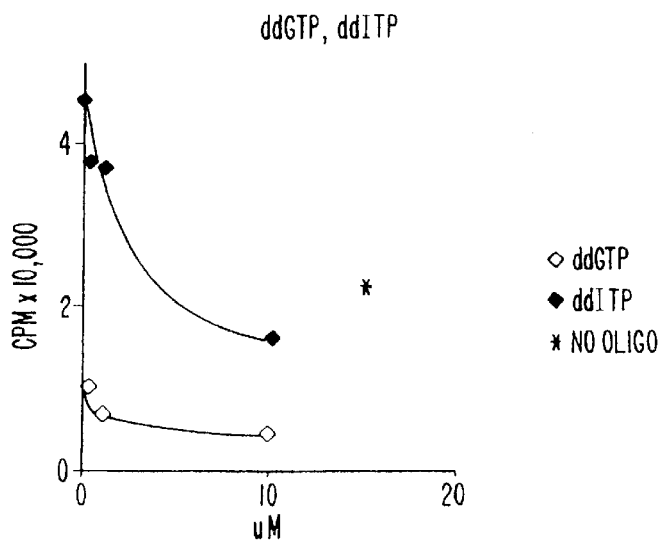
Figure 19F:
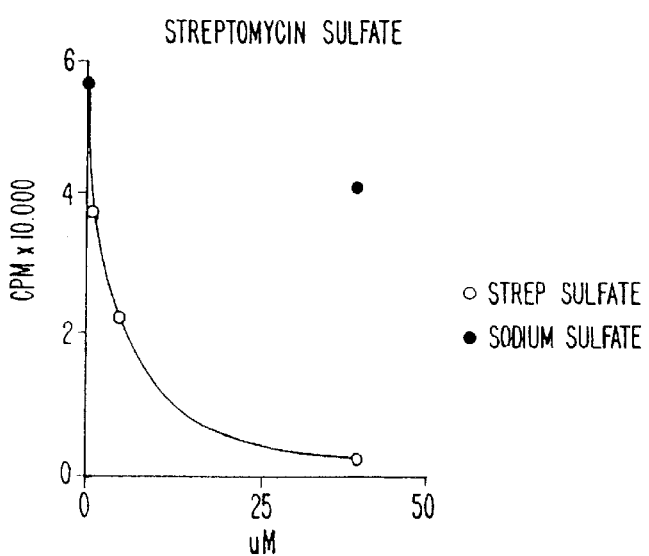

In similar experiments in which increasing concentrations of arabinofuranyl-guanosine triphosphate (Ara-GTP) were added to the reaction, significant reduction of overall incorporation occurred even at low concentrations of the analog (FIG. 19C). From parallel experiments in which unlabeled dGTP was added as competitor (FIG. 19C), the $K_m$ for dGTP under these reaction conditions was found to be 1–2 µM. 50% inhibition occurred with 0.7 µM Ara-GTP; thus Ara-GTP potentially competes as well as unlabeled dGTP for $^{32}$P-dGTP. However, as incorporation of Ara-G causes chain termination, each Ara-G incorporated is expected to have a greater impact on total incorporation than competition with unlabeled dGTP.

We also tested the effects of dideoxynucleoside triphosphates (ddNTPs) on the telomerase reaction. As shown previously for telomerase [Greider 43 Cell, 405, 19853, and as is the case for many other reverse trancriptases, ddNTPs are recognized by the enzyme and incorporated, causing chain termination with a subsequent shift in banding patterns and reduction of the average product length. Consistent with previous qualitative analyses of Tetrahymena and human telomerases [Greider 43 Cell, 405, 1985; Morin 59 Cell, 521, 1989], ddGTP and ddTTP each inhibited the incorporation of labeled $^{32}$P-NTP into elongation products (FIGS. 19D and E). ddGTP was a much more efficient inhibitor than ddTTP: under these reaction conditions 50% inhibition occurred at <0.1 and 5 µM ddGTP and ddTTP respectively. As observed previously for Tetrahymena telomerase (Greider 43 Cell, 405, 1985], no significant effects were seen with either ddCTP or ddATP. In addition, ddITP inhibited telomerase (FIG. 19E), although less efficiently than ddGTP, with 50% inhibition occurring at 3 µM ddITP.

The size distribution of labeled products was then analyzed by denaturing polyacrylamide gel electrophoresis. Consistent with the expectation for a chain-terminator, the proportion of longer telomerase products was decreased in the presence of AZT compared with cold TTP competitor controls (FIG. 20A; compare lanes 1 and 2 with lanes 3 to 5), and in the presence of Ara-G (FIG. 20A; lanes 7 and 8). Average product length also decreased in the presence of Ara-GTP, ddGTP and ddITP (FIGS. 20A and B). In addition, each nucleoside triphosphate analog produced distinctive and characteristic patterns of chain termination, as shown by analysis of the shifts in the banding patterns of the elongation products. With AZT-triphosphate, we saw increased relative intensities of the bands corresponding to the incorporation of T residues (copying the A residues at positions 2 and 3 on the template RNA (see FIG. 18A)). This change in banding pattern is consistent with simple chain termination, which is predicted to increase the intensity of bands corresponding to the position of both incorporated T residues. Similar effects were seen with ddTTP. We interpret this to mean that AZT-triphosphate was recognized by the enzyme and incorporated into the correct positions in the growing telomeric sequence, causing chain termination. However it cannot be excluded that the increase in relative intensity of the band corresponding to position 3 on the template, which precedes addition of the second T, is also attributable to pausing caused by competition with TTP and a slower reaction rate with AZT-triphosphate at position 2.

The results with Ara-GTP were also consistent with incorporation of Ara-G and consequent chain termination (FIG. 20A, lanes 7 and 8). Although there are four positions at which a G residue can be incorporated and therefore at which chain termination could occur, the strongest increase was in the band corresponding to the G residue specified by position 4, in the middle of the telomerase RNA template (see FIG. 18A). With ddGTP, chain termination appeared to occur most efficiently at positions 6 and 5 (FIG. 20B, compare lane 1 with lanes 4 to 6), and with ddITP, at position 5 (lanes 7 to 9).

FIG. 18B summarizes schematically the effects of the various triphosphate analogs on polymerization at each of the six positions along the template. There was no correlation between the efficiency of a nucleoside analog as an inhibitor and the position of its maximal chain termination on the template. For example, the potent inhibitors ddG- and Ara-G-triphosphates cause maximal chain termination at different positions on the telomerase RNA template (5 and 6 for ddG, and 4 for Ara-G).

In addition to nucleoside triphosphate analogs expected to act as chain terminators, we also tested rifampin, an inhibitor of bacterial RNA polymerase, and streptomycin sulfate. Streptomycin sulfate is known to inhibit the activity of group I self-splicing introns at high concentrations [von Ahsen 19 Nucl. Acids Res., 2261, 1991], and has a guanidino group that might be recognized by telomerase as part of the enzyme's specificity for G-rich DNA primers (Greider 51 Cell, 887, 1987). Adding rifampin at concentrations up to 100 µg/ml did not affect the quantitative incorporation of label or change the banding pattern of the elongation products. Streptomycin sulfate at 40 mM dramatically reduced the amount (FIG. 19F) and average length of elongation products, with little decrease in activity being seen in a 40 mM sodium sulfate control. However, unlike the nucleoside triphosphate analogs, inhibition by streptomycin did not appear to affect incorporation at specific positions in the repeat. The inhibition by streptomycin may be useful experimentally as a criterion for telomerase activity in vitro. However, the significance of the inhibition by streptomycin is unclear, as it is difficult to rule out that its effect is the result of nonspecific binding to either the RNA moiety of telomerase or the DNA primer.

Because the triphosphate forms of the analogs AZT, Ara-G, ddT, ddG and ddI each inhibited (with varying efficiencies) telomerase in vitro, we tested whether supplying each of these nucleoside analogs in the cell growth medium caused in vivo changes in telomere length or senescence. Additionally, Acyclo-G and d4T were tested on conjugating and vegetative cells, respectively.

Previous work with Tetrahymena showed that at least one alteration of the telomerase RNA causes telomere shortening and cellular senescence [Yu 344 Nature 126, 1990]. To test whether such a phenotype could be produced by inhibitors of telomerase in Tetrahymena, duplicate log-phase cultures were grown for prolonged periods in the presence of varying concentrations of analogs. The growth and cell morphology of these cultures were monitored, and DNA was isolated at different times for telomere length analysis. AZT at 5 or 10 mM added to Isobroth medium strongly inhibited cell growth and killed cells within a day, and thus at these concentrations acted in a manner suggestive of immediate toxicity to cells, rather than of senescence. AZT added to Isobroth medium at lower concentrations (up to 1 mM) did not result in senescence of cultures maintained by subculture of ~$10^3$ cells per transfer, over a 50-day period of continuous growth and subculturing of these cell cultures. From growth rate measurements it was calculated that the cells went through 150 to 250 cell generations in the course of this 50 day period. In similar mass transfer experiments no effects on cell doubling rate, morphology or long term viability were obtained with cells grown in 2% PPYS plus up to 2 mM Ara-G, the highest concentration tested that did not cause immediate toxicity.

Telomere lengths in cells grown in the presence of the different analogs were monitored by Southern blot analysis of DNA samples extracted at a series of time points during the subculturings. The telomeres of cells grown vegetatively in 1 and 5 mM AZT in 2% PPYS medium were reproducibly shortened by up to an average of 170 base pairs compared with the control cultures grown in 2% PPYS in the absence of the drug (FIGS. 21A and B). This shortening of telomeres occured in a concentration-dependent manner (FIG. 21B), with at least 50% of the maximal shortening effect occurring by 10 $\mu$M AZT, the lowest concentration tested. For each AZT concentration tested, the full decrease was seen within 3 days of culturing in the presence of the drug (15 to 30 cell divisions), but after this initial length adjustment, at each drug concentration telomeres thereafter showed no statistically significant shortening over time, and mean telomere length consistently remained static for at least 28 days of mass transfer subculturing.

Similar degrees and timing of telomere shortening were produced with 1 or 2 mM Ara-G added to 2% PPYS culture medium (FIG. 21C). d4T added to Isobroth culture medium in concentrations ranging from 10 $\mu$M to 1 mM produced shortened telomeres at 100 $\mu$M and 1 mM, again in a concentration dependent manner, after 5 days (16 generations) in culture. In contrast, up to 1 mM ddG or ddI produced no changes in telomere length compared with control cultures, over a period of 5 days of subculturing (15–20 cell generations) in 2% PPYS medium.

Because we had found previously that telomerase is strongly inhibited in vitro by at least some of the analogs tested, and telomere length is affected in vivo within an estimated 15 to 30 cell generations by these analogs, it was possible that telomere addition was in fact being disrupted in vivo, but that our failure to find any evidence of progressive telomere shortening or senescence was attributable to a subset of the cell population that escapes an inhibitory effect of the analog on telomerase. We have shown previously that impairing telomerase in vivo by mutating the telomerase RNA produced senescence in most cells, but only ~$10^2$ single cell subclones were analyzed in these experiments, [Yu 344 Nature 126, 1990]. Under our mass transfer subculturing regime, in which about $10^3$ cells were transferred per passage, if a fraction as small as ~1% of the cells escaped senescence, and if their growth advantage was sufficiently high compared with cells losing telomeres, they could become the predominant population in any cell passage and we would not have detected any phenotype.

To test whether we had missed such a subpopulation of cells, we carried out the same experiments on vegetatively dividing Tetrahymena cells in the presence and absence of drug, but in these experiments the subculturing was carried out by plating cells at an average of 1 to 10 cells per well in microtiter plate wells in the presence of 10 $\mu$M and 1 mM AZT, and 10 $\mu$M and 1 mM Ara-G. For each drug, cells were plated out in this manner for 30 consecutive days (90 to 150 cell generations) and 16 consecutive days (50 to 80 cell generations) respectively for the 10 $\mu$M and 1 mM drug concentrations. DNA was isolated at intervals from combined samplings of the wells for analysis of telomere length.

Compared with control medium lacking the nucleoside analog, no changes in the plating efficiency were observed over the course of the experiment for cells grown in 10 $\mu$M AZT and 10 $\mu$M or 1 mM Ara-G. However, in the presence of 1 mM AZT, monitoring growth rates of c ells maintained in this way by single cell transfers allowed us to identify two general growth classes, which we designated as slow (0 to 1 cell doubling per day) and fast (2 to 4 cell doubling per day). The growth rate of fast cells was similar to that of the controls grown in Isobroth containing no AZT. Over time, the proportion of wells with slow cells decreased, as would be expected if they simply had a lower probability of being transferred, since they were present in lower cell densities than fast cells, which grew to higher cell densities and for which the timing of the plating protocols had been worked out. However, monitoring the cells remaining in wells after transfers had been made from them showed that the slow cells lost viability over time. In addition, throughout the course of the transfers, slow cells appeared from formerly fast cell wells. We pooled cells from the slow growing wells (pooling of several microfiter wells was necessary to obtain sufficient DNA for Southern analysis) and compared there telomere length distribution with that of pooled fast cells. The mean length and size distribution of telomeric DNA from pooled fast cells were indistinguishable from those of control cells grown without AZT. In contrast, the pooled slow cell DNA showed a slight decrease in mean telomere length and heterogeneity (FIG. 21D). Control cells grown in Isobroth medium had telomeres that were an average of 165 bp shorter than cells grown in 1% PPYS medium. We believe that because the telomeric $G_4T_2$repeat tracts in cells grown in Isobroth medium are already markedly shorter than those of cells grown in the richer PPYS medium, the additional amount of telomere shortening caused by growth in 1 mM AZT is sufficient to reduce continually and stochastically a fraction of the telomeres below a critical lower threshold required for function, thus causing the decreased viability of a subpopulation of the cells.

We examined the effects of AZT, Ara-G, Acyclo-G, ddI and ddG on progeny formation by cells that have undergone conjugation. This process involves de novo formation of new macronuclear telomeres in the progeny cells. Macronuclear development in ciliated protozoans such as Tetrahymena involves developmentally programmed, site-specific fragmentation of germline chromosomes into linear subchromosomes, whose ends are healed by de novo addition of telomeres. We showed previously that telomerase not only elongates pre-existing telomeres in vivo during vegetative cell divisions [Yu 344 Nature, 126, 1990], but also functions to directly add telomeric DNA onto non-telomeric sequences during this developmentally-controlled chromosome healing. Because of the immediate requirement for telomere addition to fragmented DNA, it is possible that the latter process might be more sensitive to telomerase inhibition than telomere maintenance during vegetative growth. To test whether nucleoside analogs cause inhibition of macronuclear development due to a disruption of telomere formation, we mated two strains of Tetrahymena which are sensitive to cycloheximide, but whose progeny after mating are resistant to cycloheximide. Synchronized mated cells were treated with AZT at concentrations ranging from 10 $\mu$M to 5 mM for a period beginning just prior to when macronuclear development begins and continuing during macronuclear development (the period 6–24 hours after mating was initiated). At this point cells were diluted out in microtiter plate wells in fresh medium lacking the analog, at an average cell density of one cell per well, and allowed to grow for the minimum period before selection for cells that had successfully produced progeny. In attempts to maximize the effect of AZT, cells were either refed at 6 hrs with 2%

PPYS or Isobroth, or starved until 24 hrs (the duration of the AZT treatment). Such starvation arrests macronuclear development at an intermediate stage. When refed, macronuclear development would then be forced to proceed in the presence of the AZT. Control, unmated parental cells were also plated and exposed to drug. Similar experiments were performed with Ara-G, Acyclo-G, ddI and ddG. The results are shown in Table 4.

The control plates showed 99%–100% cell death in CHX, while the majority of cells that were mated with or without analog survived. None of the nucleoside analogs had any statistically significant effect on progeny formation. The design of this experiment would prevent takeover of the culture by a minority population that evaded the effects of the drug, as described above. Therefore little or no irreversible disruption of macronuclear development due to impaired telomerase activity and telomere formation occurred in the presence of AZT, Ara-G, Acyclo-G, ddG, or ddI.

Although macronuclear development was not significantly disrupted, analysis of the formation of a marker for telomere addition during macronuclear development suggests that AZT reduces the efficiency of telomere addition.

DNA from cells mated in the presence or absence of analog, and either refed at 6 hours or starved fully for the duration of conjugation were used in PCR with a telomeric primer and a 5' rDNA primer. This selected for a fragment of the 11 kb rDNA to which telomeres had been added. The 11 kb rDNA is either a by-product of the 21 kb rDNA formed during macronuclear development or an intermediate of this process. It is present only transiently during new macronuclear development and as such is a good marker for telomere addition in vivo. Knock-down of relative amounts of the 1400 nucleotide PCR-generated fragment from 11 kb-rDNA was seen in DNA from cells conjugated in the presence of AZT, but not in those containing Ara-G, Acyclo-G, $H_2O$ or DMSO controls or in mock-conjugated SB210 cells. To show that the DNA used in the PCR reactions was present and competent for PCR, identical reactions were run using primers from the 3'-micronuclear copy of the rDNA. In all samples the expected 810 nucleotide fragment was produced in substantial quantities (FIG. 22), indicating that the decrease in the 1400 nucleotide telomere-containing PCR product in samples from cells mated in AZT is due to the presence of analog rather than contaminants in the DNA or reagents. Southern blotting with a 5'-rDNA probe confirmed that the telomere-containing PCR product was from the expected rDNA sequence, (FIG. 22B) and no cross-hybridization occurred to the 3' PCR product. An overall decrease in telomere-containing PCR products was seen in all samples that were re-fed at 6 hours post-mixing, but the decrease was more pronounced in samples that had been mated in the presence of AZT.

TABLE 6

Effects of nucleoside analogs on progeny formation.

| CELL TREATMENT | # CHX-R | # TOTAL | % CHX-R |
| --- | --- | --- | --- |
| SB210 (NOT MATED) | 1 | 215 | 0.5 |
| PB9R (NOT MATED) | 3 | 307 | 1 |
| AZT (mM) | | | |
| 0 | 139 | 212 | 66 |
| 0.01 | 121 | 169 | 72 |
| 0.1 | 100 | 148 | 68 |
| 1.0 | 91 | 166 | 55 |

TABLE 6-continued

Effects of nucleoside analogs on progeny formation.

| CELL TREATMENT | # CHX-R | # TOTAL | % CHX-R |
| --- | --- | --- | --- |
| 5.0 | 75 | 120 | 63 |
| SB210 (NOT MATED) | 0 | 57 | 0 |
| AZT (mM) | | | |
| 0 | 165 | 214 | 77 |
| 0.01 | 67 | 92 | 73 |
| 0.1 | 128 | 190 | 67 |
| 1.0 | 60 | 125 | 48 |
| 5.0 | 89 | 168 | 53 |
| 1% DMSO | 84 | 109 | 77 |
| ARA-G (mM) | | | |
| 0.01 | 114 | 141 | 81 |
| 0.1 | 134 | 167 | 80 |
| 1.0 | 89 | 161 | 55 |
| 1% DMSO | 51 | 75 | 68 |
| ARA-G (mM) | | | |
| 1.0 | 51 | 86 | 59 |
| 2.0 | 40 | 92 | 43 |
| SB210 (NOT MATED) | 0 | 9 | 0 |
| PB9R (NOT MATED) | 0 | 37 | 0 |
| ddI (mM) | | | |
| 0 | 63 | 75 | 84 |
| 0.001 | 59 | 71 | 83 |
| 0.01 | 85 | 96 | 89 |
| 0.1 | 83 | 106 | 78 |
| 1.0 | 100 | 110 | 91 |
| 1% DMSO | 21 | 44 | 48 |
| ddG (mM) | | | |
| 0.001 | 86 | 102 | 84 |
| 0.1 | 73 | 86 | 85 |
| 1.0 | 51 | 66 | 77 |
| ACYCLO-G (mM) | | | |
| 0 | 36 | 45 | 80 |
| 0.017 | 80 | 107 | 75 |
| 0 | 78 | 116 | 67 |
| 0.017 | 101 | 146 | 69 |

Example 14

G-Reaction for Reducing the Size of the Terminal Restriction Fragment

Human fibroblast DNA digested with restriction enzymes, electrophoresed, and hybridized by Southern blot makes possible the resolution of terminal restriction fragments (TRFs) which in turn reflect the relative length of telomeric repeat sequences (See FIG. 26, HinfI digested DNA, labeled "HinfI"; DNA not digested, labeled "0"). This Southern analysis is complicated by the fact that human and many other species have long stretches of subtelomeric repetitive sequences that add to the TRF size. As a means of eliminating the artifactual inclusion of this subtelomeric repeats in a measurement of telomeric repeat length, a modified Maxam-Gilbert reaction is employed to hydrolyze the DNA at G residues. In the lane labeled "P only" (underloaded) the DNA is treated with piperidine in mild conditions which does not in itself decrease the size of the DNA. In the lane labeled "P+DMS" the samples are pretreated with DMS. Not the substantial reduction in TRF size compared to the HinfI digest relecting the deletion of subtelomeric sequences in the C-rich strand containing G residues. All lanes were probed with $(TTAGGG)_3$. This assay is thus useful for analysis of telomere lengths in diagnostic procedures.

Example 15

Fungal telomeres

The following example illustrates various specific telomeric sequences which can be used to identify specific fungi. Those in the art will recognize that such sequences can be probed with oligonucleotides to specifically diagnose the presence of a selected fungus. In addition, specific treatment of fungi can be effected by use of agents which bind to such sequences and reduce the long term viability of the fungal cell.

As described herein telomeric DNA is an attractive target for specific drug therapy. Telomeres are short single-stranded protrusions which are accessible to specific drugs. Binding by such drugs will interfere with normal telomere function and thus fungal cell viability. In similar experiments (routine to those in the art when conducted as described herein) inhibitors or facilitators of such telomere replication (or telomerase activity) can be discovered and used as anticancer, antiparasite and antifungal agents.

The-significantly increased length of fungal telomeres makes them ideal targets for antisense therapy or diagnosis. In addition, this different telomere structure indicates a different mechanism of action of the telomerase, and thus its availability as a target for antifungal agents which are inactive on human or other animal cells.

Telomeric DNA sequences have generally been found to be remarkably conserved in evolution, typically consisting of repeated, very short sequence units containing clusters of G residues. Recently however the telomeric DNA of the budding yeast Candida albicans was shown to consist of much longer repeat units. Here we report the identification of seven additional new telomeric sequences from budding yeasts. Although within the budding yeasts the telomeric sequences show more phylogenetic diversity in length (8 –25 bp), sequence and composition than has been seen previously throughout the whole phylogenetic range of other eukaryotes, we show that all the known budding yeast telomeric repeats contain a strikingly conserved 6 bp motif of T and G residues resembling more typical telomeric sequences. We propose that G clusters in telomeres are conserved because of constraints imposed by their mode of synthesis, rather than by a fundamental requirement for a specific common structural property of telomeric DNA.

The DNA sequences of telomeres, the ends of eukaryotic chromosomes, have been found previously to be conserved even between very diverse eukaryotes, typically consisting of tandem arrays of 5–8 bp repeating units characterized by clusters of G residues, producing a marked strand composition bias. However, the telomeric repeats of the opportunistic pathogen Candida albicans were shown to consist of homogeneous repeats of a 23 bp sequence that lacks any noticeable strand composition bias.

To determine the relationship of the apparently exceptional, complex telomeric repeat sequence of Candida albicans to the more usual, simple telomeric sequences, genomic DNA from budding yeast species related to both *C. albicans* and *S. cerevisiae* were analyzed by Southern blotting, using cloned *C. albicans* telomeric repeats as the hybridization probe. Under low-stringency hybridization conditions we detected multiple cross-hybridizing bands in several species FIG. 28. In some cases, the cross-hybridizing bands clearly were broad, a characteristic feature of telomeric restriction fragments caused by different numbers of telomeric repeats in individual telomeres among a population of cells.

Telomere-enriched libraries were constructed from genomic DNA from seven budding yeast species and strains. Telomeric clones were identified by their ability to hybridize to known yeast telomeric repeats (either the 23 bp *C. albicans* repeat or the $TG_{1-3}$ repeat of *S. cerevisiae*), or by screening for end-linked repetitive DNA sequences without the use of a specific probe. Sequencing putative telomere fragment inserts from seven species identified clones that contained tandem repeats with unit lengths of 8–25 bp. With a single exception, the repeats showed no sequence variations within a species. In every case the repeat array was present at the very end of the insert, directly abutting vector sequences, as would be expected for cloned telomeres. The repeat-containing clone from each species hybridized back to the same pattern of restriction fragments observed originally with the *C. albicans* or the *S. cerevisiae* probe used for library screening. Most of the bands were preferentially sensitive to Bal31 nuclease (FIG. 29) indicating that the bulk of the repeat sequences are present at the ends of chromosomes. The lengths of the tracts of repeats cloned from the different yeast species were typically between 250–600 bp, although those from the two *C. tropicalis* strains were only 130–175 bp. That this species has particularly short telomeres is also supported by their very rapid loss during Bal31 digestion and by the relatively weak hybridization, even with species-specific telomere probes.

FIG. 30 shows an alignment of these newly discovered telomeric repeat unit sequences together with those of *C. albicans* and *S. cerevisiae*. Two striking features are apparent: the much greater variety of the budding yeast telomeres, with respect to repeat unit lengths and sequence complexities, compared to other eukaryotes, and a conserved six-base cluster of T and G residues that most resembles typical telomeric sequences.

The sequence relationships among the telomeric repeats are generally consistent with the phylogenetic relationships of these budding yeasts. The telomeric repeats of the two *C. tropicalis* strains differ by only a single base polymorphism. The 25 bp telomeric repeats of the closely related *K. lactis* and *C. pseudotropicalis* differ at only one position. The telomeric repeat sequences from *C. albicans, C. maltosa, C. pseudotropicalis, C. tropicalis* and *K. lactis* are 23–25 bp in length, with differences largely or entirely confined to the central part of the repeat. The 16 bp repeat unit from *C. glabrata,* the species in this study that may be most closely related to *S. cerevisiae,* is very G-rich, which probably contributes to its cross-hybridization to the heterogeneous and smaller *S. cerevisiae* telomeric repeats. All the budding yeast sequences, including the irregular *S. cerevisiae* repeats, have a perfect or ⅚ match to a 6 bp T/G sequence (boxed) X In the cloned telomere from *C. tropicalis* strain B-4414, we found two telomeric repeat sequences that differed at the second base position of the repeat, as shown in FIG. 30 repeat units in the B-4414 telomere were homogeneous (and will be termed the "AC repeat"), but the remaining repeat (henceforth termed the "AA repeat") was identical to the homogeneous telomeric repeats cloned from strain *C. tropicalis* B-4443.

To determine the distribution of these variant repeats among the telomeres and strains of *C. tropicalis,* genomic DNA from several *C. tropicalis* strains including B-4414 and B-4443, and a control *C. albicans* strain were probed with oligonucleotide probes specific for either the AA or the AC repeat (FIG. 31 left panel). Only strains B-4414 and 1739-82, and to some extent the *C. albicans* telomeres, hybridized with the AC repeat-specific oligonucleotide probe (FIG. 31 left panel). However, genomic DNA from all of the *C. tropicalis* strains tested, including B-4443, but not from *C. albicans*, hybridized well with the oligonucleotide specific for "AA" repeats (FIG. 31 right panel). These results clearly indicate that both B-4414 and 1739-82 contain at least two forms of telomeric repeats, which are most likely variably interspersed in different telomeres, as signal rations with the two probes differed between individual telomeric fragments (FIGS. 31A and B, lanes 1 and 2).

Example 16
Effects of Telomerase Inhibitors on Human Tumor Cell Growth

Agents that were shown to inhibit telomerase from Tetrahymena e.g., AZT, ddG, and ara-G were tested to determine their effect on human telomerase activity, telomere repeat length, and cell growth immortality. Of the compounds tested ddG and ara-G were effective inhibitors of human telomerase obtained from the tumor cell line 296. The data for ddG is shown in FIG. 27. The effect of the agents on telomerase activity in intact cells was then studied utilizing the lymphoma cell line JY 616 which were maintained in RPMI 1640 with 0.25M Hepes, 10% FCS, and penicillin/streptomycin (Gibco). The cells were cultured in 6-well plates (Falcon) with 5.0 ML of medium per well in duplicate. Cells were passaged every 7–10 days which corresponded to 5–7 mean population doublings (MPD), and seeded at $3 \times 10^4$ cells per well into fresh medium containing analog or control. Cell viability was monitored prior to harvest utilizing trypan blue stain (Gibco) during counting with a hemocytometer. The average ratio of stained: unstained cells (dead:alive) was >90%. The intactness of the DNA was measured on a parallel gel by observing its mobility in a gel prior to digestion by a restriction enzyme.

As seen in FIG. 23, all JY cells grew in an immortal fashion in the presence of a low concentration of the potential telomerase inhibitors. At high concentrations (FIG. 24), the cells ceased proliferating in the presence of 50$\mu$M AZT and displayed a slowed growth in the presence of 20$\mu$M ara-G. In support of the belief that this inhibition of cell growth in the presence of 50 $\mu$M AZT, is due to telomerase inhibition, is the observation that the cells grew at a normal rate until week 3 and then ceased dividing. This is the effect one would expect if the inhibition of cell growth was via telomerase inhibition (i.e., the cells require multiple rounds of cell division to lose their telomeric repeats). Also in support of the belief that AZT inhibited the growth of the cells via the inhibition of telomerase is the finding shown in FIG. 25 where compared to week 1, and week 3 where the cells stopped dividing, the AZT treated cells had a marked decrease in mean telomere length compared to the control medium "R" at the same time.

In addition, 10 $\mu$M ddG was shown to cause a decrease in telomere length compared to the control (in this case a DMSO control). In FIG. 32 it can be seen that JY cells studied in a manner similar to that described above, and treated with ddG, showed a markedly shorter telomere repeat length after 9 and 10 weeks compared to the DMSO control. It should be noted that while JY cells are immortal, when cultured under the conditions described, they lose some telomeric repeats over 10 weeks. The addition of ddG markedly accelerated this loss.

Example 17
Assay for Telomerase Inhibitors Utilizing Human Telomerase

The following is a micro assay for the rapid MC screening of potential inhibitors of human telomerase. The reaction consists of the following components (given as a final concentration in 10 $\mu$l reaction volume): 1× Human Telomerase Buffer (HTB; 50 mM Tris.Cl pH 7.5, 1 mM Spermidine, 5 mM β-mercaptoethanol (BME), 5S 1 mM MgCl$_2$, 50 mM potassium acetate (K-OAc), 2 mM DATP, dTTP, 0.625 $\mu$M [$^{32}$P]-dGTP (800 Ci/mmol, 10 mCi/ml stock), 1 $\mu$M (TTAGGG)$_3$, 1 $\mu$l test compound, 5 $\mu$l of 1:5 diluted 293 S-100 extract, and diethylpyrocarbonate(depc)-treated H$_2$O to 10 $\mu$l.

The HTB, dATP, dTTP, 293 S-100 diluted extract, oligo and depc H$_2$O are combined, and aliquots are distributed to individual wells of a 96-well micro-titer plate. Different concentrations of the test compound are added to the wells and the plate is preincubated at 30° C. for 20 minutes to allow for inhibition to occur. The [$^{32}$P]-dGTP is then added to the wells, and the reactions are incubated at 30° C. for a further 30–60 minutes. At the end of this time, duplicate aliquots are spotted onto DE81 filter paper and allowed to dry. The filter paper is then washed extensively in 0.5M Na$_2$HPO$_4$ to wash away the unincorporated label, and briefly rinsed in water before drying. The filter is then exposed to a phosphorimaging screen for 30–60 minutes, and the samples are quantitated.

By comparing the sample signal to the RNase pretreated controls and the no extract controls, a percent decrease in telomerase-generated signal can be calculated. Any sample causing a change in the amount of radioactivity detected is electrophoresed on a DNA sequencing gel to confirm inhibition and to observe the effect of the agent on telomerase processivity. This will include determining if the inhibitory effect is a direct effect on the telomerase enzyme, or on one of the other components in the reaction, by performing titrations of these components and observing the percent inhibition. When a direct in vitro effect on telomerase is detected, the inhibitor is then be tested on cultured cells and in animal models such as tumor-bearing nude mice. As seen in FIG. 27, ddG was shown to inhibit human telomerase in a dose-dependent manner. Similar results were obtained with ara-G.

Compositions

Compositions or products according to the invention may conveniently be provided in the form of solutions suitable for parenteral or nasal or oral administration. In many cases, it will be convenient to provide an agent in a single solution for administration.

If the agents are amphoteric they may be utilized as free bases, as acid addition salts or as metal salts. The salts must, of course, be pharmaceutically acceptable, and these will include metal salts, particularly alkali and alkaline earth metal salts, e.g., potassium or sodium salts. A wide variety of pharmaceutically acceptable acid addition salts are available. These include those prepared from both organic and inorganic acids, preferably mineral acids. Typical acids which may be mentioned by way of example include citric, succinic, lactic, hydrochloric and hydrobromic acids. Such products are readily prepared by procedures well known to those skilled in the art.

The agents (and inhibitors) of the invention will normally be provided as parenteral compositions for injection or infusion. They can, for example, be suspended in an inert oil, suitably a vegetable oil such as sesame, peanut, or olive oil. Alternatively, they can be suspended in an aqueous isotonic buffer solution at a pH of about 5.6 to 7.4. Useful buffers include sodium citrate-citric acid and sodium phosphate-phosphoric acid.

The desired isotonicity may be accomplished using sodium chloride or other pharmaceutically acceptable agents such as dextrose, boric acid, sodium tartrate, propylene glycol or other inorganic or organic solutes. Sodium chloride is preferred particularly for buffers containing sodium ions.

If desired, solutions of the above compositions may be thickened with a thickening agent such as methyl cellulose. They may be prepared in emulsified form, either water in oil or oil in water. Any of a wide variety of pharmaceutically acceptable emulsifying agents may be employed including, for example acacia powder, or an alkali polyether alcohol sulfate or sulfonate such as a Triton.

The therapeutically useful compositions of the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compositions will be provided in dosage unit form containing an amount of agent which will be effective in one or multiple doses to perform a desired function. As will be recognized by those in the field, an effective amount of therapeutic agent will vary with many factors including the age and weight of the patient, the patient's physical condition, the blood sugar level to be obtained, and other factors.

Administration

Selected agents, e.g., oligonucleotide or ribozymes can be administered prophylactically, or to patients suffering from a target disease, e.g., by exogenous delivery of the agent to an infected tissue by means of an appropriate delivery vehicle, e.g., a liposome, a controlled release vehicle, by use of iontophoresis, electroporation or ion paired molecules, or covalently attached adducts, and other pharmacologically approved methods of delivery. Routes of administration include intramuscular, aerosol, oral (tablet or pill form), topical, systemic, ocular, intraperitoneal and/or intrathecal. Expression vectors for immunization with ribozymes and/or delivery of oligonucleotides are also suitable.

The specific delivery route of any selected agent will depend on the use of the agent. Generally, a specific delivery program for each agent will focus on naked agent uptake with regard to intracellular localization, followed by demonstration of efficacy. Alternatively, delivery to these same cells in an organ or tissue of an animal can be pursued. Uptake studies will include uptake assays to evaluate, e.g., cellular oligonucleotide uptake, regardless of the delivery vehicle or strategy. Such assays will also determine the intracellular localization of the agent following uptake, ultimately establishing the requirements for maintenance of steady-state concentrations within the cellular compartment containing the target sequence (nucleus and/or cytoplasm). Efficacy and cytotoxicity can then be tested. Toxicity will not only include cell viability but also cell function.

Some methods of delivery, e.g., for oligonucleotides, that may be used include:

a. encapsulation in liposomes,
b. transduction by retroviral vectors,
c. conjugation with cholesterol,
d. localization to nuclear compartment utilizing antigen binding site found on most snRNAs,
e. neutralization of charge of oligonucleotides by using nucleotide derivatives, and
f. use of blood stem cells to distribute oligonucleotides throughout the body.

At least three types of delivery strategies are useful in the present invention, including: agent modifications, particle carrier drug delivery vehicles, and retroviral expression vectors. Unmodified agents may be taken up by cells, albeit slowly. To enhance cellular uptake, the agent may be modified essentially at random, in ways which reduces its charge but maintains specific functional groups. This results in a molecule which is able to diffuse across the cell membrane, thus removing the permeability barrier.

Modification of agents to reduce charge is just one approach to enhance the cellular uptake of these larger molecules. The structural requirements necessary to maintain agent activity are well understood by those in the art. These requirements are taken into consideration when designing modifications to enhance cellular delivery. The modifications are also designed to reduce susceptibility to enzymatic degradation. Both of these characteristics should greatly improve the efficacy of the agent.

Chemical modifications of the phosphate backbone of oligonucleotides will reduce the negative charge allowing free diffusion across the membrane. This principle has been successfully demonstrated for antisense DNA technology. In the body, maintenance of an external concentration will be necessary to drive the diffusion of the modified oligonucleotides into the cells of the tissue. Administration routes which allow the diseased tissue to be exposed to a transient high concentration of the oligonucleotide, which is slowly dissipated by systemic adsorption are preferred. Intravenous administration with a drug carrier designed to increase the circulation half-life of the oligonucleotides can be used. The size and composition of the drug carrier restricts rapid clearance from the blood stream. The carrier, made to accumulate at the site of infection, can protect the oligonucleotides from degradative processes.

Drug delivery vehicles are effective for both systemic and topical administration. They can be designed to serve as a slow release reservoir, or to deliver their contents directly to the target cell. An advantage of using direct delivery drug vehicles is that multiple molecules are delivered per uptake. Such vehicles have been shown to increase the circulation half-life of drugs which would otherwise be rapidly cleared from the blood stream. Some examples of such specialized drug delivery vehicles which fall into this category are liposomes, hydrogels, cyclodextrins, biodegradable nanocapsules, and bioadhesive microspheres.

From this category of delivery systems, liposomes are preferred. Liposomes increase intracellular stability, increase uptake efficiency and improve biological activity.

Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver agents to cells and that the agent remains biologically active.

For example, a liposome delivery vehicle originally designed as a research tool, Lipofectin, has been shown to deliver intact mRNA molecules to cells yielding production of the corresponding protein.

Liposomes offer several advantages: They are non-toxic and biodegradable in composition; they display long circulation half-lives; and recognition molecules can be readily attached to their surface for targeting to tissues. Finally, cost effective manufacture of liposome-based pharmaceuticals, either in a liquid suspension or lyophilized product, has demonstrated the viability of this technology as an acceptable drug delivery system.

Other controlled release drug delivery systems, such as nanoparticles and hydrogels may be potential delivery vehicles for an agent. These carriers have been developed for chemotherapeutic agents and protein-based pharmaceuticals.

Topical administration of agents is advantageous since it allows localized concentration at the site of administration with minimal systemic adsorption. This simplifies the delivery strategy of the agent to the disease site and reduces the extent of toxicological characterization. Furthermore, the amount of material to be applied is far less than that required for other administration routes. Effective delivery requires the agent to diffuse into the infected cells. Chemical modification of the agent to neutralize negative or positive charges may be all that is required for penetration. However, in the event that charge neutralization is insufficient, the modified agent can be co-formulated with permeability enhancers, such as Azone or oleic acid, in a liposome. The liposomes can either represent a slow release presentation vehicle in which the modified agent and permeability enhancer transfer from the liposome into the targeted cell, or the liposome phospholipids can participate directly with the modified agent and permeability enhancer in facilitating cellular delivery. In some cases, both the agent and permeability enhancer can be formulated into a suppository formulation for slow release.

Agents may also be systemically administered. Systemic absorption refers to the accumulation of drugs in the blood stream followed by distribution throughout the entire body. Administration routes which lead to systemic absorption include: intravenous, subcutaneous, intraperitoneal, intranasal, intrathecal and ophthalmic. Each of these administration routes expose the agent to an accessible diseased or other tissue. Subcutaneous administration drains into a localized lymph node which proceeds through the lymphatic network into the circulation. The rate of entry into the circulation has been shown to be a function of molecular weight or size. The use of a liposome or other drug carrier localizes the agent at the lymph node. The agent can be modified to diffuse into the cell, or the liposome can directly participate in the delivery of either the unmodified or modified agent to the cell.

Most preferred delivery methods include liposomes (10–400 nm), hydrogels, controlled-release polymers, microinjection or electroporation (for ex vivo treatments) and other pharmaceutically applicable vehicles. The dosage will depend upon the disease indication and the route of administration but should be between 10–2000 mg/kg of body weight/day. The duration of treatment will extend through the course of the disease symptoms, usually at least 14–16 days and possibly continuously. Multiple daily doses are anticipated for topical applications, ocular applications and vaginal applications. The number of doses will depend upon disease delivery vehicle and efficacy data from clinical trials.

Establishment of therapeutic levels of agent within the target cell is dependent upon the rate of uptake and degradation. Decreasing the degree of degradation will prolong the intracellular half-life of the agent. Thus, chemically modified agents, e.g., oligonucleotides with modification of the phosphate backbone, or capping of the 5' and 3' ends of the oligonucleotides with nucleotide analogues may require different dosaging.

It is evident from the above results, that by modulating telomerase activity and monitoring telomere length and telomerase activity, one may provide therapies for proliferative diseases and monitor the presence of neoplastic cells and/or proliferative capacity of cells, where one is interested in regeneration of particular cell types. Assays are provided which allow for the determination of both telomere length, particularly as an average of a cellular population, or telomerase activity of a cellular population. This information may then be used in diagnosing diseases, predicting outcomes, and providing for particular therapies.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

```
CSITU9

1   ATATATGCGCTACATAAATGTATCTAGATGCAATTATCTAGATACATATA

51  AGAAAGTATTTGAAGGCCTTCTACAAGGCTTAGTTATTATATTGGTTCAT

101 ACAAGTTCTTCTTCAG

Total number of bases is: 176
DNA sequence composition: 39 A; 17 C; 15 G; 42 T; 0 Other

CSITU13

1   ATCCTTCTCCGCAAACTAACAGGAACAGAAAACCAAACACTGCATGTTCT

51  CACATCATTGTGGGAGTTGAACAATGAGAACACATGGACACAGGGAGGGG

101 AACATCACACACTCGGGGTGTCAGCCGGGTGGGAGGGTAGAGGAGGAGAA

151 ATACCTAAGTTCCAGATGACAGGTTG

Total number of bases is: 176
DNA sequence composition: 58 A; 37 C; 50 G; 31 T; 0 Other
```

-continued

CSITU22

1    GATCTATGCTACCTCTAGGGATGGCACCATTCACAAGCACAAAGGAGATG

51   TCAGTGATTAAAAACACATGCTCTGGAGTCTGAGAGACTTTGAGACTTGC

101  TAGCTTGTGACTCTGCAGAGTTTAAGGTATCTGGACCCCTTTTTCCCTCA

151  TGTGCATAATGAAGAGATT

Total number of bases is: 169
DNA sequence composition: 47 A; 35 C; 39 G; 48 T; 0 Other

CSITU24

1    GATCAACACTGTTAGTTGAGTACCCACATCACAAACGTGATTCTCAGAAT

51   GCCTTCCTTCCTGTCTAGTTTCTATAGGTAGATATTTCCTTTTTCAGCAT

101  AGGCCTGAAAAGCCGCCTCCAAATGCCCGCCTTCCAGACACTATAAAAAG

151  AGGGTTCAAACCTACTCTATGAAAGGGAATGTTCAACACAGA

Total number of bases is: 192
DNA sequence composition: 58 A; 49 C; 33G; 52 T; 0 Other

CSITU33

1    GATCTGTTTATTATTCTTCCAATATCTCCCCATCTCTTAAAAATTGGTTA

51   TTTCTTCGTTCATACATTTTTATCTCCCAAATTANNNNTGAGACTGGTTT

101  GAAGAGAGGAAAGCAATGTACACACTTTTATATTCCACCATGTATATCCG

151  GATATCC

Total number of bases is: 157
DNA sequence composition: 43 A; 32 C; 19 G; 59 T; 4 Other

CSITU37

1    AATCCTCCTACCTTAACCTCCCTTTGTTAGCCTGCCATTACAGGTGTGAG

51   CCACCATTGCTCATTCGTCCGTTTATTCATTCAACAAATCAATCGATCTA

101  TTACATGTGAGGGACTCTTCAGGTCATGGGAATTC

Total number of bases is: 135
DNA sequence composition: 32 A; 37 C; 22 G; 44 T; 0 Other

CSITU38

1    GATCACTTGAGCCCAGGAGTTTGAGACCAGCCTGGGTGACATGGCAAAAC

51   CCCATCTCTACCAAAAGAAAAAAANNNNACAAATTGGTGGTGTTGATGGT

101  CGGCGACCATTGATCCC

Total number of bases is: 117
DNA sequence composition: 35 A; 27 C; 28 G; 23 T; 4 Other

CSITU51

1    GATCAGGGAGGGGCCGAAAACTGGAGATGCAGGTGTGCTGTAAGACACTG

51   CAGAGAGGGCATTTACCTGCCCCATCATCCAGCACAGGAACAGCGACTGA

101  CAGCGCTCACCCACCCACCATCGCCAGTCACACTGGG

Total number of bases is: 137
DNA sequence composition: 37 A; 42 C; 39 G; 19 T; 0 Other The CTR-enriched subtelomeric PCR amplified library has also been used to screen a cDNA library. 32 clones have been isolated, and partial sequence has been obtained form five clones. Their sequences are shown in Table 10.

Two of these clones, PhC4 and PHCS, have been characterized on Northern blots. Both hybridize to the same two mRNAs of approximately 6.2 and 7.7 Kb. Since the 3' sequences of PHC4 and PHCS are different, this suggests they may represent alternative splicing products of the same gene. Both messages are abundant in PDL 38 IMR90 cells, which have relatively long telomeres, and neither is expressed in the immortal IDH4 cells (which have very short telomeres) that were derived from IMR90. This supports the hypothesis that the expression of genes located in the subtelomeric DNA are regulated by telomeric length. This data is evidence that the above mentioned procedure provides a means of obtaining sequences located in the proximity of telomeres, some of which encode mRNA. Those sequences which are unique to individual chromosomes will be useful in genomic mapping. Those which are active genes and differentially expressed in cells with differing telomere length, may play an important role in communicating information relating to telomere length to the cell. Genes that regulate the onset of M1 senescence can be isolated by these means, as will as genes which modulate telomerase activity. The function of the telomeric genes can be identified by overexpression and knock-out in young senescent and immortal cells. Such cDNAs, antisense molecules, and the encoded proteins may have important therapeutic and diagnostic value in regard to their modulation of cell proliferation in age-related disease and hyperplasias such as cancer.

TABLE 10

Partial Sequence of subtelomeric cDNA clones.

PHC4-5'end

```
1    GGCTCGAGAACGGGAGGAGGGGGCTCTTGTATCAGGGCCCGTTGTCACAT

51   CTGCTCTCAGCTTGTTGAAAACTCATAATC
```

Total number of bases is: 80
DNA sequence composition: 17 A; 19 C; 24 G; 20 T; 0 Other

PHC5-3'END

```
1    AGGTCCCTTGGTCGTGATCCGGGAAGGGGCCTGACGTTGCGGGAGATCGA

51   GTTTTCTGTGGGCTTGGGGAACCTCTCACGTTGCTGTGTCCTGGTGAGCA

101  GCCCGGACCAATAAACCTGCTTTTCTTAAAAGGAAAAAAAAAAAAAAAAA

151  AAAAAAA
```

Total number of bases is: 157
DNA sequence composition: 47 A; 31 C; 44 G; 3S T; 0 Other

PHC7

```
1    ATCTAGGTTTTTTAAAAAAGCTTTGAGAGGTAATTACTTGCATATGAGAG

51   AATAAAACATTTGGCACATTGTTAAAAAAAAAAAAAAAAAAAAAAAAAAA

101  AAAAAAAAAAAAAAAAAAAA
```

Total number of bases is: 120
DNA sequehce composition: 73 A; 7 C; 14 G; 26 T; 0 Other

PHC8

```
1    CTCATTTACTTTTCTCTTATAGCGTGGCTTTAAACATATATACATTTGTA

51   TATATGTATATATGAATATAATGTATAAAATGTATGTAGATGTATATACA

101  AAAAATAAACGAGATGGGTTAAAGATATGTAAAAAAAAAAAAAAAAAAA
```

Total number of bases is: 149
DNA sequence composition: 69 A; 11 C; 19 G; 50 T; 0 Other

PHC9

```
1    AGTCCCAGCTACTCGGGAGGGCTGAGGCAGGAGAATGGCGTGAACCCAGG

51   AGGCGAAGCTTGCAGTGAGCTGAGATCGCGCCACTGCACTCCAGCCTGGA

101  CGACAGAGCGAGACTCTGTCTCAAAAAAAAAAAAAAAAAAAA
```

Total number of bases is: 169
DNA sequence composition: 47 A; 35 C; 39 G; 48T; 0 Other Example 20

Isolation of Factors that Derepress Telomerase

The M2 mechanism of cellular senescence occurs when insufficient numbers of telomeric repeats remain to support continued cellular proliferation. Escape from the M2 mechanism and immortalization occur concomitantly with the induction of telomerase activity and stabilization of telomere length, and thus the inactivation of the M2 mechanism directly or indirectly derepresses telomerase.

The gene(s) regulating the M2 mechanism have been tagged with retroviral sequences. The methods by which this was accomplished consisted of first determining the frequency at which a clone of SV40 T-antigen transfected human lung fibroblasts was able to escape M2 and become immortal (T-antigen blocks the M1 mechanism, thus the M2 mechanism is the sole remaining block to immortality in these cells). The pre-crisis cells were then infected with a defective retrovirus in order to insertionally mutagenize potential M2 genes, and it was shown that the frequency of immortalization was increased by almost three-fold. Finally, pulse-field electrophoresis of different immortalized insertionally mutagenized lines was used to identify which of the lines became immortal due to an insertion into the same M2 gene. Since an M2 mechanism gene has now been tagged with retroviral sequences, those with ordinary skills in the art can now clone and identify the specific gene. The methods used were as follows:

The frequency of escape from crisis (e.g., the immortalization frequency of T-antigen expressing cells) was estimated using an approach based on what is essentially a fluctuation analysis as previously described (Shay, J. W., and Wright, W. E. (1989) Exp. Cell Res. 184, 109–118). SW26 cells (a clone isolated from IMR 90 normal human lung fibroblasts transfected with a vector expressing SV40 large T antigen) were expanded approximately 15 PDL's before crisis into multiple series at a constant cell density of 6667 cells/cm$^2$. Each series was subsequently maintained as a separate culture, so that at the end of the experiment the fraction of each series that gave rise to immortal cell lines could be determined. Cultures were split at or just prior to confluence at 6667 cells/cm$^2$. Once cells reached crisis they were split at least once every three weeks until virtually no surviving cells remained or the culture had immortalized. When too few cells were obtained, all of the cells were put back into culture in a single dish. Fibroblasts were considered immortal if vigorous growth occurred after crisis during two subcultivations in which 1000 cells were seeded into 50 cm$^2$ dishes and allowed to proliferate for three weeks for each cycle.

SW 26 cells enter crisis at approximately PDL 82–85. Numerous vials of SW26 cells (8×10$^6$ cells/vial) were frozen at PDL 71, and testing verified that spontaneous immortalization events had not yet occurred. Five vials were thawed, scaled up for 4 days to approximately 10$^8$ cells (thus to approximately PDL 74), then trypsinized and combined into a single pool of cells in 40 ml of medium and distributed into 200 10 cm$^2$ dishes. Thirty dishes were treated with 25 µg/ml bleomycin sulfate (a chemical mutagen) for two hours in serum free medium one day later. Since this concentration of bleomycin sulfate resulted in approximately 50% of the IMR-90 SW26 cells dying, these dishes had been plated at twice the cell density as the rest.

The remainder of the dishes were used as controls (70 dishes) or infected with LNL6 defective retrovirus (100 dishes). LML6 was generated in the amphotrophic packaging line PA317 according to previously described procedures (Miller and Rosman, 1989, Biotechniques 7, 980–990). Culture supernatant from LNL6 infected PA317 cells were used to infect one hundred dishes containing approximately 5×10$^5$ cells in the presence of 2 µg/ml of polybrene. Control medium supernatant from uninfected PA317 cells containing polybrene were used to treat 70 dishes and served as controls. Within a few days after infection, all control and experimental dishes were counted and each dish contained 1–2×10$^6$ cells. The PDL of each dish was calculated and cells were then replated at 0.33×10$^6$ in 50 cm$^2$ dishes and maintained separately to conduct the fluctuation analysis.

Bleomycin treated SW26 cells escaped crisis with an approximately two-fold higher frequency (7.7×10$^{-7}$) than the spontaneous rate (4.7×10$^{-7}$). Pre-crisis SW26 cells infected with the defective retrovirus LNL6 in order to produce insertional mutations yielded a frequency of escape from crisis (10.9×10$^{-7}$) that was 2–3 fold greater than the rate from simultaneous control series mock-infected with culture supernatant from the non-infected packaging line.

TABLE 10

Bleomycin Sulfate Exposure and Retrovirus Infection Increase Immortalization Frequency

| Addition | Immortalization | Frequency |
| --- | --- | --- |
| Nil | 10/68 | 4.4 × 10$^{-7}$ |
| Bleomycin sulfate | 7/27 | 7.7 × 10$^{-7}$ |
| LNL6 retrovirus | 36/99 | 10.9 × 10$^{-7}$ |

Immortalization is expressed as the number of immortal lines per number of culture series, each series being derived from a single dish at the initiation of the experiment. Frequency is expressed as the probability of obtaining an immortal cell line based on the number of cells plated at each passage (not per cell division).

DNA has been isolated from 23 of the 36 independent cell lines obtained following insertional mutagenesis with LNL6, and 7 of these (30%) did not contain retroviral sequences when analyzed on Southern Blots, while most of the remainder contained single insertions. Given that those without retroviral insertions had to represent spontaneous immortalization events, most of the remaining clones with retroviral insertions should be due to insertional mutagenesis if the frequency of immortalization was actually increased 2–3 fold. DNA from 12 lines has been digested with the rare-cutting enzyme Sfi1, followed by pulse-field electrophoresis, transfer to nylon membranes and probing with the retrovirus LTR. Six of the 12 lines contained a common band of approximately 350 Kbp that hybridized to the retroviral LTR. Four of these six have also been analyzed following BamH1 digestion, and three of these four also contained a common band of approximately 20 Kbp. Given that the retrovirus is 6 Kbp long, this strongly suggests that the retrovirus has inserted multiple times within 14 Kbp region of DMNA, which is strongly suggestive of a single gene. Digestion with EcoR1, which cuts within the retrovirus, yields different size fragments for each line, establishing that they represent different insertional events and are truly independent isolates. The use of retroviral sequences to clone the genomic DNA flanking the insertion sites should now permit positive identification of a gene involved in the M2 mechanism. Interference with the function of that gene (for example, using antisense techniques) should result in the derepression of telomerase and the ability to extend the lifespan of normal human cells. This gene should also prove to be mutated in a variety of cancer cells, and is thus likely to be of diagnostic and therapeutic value in cancer as well.

Example 21

Tissue Distribution of Telomerase Activity in Primates

S100 extracts were prepared from a 12 year old healthy male Rhesus Macaque to determine the tissue distribution of telomerase activity. Abundant telomerase activity was detected only from the testis. Samples of tissue from the brain, kidney, and liver displayed no detectable activity. This suggests that telomerase inhibition as a therapeutic modality for cancer has the unique advantage of not being abundant in normal tissues with the exception of the germ line. Therefore telomerase inhibitors should be targeted away from the germ cells in reproductive aged individuals to decrease the chance of birth defects. Such targeting may be accomplished by localized injection or release of the active agent near the site of the tumor. The effect of the telomerase inhibitors in the male may be easily determined by measuring telomere repeat length in the sperm.

What is claimed is:

1. A method of screening to determine whether a non-deoxyribonucleotide test compound can inhibit telomerase activity of a cell, said method comprising:

providing a reaction mixture that comprises a preparation comprising telomerase activity, an oligonucleotide primer for telomerase activity, nucleoside triphosphates, and a plurality of test compounds;

incubating said reaction mixture under conditions which, in the absence of an inhibitor of said telomerase activity, allow said oligonucleotide primer to be extended by telomerase activity to incorporate one or more of said nucleoside triphosphates; and determining whether said oligonucleotide primer is extended.

2. A screening method according to claim 1 wherein said telomerase activity is a protozoan telomerase activity.

3. A screening method according to claim 2 wherein said protozoan telomerase activity is a ciliate telomerase activity.

4. A screening method according to claim 3, wherein said ciliate telomerase activity is a *Tetrahymena telomerase* activity.

5. A screening method according to claim 1 wherein said telomerase activity is a fungal telomerase activity.

6. A screening method according to claim 1 wherein said telomerase activity is a mammalian telomerase activity.

7. A screening method according to claim 6 wherein said mammalian telomerase activity is a human telomerase activity.

8. A screening method according to claim 1 wherein said oligonucleotide primer or one of said nucleoside triphosphates is labeled with a detectable label.

9. A screening method according to claim 8 wherein said detectable label is biotin.

10. A screening method according to claim 1 wherein said non-deoxyribonucleotide test compound is a polypeptide or a synthetic chemical.

11. A screening method according to claim 1 wherein said non-deoxyribonucleotide test compound is a synthetic chemical.

12. A screening method according to claim 1 wherein a plurality of test compounds are assayed in reaction mixtures in one or more 96-well microtiter plates.

13. A screening method according to claim 1 wherein said non-deoxyribonucleotide test compound is selected from the group consisting of anticancer compounds, antiparasite compounds, and antifuingal compounds.

14. A method according to claim 1 further comprising correlating a lack of or a reduction in primer extension in the presence of said non-deoxyribonucleotide test compound, as compared with primer extension in the absence of said non-deoxyribonucleotide test compound, with inhibition of said telomerase activity by said non-deoxyribonucleotide test compound.

15. A method of screening to determine whether a test compound can inhibit telomerase activity of a mammalian or fungal cell, said method comprising:

providing a reaction mixture that comprises a preparation comprising a telomerase activity selected from the group consisting of a mammalian telomerase activity and a fungal telomerase activity, an oligonucleotide primer for said telomerase activity, nucleoside triphosphates, and said test compound;

incubating said reaction mixture under conditions which, in the absence of an inhibitor of said telomerase activity, allow said oligonucleotide primer to be extended to incorporate one or more of said nucleoside triphosphates;

determining whether said oligonucleotide primer is extended in the presence of said test compound to the same extent as when said test compound is absent from the reaction mixture;

exposing a mammalian or fungal cell to the test compound under conditions which, in the absence of an inhibitor of telomerase activity of said cell, allow telomere maintenance; and correlating telomere maintenance or lack thereof in said cell with inhibition of telomerase activity by said test compound.

16. A screening method according to claim 15 wherein said fungal telomerase activity is a yeast telomerase activity.

17. A screening method according to claim 16 wherein said yeast telomerase activity is derived from a yeast selected form the group consisting of *Candida albicans, Candida guillermondii, Candida pseudotropicals, Candida lusitaniae, Candida maltosa, Candida tropicalis, Kluyveromyces lactis*, and *Sacchromyces cerevisiae*.

18. A screening method according to claim 15 wherein said mammalian telormerase activity is derived from a mammal selected from the group consisting of a primate, equine, bovine, ovine, porcine, feline, and canine animal.

19. A screening method according to claim 15 wherein said mammalian telomerase activity is a human telomerase activity.

20. A screening method according to claim 19 wherein the method is a high throughput test compound screen.

21. A screening method according to claim 20 wherein the reaction mixture comprises a plurality of test compounds.

22. A screening method according to claim 15 wherein said oligonucleotide primer or one of said nucleoside triphosphates is labeled with a detectable label.

23. A screening method according to claim 22 wherein said detectable label is biotin.

24. A screening method according to claim 15 wherein said test compound is a nucleoside analog.

25. A method of screening to determine whether a test compound can inhibit telomerase activity of a human cell, said method comprising:

combining in a reaction mixture a preparation comprising human telomerase activity, an oligonucleotide primer for said telomerase activity, nucleoside triphosphates, and said test compound;

incubating said reaction mixture under conditions which, in the absence of an inhibitor of such telomerase activity, allow said oligonucleotide primer to be extended to incorporate one or more of said nucleoside triphosphates;

determining whether said oligonucleotide primer is extended in the presence of said test compound to the same extent as when said test compound is absent from the reaction mixture;

exposing cells which express a human telomerase activity to the test compound under conditions which, in the absence of an inhibitor of human telomerase activity expressed in said cells, allow telomere maintenance; and correlating telomere maintenance or lack thereof in said cell with inhibition of telomerase activity by said test compound.

26. A screening method according to claim 25 wherein the method is a high throughput test compound screen.

27. A screening method according to claim 26 wherein the reaction mixture comprises a plurality of test compounds.

28. A screening method according to claim 15 wherein said oligonucleotide primer or one of said nucleoside triphosphates is labeled with a detectable label.

29. A screening method according to claim 28 wherein said detectable label is biotin.

30. A screening method according to claim 25 wherein said test compound is a nucleoside analog.

31. A method of screening to determine whether an oligonucleotide test compound can inhibit telomerase activity of a mammalian or fungal cell, said method comprising:

providing a reaction mixture that comprises a preparation comprising a telomerase activity selected from the group consisting of a mammalian telomerase activity and a fungal telomerase activity, an oligonucleotide primer for said telomerase activity, nucleoside triphosphates, and said oligonucleotide test compound;

incubating said reaction mixture under conditions which, in the absence of an inhibitor of said telomerase activity, allow said oligonucleotide primer to be extended to incorporate one or more of said nucleoside triphosphates;

determining whether said oligonucleotide primer is extended in the presence of said oligonucleotide test compound to the same extent as when said oligonucleotide test compound is absent from the reaction mixture and, if not;

exposing a mammalian or fungal cell to the oligonucleotide test compound under conditions which, in the absence of an inhibitor of telomerase activity of said cell, allow telomere maintenance; and correlating telomere maintenance or lack thereof in said cell with inhibition of telomerase activity by said oligonucleotide test compound.

32. A screening method according to claim 31 wherein said fungal telomerase activity is a yeast telomerase activity.

33. A screening method according to claim 32 wherein said yeast telomerase activity is derived from a yeast selected from the group consisting of *Candida albicans, Candida guillermondii, Candida pseudotropicalis, Candida lusitaniae, Candida maltosa, Candida tropicalis, Kluyveromyces lactis*, and *Sacchromyces cerevisiae*.

34. A screening method according to claim 31 wherein said mammalian telomerase activity is derived from a mammal selected from the group consisting of a primate, equine, bovine, ovine, porcine, feline, and canine animal.

35. A screening method according to claim 31 wherein said mammalian telomerase activity is a human telomerase activity.

36. A screening method according to claim 35 that is a high throughput test compound screen.

37. A screening method according to claim 36 wherein a plurality of oligonucleotide test compounds are assayed in reaction mixtures in one or more 96-well microtiter plates.

38. A screening method according to claim 31 wherein said primer or one of said nucleoside triphosphates is labeled with a detectable label.

39. A screening method according to claim 38 wherein said detectable label is biotin.

40. A screening method according to claim 31 wherein said oligonucleotide test compound is an antisense oligonucleotide.

41. A screening method according to claim 40 wherein said antisense oligonucleotide comprises ribonucleotides.

42. A screening method according to claim 31 wherein said oligonucleotide test compound is a polyribonucleotide antisense RNA.

43. A screening method according to claim 42 wherein said polyribonucleotide antisense RNA further comprises a ribozyme.

44. A screening method according to claim 31 wherein said oligonucleotide test compound is a ribozyme.

45. A method of screening to determine whether an oligonucleotide test compound can inhibit telomerase activity of a human cell, said method comprising:

combining in a reaction mixture a preparation comprising human telomerase activity, an oligonucleotide primer for said telomerase activity, nucleoside triphosphates, and said test compound;

incubating said reaction mixture under conditions which, in the absence of an inhibitor of such telomerase activity, allow said oligonucleotide primer to be extended to incorporate one or more of said nucleoside triphosphates; and determining whether said oligonucleotide primer is extended in the presence of said oligonucleotide test compound to the same extent as when said oligonucleotide test compound is absent from the reaction mixture, and, if not;

exposing cells which express a human telomerase activity to the oligonucleotide test compound under conditions which, in the absence of an inhibitor of human telomerase activity expressed in said cells, allow telomere maintenance; and correlating telomere maintenance or lack thereof in said cells with inhibition of said human telomerase activity by said oligonucleotide test compound.

46. A screening method according to claim 45 that is a high throughput test compound screen.

47. A screening method according to claim 46 wherein a plurality of oligonucleotide test compounds are assayed in reaction mixtures in one or more 96-well microtiter plates.

48. A screening method according to claim 45 wherein said oligonucleotide primer or one of said nucleoside triphosphates is labeled with a detectable label.

49. A screening method according to claim 48 wherein said detectable label is biotin.

50. A screening method according to claim 45 wherein said oligonucleotide test compound is an antisense oligonucleotide.

51. A method according to claim 50 wherein said antisense oligonucleotide comprises ribonucleotides.

52. A method according to claim 45 wherein said oligonucleotide test compound is a polyribonucleotide antisense RNA.

53. A method according to claim 52 wherein said polyribonucleotide antisense RNA further comprises a ribozyme.

54. A method according to claim 45 wherein said oligonucleotide test compound is a ribozyme.

* * * * *